(12) United States Patent
Carrasco et al.

(10) Patent No.: US 11,391,739 B2
(45) Date of Patent: Jul. 19, 2022

(54) COMPOSITIONS AND METHODS FOR TREATING MULTIPLE MYELOMA

(71) Applicant: DANA-FARBER CANCER INSTITUTE, INC., Boston, MA (US)

(72) Inventors: Ruben Carrasco, Brookline, MA (US); Di Zhu, Newton, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 55 days.

(21) Appl. No.: 16/441,166

(22) Filed: Jun. 14, 2019

(65) Prior Publication Data

US 2020/0018757 A1 Jan. 16, 2020

Related U.S. Application Data

(62) Division of application No. 15/516,300, filed as application No. PCT/US2015/053460 on Oct. 1, 2015, now Pat. No. 10,365,280.

(60) Provisional application No. 62/119,377, filed on Feb. 23, 2015, provisional application No. 62/058,911, filed on Oct. 2, 2014.

(51) Int. Cl.
*G01N 33/574* (2006.01)
*C12N 15/113* (2010.01)
*C12Q 1/6886* (2018.01)

(52) U.S. Cl.
CPC ..... *G01N 33/57407* (2013.01); *C12Q 1/6886* (2013.01); *C12Q 2600/118* (2013.01); *C12Q 2600/136* (2013.01); *C12Q 2600/158* (2013.01); *G01N 2333/70596* (2013.01); *G01N 2333/99* (2013.01); *G01N 2500/02* (2013.01); *G01N 2800/52* (2013.01); *G01N 2800/56* (2013.01)

(58) Field of Classification Search
CPC combination set(s) only.
See application file for complete search history.

(56) References Cited

U.S. PATENT DOCUMENTS

| | | | |
|---|---|---|---|
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Surani et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,840,305 A | 11/1998 | Bukrinsky et al. | |
| 5,928,639 A | 7/1999 | Slavin | |
| 5,929,212 A | 7/1999 | Jolliffe et al. | |
| 6,143,292 A | 11/2000 | Slavin | |
| 8,632,772 B2 | 1/2014 | Anderson et al. | |
| 8,673,593 B2 | 3/2014 | Chilcote et al. | |
| 8,999,289 B2 | 4/2015 | Anderson et al. | |
| 2003/0064473 A1 | 4/2003 | Baker et al. | |
| 2008/0075722 A1* | 3/2008 | DePinho | C12Q 1/6837 424/138.1 |
| 2010/0183599 A1 | 7/2010 | Mundy et al. | |
| 2010/0239581 A1 | 9/2010 | Joseloff et al. | |
| 2012/0184494 A1 | 7/2012 | Zangari et al. | |
| 2013/0116225 A1 | 5/2013 | Sheshbaradaran et al. | |

FOREIGN PATENT DOCUMENTS

| | | |
|---|---|---|
| WO | 199733604 A1 | 9/1997 |
| WO | 2002013763 A1 | 2/2002 |
| WO | 2012023093 A1 | 2/2012 |
| WO | 2013155048 A1 | 10/2013 |

OTHER PUBLICATIONS

Bauer et al. (Oncogene, 2009, 28:2784-2795).*
Desmetz et al (Clinical Cancer Research, 2009, 15:4733-4741).*
Yurchenko et al (Clinical & Experimental Immunology, 2010, 160:305-317).*
Santa Cruz Biotechnology, EMMPRIN (UM-8D6), data sheet printed Aug. 2021.*
Arendt et al. (Blood, 2011, 118: abstract 470).*
Arendt et al. (Oct. 2012) "Increased expression of extracellular matrix metalloproteinase inducer (CD147) in multiple myeloma: role in regulation of myeloma cell proliferation," Leukemia. 26(10):2286-2296.
Badros et al. (2002) "Improved outcome of allogeneic transplantation in high-risk multiple myeloma patients after nonmyeloablative conditioning," Journal of Clinical Oncology. 20(5):1295-1303.
Boerner et al. (1991) "Production of antigen-specific human monoclonal antibodies from in vitro-primed human splenocytes," The Journal of Immunology. 147(1):86-95.
Calimeri et al. (2011) "A unique three-dimensional SCID-polymeric scaffold (SCID-synth-hu) model for in vivo axpansion of human primary multiple myeloma cells," Leukemia. 25(4):707-711.
Carell et al. (1994) "A Solution-Phase Screening Procedure for the Isolation of Active Compounds from a Library of Molecules," Angewandte Chemie International Edition. 33(20):2061-2064.
Cho et al. (1993) "An unnatural biopolymer," Science—New York then Washington. 261:1303-1303.
Dewitt et al. (1993) "'Diversomers': An approach to nonpeptide, nonoligomeric chemical diversity," Proceedings of the National Academy of Sciences. 90(15):6909-6913.
Durie et al. (1975) "A clinical staging system for multiple myeloma correlation of measured myeloma cell mass with presenting clinical features, response to treatment, and survival," Cancer. 36(3):842-854.

(Continued)

*Primary Examiner* — Laura B Goddard
(74) *Attorney, Agent, or Firm* — Lathrop GPM LLP; Brian C. Trinque

(57) ABSTRACT

Provided by the invention are methods for identifying therapeutic agents for treating multiple myeloma or another hematological malignancy, as well as methods for determining the prognosis of a patient with multiple myeloma or another hematological malignancy. The methods are based in part on the inventors' discovery that an extracellular form of cyclophilin A binds to CD147 expressed on multiple myeloma cells.

16 Claims, 38 Drawing Sheets

Specification includes a Sequence Listing.

(56) References Cited

OTHER PUBLICATIONS

Erb et al. (1994) "Recursive deconvolution of combinatorial chemical libraries," Proceedings of the National Academy of Sciences. 91(24):11422-11426.
Ficarro et al. (2009) "Improved electrospray ionization efficiency compensates for diminished chromatographic resolution and enables proteomics analysis of tyrosine signaling in embryonic stem cells," Analytical Chemistry. 81(9):3440-3447.
Fishwild et al. (1996) "High-avidity human IgGK monoclonal antibodies from a novel strain of minilocus transgenic mice," Nature Biotechnology 14(7):845-851.
Gallop et al. (1994) "Applications of combinatorial technologies to drug discovery. 1. Background and peptide combinatorial libraries," Journal of Medicinal Chemistry. 37(9):1233-1251.
Hoogenboom et al. (1992) "By-passing immunisation: human antibodies from synthetic repertoires of germline VH gene segments rearranged in vitro," Journal of Molecular Biology. 227(2):381-388.
Garashi et al. (2004) "Enhanced cytotoxicity of allogeneic NK cells with killer immunoglobulin-like receptor ligand incompatibility against melanoma and renal cell carcinoma cells," Blood 104(1):170-177.
Jones et al. (1986) "Replacing the complementarity-determining regions in a human antibody with those from a mouse," Nature 321(6069):522-525.
Levanon et al. (2010) "Primary ex vivo cultures of human fallopian tube epithelium as a model for serous ovarian carcinogenesis," Oncogene. 29(8):1103-1113.
Lonberg et al. (1994) "Antigen-specific human antibodies from mice comprising four distinct genetic modifications," Nature. 368(6474):856-859.
Bauer et al. (2009) "Cyclophilins contribute to Stat3 signaling and survival of multiple myeloma cells," Oncogene. 28:2784-2795.
Maloney et al. (2003) "Allografting with nonmyeloablative conditioning following cytoreductive autografts for the treatment of patients with multiple myeloma," Blood. 102(9):3447-3454.
Mani et al. (2009) "BCL9 promotes tumor progression by conferring enhanced proliferative, metastatic, and angiogenic properties to cancer cells," Cancer Research 69(19):7577-7586.

Marks et al. (1991) "By-passing immunization: human antibodies from V-gene libraries displayed on phage," Journal of Molecular Biology. 222(3):581-597.
Marks et al. (1992) "By-Passing Immunization: Building High Affinity Human Antibodies by Chain Shuffling," Nature Biotechnology. 10(7):779-783.
Morrison (1994) "Success in specification," Nature. 368(6474):812-813.
Neuberger (1996) "Generating high-avidity human Mabs in mice," Nature Biotechnology. 14(7):826-826.
Peng et al. (2001) "Proteomics: the move to mixtures," Journal of Mass Spectrometry. 36(10):1083-1091.
Presta (1992) "Antibody engineering," Current Opinion in Structural Biology. 2:593-596.
Ria et al. (2009) "Gene expression profiling of bone marrow endothelial cells in patients with multiple myeloma," Clinical Cancer Research. 15(17):5369-5378.
Riechmann et al. (1988) "Reshaping human antibodies for therapy," Nature. 332(6162):323-327.
Sukhdeo et al. (2007) "Targeting the β-catenin/TCF transcriptional complex in the treatment of multiple myeloma," Proceedings of the National Academy of Sciences. 104(18):7516-7521.
Takada et al. (2012) "Targeted disruption of the BCL9/β-catenin complex inhibits oncogenic Wnt signaling," Science Translational Medicine. 4(148):148ra117.
Tricot et al. (1996) "Graft-versus-myeloma effect: proof of principle," Blood. 87(3):1196-1198.
Verhoeyen et al. (1988) "Reshaping human antibodies: grafting an antilysozyme activity," Science. 239 (4847):1534-1536.
Zuckermann et al. (1994) "Discovery of nanomolar ligands for 7-transmembrane G-protein-coupled receptors from a diverse N-(substituted) glycine peptoid library," Journal of Medicinal Chemistry. 37(17):2678-2685.
Zhu et al. (2015) "The Cyclophilin A-CD147 complex promotes the proliferation and homing of multiple myeloma cells.," Nature Medicine. 21:572-583.
International Search Report with Written Opinion corresponding to International Patent Application No. PCT/US15/53460, dated Feb. 4, 2016, 17 pages.
Carell et al. (1994) "A novel procedure for the synthesis of libraries containing small molecules," Agnew Chem Int Ed Engl. 33:2059-61.

* cited by examiner

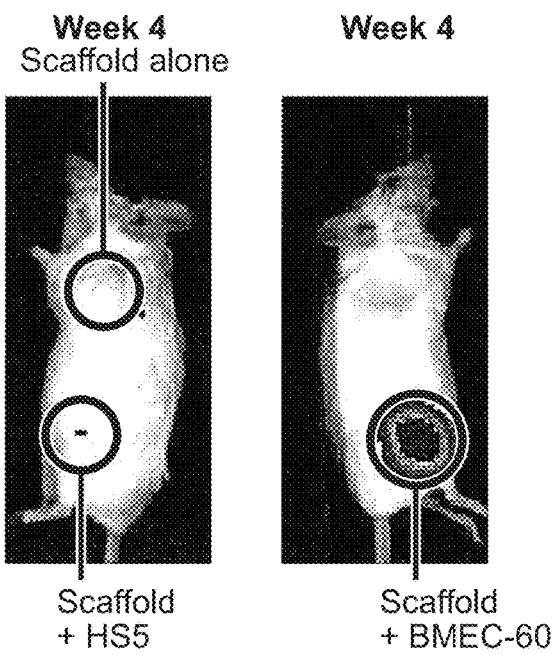
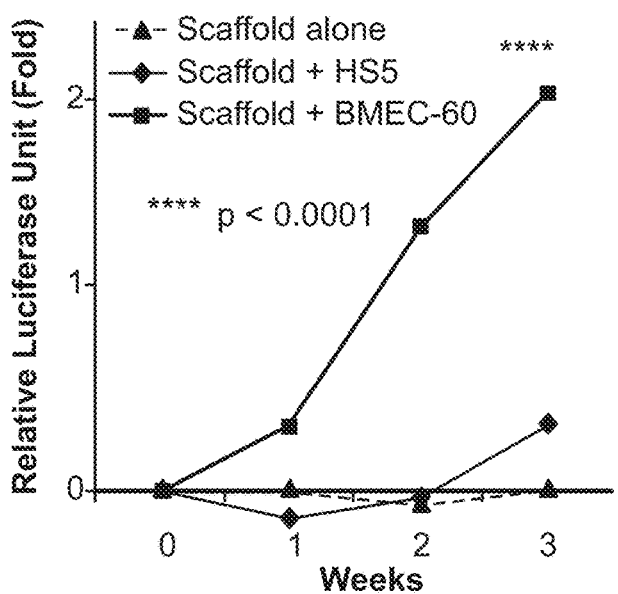
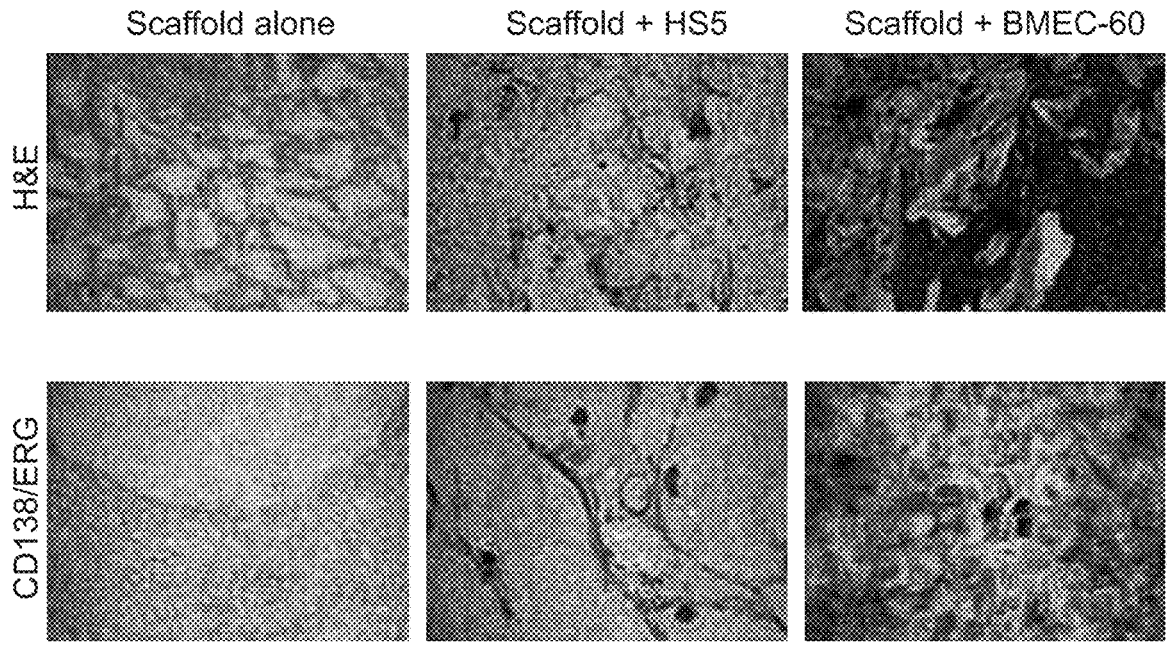

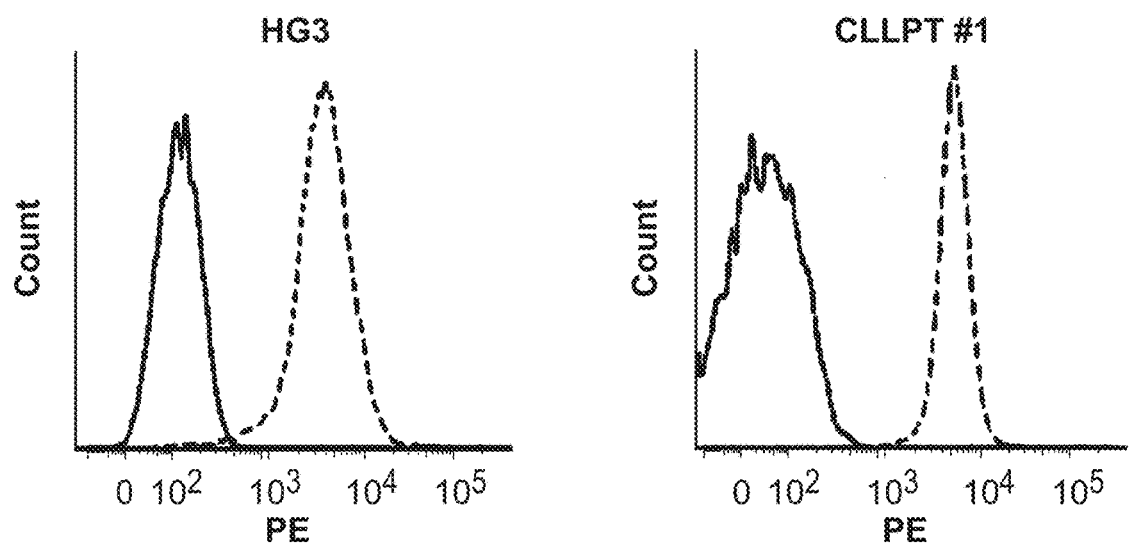
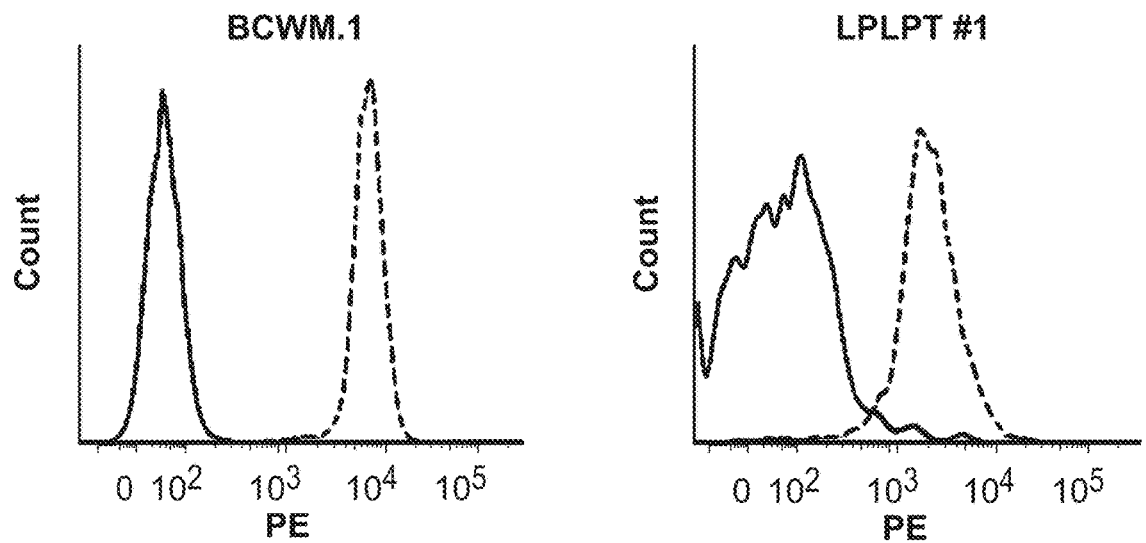

COMPOSITIONS AND METHODS FOR TREATING MULTIPLE MYELOMA

CROSS REFERENCE TO RELATED APPLICATIONS

This application is a divisional of U.S. application Ser. No. 15/516,300, filed on Mar. 31, 2017, which is a national stage entry of PCT Application No. PCT/US15/53460, filed on Oct. 1, 2015, which claims priority to U.S. Provisional Application No. 62/119,377 filed on Feb. 23, 2015 and U.S. Provisional Application No. 62/058,911 filed on Oct. 2, 2014 and, the contents of which are hereby incorporated by reference in their entirety.

STATEMENT AS TO FEDERALLY SPONSORED RESEARCH

This invention was made with government support under grant number R01 CA151391 awarded by the National Institutes of Health. The government has certain rights in the invention.

BACKGROUND

The invention relates generally to compositions and methods for treating malignancies, and more particularly to compositions and methods for treating a hematological malignancy such as multiple myeloma.

SUMMARY

The invention is based in part on the discovery that the extracellular form of cyclophilin A (eCyPA) is secreted at high levels by bone marrow endothelial cells. In addition, eCyPA promotes migration and proliferation of multiple myeloma (MM) cells and effects homing of MM cells to the bone marrow by binding to the CD147 receptor on MM cells.

In one aspect, the invention relates to a method for identifying an agent for treating multiple myeloma (MM). The method comprises providing a first polypeptide comprising a CD147 polypeptide and a second polypeptide comprising an extracellular cyclophilin A (eCyPA) polypeptide sequence under conditions that allow for binding of the CD147 polypeptide and the eCyPA sequence. The complex is then contacted with a test agent. The method further includes determining whether the test agent disrupts binding of the first and second polypeptide. Disruption of binding of the first polypeptide and second polypeptide by the test agent indicates the test agent is a therapeutic agent for treating MM.

In another aspect, the invention relates to a method for identifying an agent for treating chronic lymphocytic leukemia (CLL) and lymphoplasmacytic lymphoma (LPL), the method comprising:
providing a first polypeptide comprising a CD147 polypeptide and a second polypeptide comprising an extracellular cyclophilin A (eCyPA) polypeptide sequence under conditions that allow for binding of the CD147 polypeptide and the eCyPA sequence;
contacting the complex with a test agent; and
determining whether the test agent disrupts binding of the first and second polypeptide, where the disruption of the binding of the first polypeptide and second polypeptide by the test agent indicates the test agent is a therapeutic agent for treating MM.

In a still further aspect, the invention relates to a method of determining a prognosis for a subject with multiple myeloma (MM), the method comprising:
providing a sample from a subject with MM;
assaying the sample to determine a level of eCyPA in the sample to obtain an eCyPA test value; and
comparing the eCyPA test value to an eCyPA reference value calculated for a sample whose MM status is known, where an eCyPA test value greater than a reference eCyPA value in a sample known not to have MM indicates that the subject has a poor prognosis, and where an eCyPA test value less than a reference eCyPA value in a sample known to have MM indicates that the subject has a good prognosis.

In yet another aspect, the invention relates to a method for determining efficacy of a multiple myeloma treatment in subject, the method comprising:
providing a sample from a subject with MM;
assaying the sample to determine a level of eCyPA in the sample to obtain an eCyPA test value; and
comparing the eCyPA test value to an eCyPA reference value calculated for a sample whose MM status is known; wherein
an eCyPA test value greater than a reference eCyPA value in a reference sample known not to have MM indicates that the treatment is not efficacious, and
an eCyPA test value less than a reference eCyPA value in a sample known to have MM indicates that the treatment is efficacious.

In another aspect, the invention relates to a method of diagnosing multiple myeloma (MM) or a multiple myeloma precursor condition in a subject, the method comprising:
providing a sample from a subject;
assaying the sample to determine a level of eCyPA in the sample to obtain an eCyPA test value; and
comparing the eCyPA test value to an eCyPA reference value calculated for a sample whose MM status is known, wherein
an eCyPA test value greater than a reference eCyPA value in a reference sample known not to have MM indicates that the subject has MM or a MM precursor conditions, and
an eCyPA test value equal to or less than a reference eCyPA value in a sample known to have MM indicates that the subject does not have multiple myeloma.

In a further aspect, the invention relates to a method of determining the progression of multiple myeloma (MM) in a subject, the method comprising:
providing a sample from a subject known to or suspected of having a multiple myeloma;
assaying the sample to determine a level of eCyPA in the sample to obtain an eCyPA test value; and
comparing the eCyPA test value to an eCyPA reference value calculated for a sample whose blood cancer stage is known,
wherein an eCyPA test value greater than a reference eCyPA value in a sample known not to have MM indicates that the subject has a MM more advanced than MM in subjects from which the reference eCyPA value is calculated, and
an eCyPA test value less than the reference eCyPA value indicates that the subject has a MM less advanced than MM in subjects from which the reference eCyPA value is calculated.

In another aspect, the invention relates to a method of preparing a therapeutic agent for treating multiple myeloma (MM) in a subject the method comprising:
providing a DNA encoding the variable domains of a donor CyPA antibody;

determining the amino acid sequence of the CDR regions of the donor monoclonal antibody from the DNA;

selecting human acceptor antibody sequences; and producing a humanized CyPA antibody comprising the CDRs from the donor antibody and variable region frameworks from the human acceptor antibody sequences.

In yet another aspect, the invention relates to a composition comprising a biocompatible substrate and bone marrow-derived endothelial cells (BMEC) admixed with a biocompatible substrate, where the BMEC cells express eCyPA in an amount sufficient to stimulate proliferation or migration of multiple myeloma (MM) cells.

The methods described herein can also be used to determine tumor burden in a patient with multiple myeloma. The inventors have discovered that CyPA serum levels are not only associated with MM progression, such as increasing level from MGUS, to SMM, to MM, but are also associated with tumor burden, such as decreasing level from MM to progressed (treated patients). Accordingly, CyPA can be used to monitor MM burden and progression in different stages of multiple myeloma progression, as well for indicating the amount of tumor burden remaining after treatment.

The invention additionally provides methods for identifying inhibitors of viral infections by inhibiting or otherwise reducing levels of intracellular and/or extracellular CyPA. Agents that reduce intracellular levels of CyPa can also be tested for their ability to reduce extracellular levels of CyPA. Similarly, agents that reduce extracellular levels of CyPa can also be tested for their ability to reduce intracellular levels of CyPA.

In another aspect, the invention relates to a method for identifying an agent for inhibiting viral infections. The method includes providing a cyclophilin A (CyPA) polypeptide sequence;

contacting the complex with a test agent; and determining whether the test agent binds to the CyPA polypeptide sequence, wherein binding of the test agent to CyPA indicates the test agent is an inhibitor of viral infection.

In some embodiments, the CyPA is provided external to a cell, for example, as a secreted polypeptide from a cell expressing CyPA. In other embodiments, the CyPA is provided in a cell.

In some embodiments, the method further includes determining whether binding of the test agent to CyPA lowers CyPA, e.g., in a cell free bodily fluid such as serum, where it may be present as an extracellular secreted polypeptide.

The invention additionally provides methods for identifying inhibitors of viral infections by inhibiting or otherwise reducing levels of intracellular and/or extracellular CyPA. The method includes providing a cyclophilin A (CyPA) polypeptide sequence; contacting the complex with a test agent; and determining whether the test agent blocks interactions between the CyPA polypeptide sequence and a CD147 polypeptide. Blocking or otherwise disrupting the interaction between CyPA and the CD147 polypeptide indicates the test agent is an inhibitor of viral infection or a therapeutic agent for treating MM. The CD147 polypeptide can be provided on the surface of a cell or in a cell-free solution or substrate.

If desired, the test agent can be screened for its ability to lower amounts of or otherwise inhibit both intracellular and extracellular CyPA polypeptide levels. Among the advantages of the invention is that it provides convenient and relatively non-invasive tests for diagnosing, staging, or determining the prognosis of, or otherwise assessing multiple myeloma in a patient. The assays can be performed using a peripheral blood sample without the need to make an incision.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention are apparent from the following description of the invention, and from the claims.

BRIEF DESCRIPTION OF THE DRAWINGS

Some of the figures in the application were executed in color.

FIG. 11.

FIG. 12.

FIG. 14.

FIG. 15.

FIG. 16. (FIG. 16C) Flow cytometry of CD147 (red line) and control isotype (black line) expression in one CLL cell line (HG3) and one primary tumor patient cells (CLLPT #1). (FIG. 16D) Flow cytometry of CD147 (red line) and control isotype (black line) expression in one LPL cell line (BCWM.1) and one primary tumor patient cells (LPLPT #1).

DETAILED DESCRIPTION OF THE INVENTION

Figure 1A:
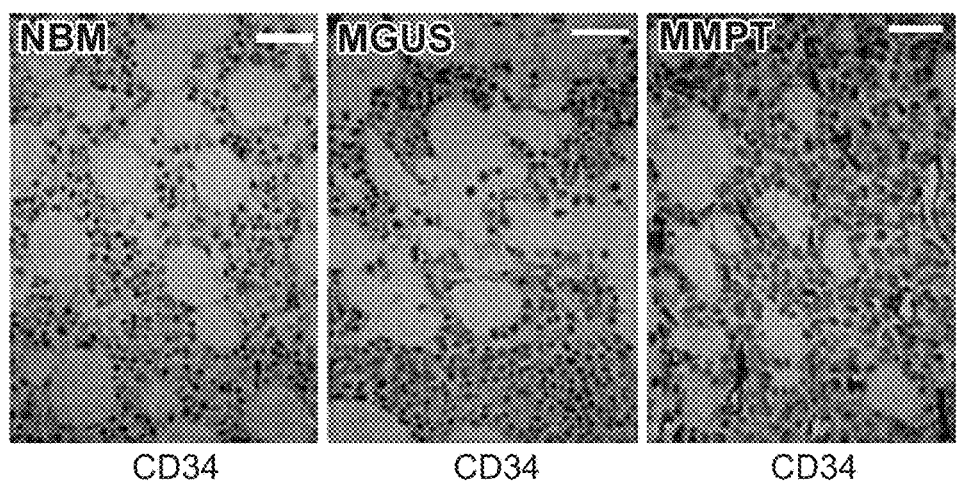
(FIG. 1A) Representative CD34 immunostains in BM biopsies from normal individuals (NBM) (n=20) as well as MGUS (n=20) and MM patients (MMPT) (n=60).

Metastasis of epithelial tumors is a complex and poorly understood molecular, cellular, and organismal multistage process. Sometimes termed the invasion-metastasis cascade, it occurs when cancer cells spread from the site of origin to anatomically distant organs. The process is driven by acquisition of genetic and/or epigenetic alterations within the tumor cells themselves (the 'seeds'), and by multistep interplay of these cells with the host microenvironment (the 'soil'), culminating in colonization in a foreign organ. Akin to certain epithelial neoplasms (e.g., prostate and breast carcinomas) that frequently metastasize and colonize to the bone marrow (BM), B-cell lymphoid malignancies such as multiple myeloma (MM), chronic lymphocytic lymphoma (CLL), and lymphoplasmacytic lymphoma (LPL), preferentially colonize and accumulate within the BM. Although the molecular mechanisms responsible for this preferential colonization are still not completely understood, pathogenetic studies indicate that the BM-microenvironment (BM-ME), comprised of an extracellular matrix and diverse cellular elements (e.g. stromal, adiposal, endothelial, and hematopoietic), plays a pivotal role. As with the BM homing of hematopoietic stem cell cells (HSCs), migration of MM and other B-cell malignancies from the PB to the BM niche is not a passive process, but rather is a complex active process requiring multiple adhesion and chemokine receptors. BM homing of HSCs involves tethering of the cells by E- and P-selectins, associated with P-selectin glycoprotein ligand-1 and CD44 on the cells. This tethering involves interaction of endothelial cells with circulating HSCs, and leads to rolling of the HSCs along the endothelium and activation of the SDF-1/CXCR4 axis, followed by VLA-/VCAM-1 activation. Other molecules that appear to play a role in HSCs homing include LFA-1, VLA-5, and activated metalloproteases MMP2/9.

Here we have used MM as a prototypical terminally differentiated B-cell neoplasm to investigate the cellular and molecular BM-ME properties involved in BM colonization. MM is a fatal hematological malignancy of terminally differentiated, post-germinal B-cells that originate in the lymph nodes and accumulate in the BM during disease evolution. Reciprocal interactions between MM cells and the BM-ME not only mediate their growth, but also protect them from apoptosis, resulting in the bone lytic lesions and BM angiogenesis. Interestingly, however, at the end-stage of disease MM cells are able to survive and proliferate even in the absence of the BM-ME. During this stage the number of MM cells circulating in the PB increases, and growth outside the BM can occur. Similarly to the HSC, factors implicated in BM homing of MM include the CXCR4/SDF-1 axis, IGF-1, and intracellular regulators downstream of CXCR4, including Rho and Rac. Of these factors, the CXCR4/SDF-1 axis plays an especially critical role in regulating migration and adhesion of MM cells.

Among the interactions between MM cells and the BM-ME, intimate physical contact with BMECs is a major feature and is most readily discerned during early disease stages, when the tumor burden is low. Clinico-pathologic correlations which highlight the importance of the functional interactions between MM cells and BMECs include the following: (1) BM angiogenesis is associated with MM cell growth, disease progression, and patient survival; (2) progression of monoclonal gammopathy of undetermined significance (MGUS), to active MM is associated with increasing angiogenesis; and (3) microvascular density correlates with disease stage and is a prognostic factor in newly diagnosed MM patients receiving conventional and high-dose chemotherapy.

Although several pro-angiogenic molecules secreted by MM cells have been identified (e.g. VEGF, βFGF, and HGF), the signaling molecules secreted by BMECs, which that promote MM disease progression and BM homing are not fully known.

We have investigated the role of BMECs in the colonization of MM cells to the BM niche. Having previously observed high BCL9 expression in BMECs, but not other BM cells, we chose to focus on the role of this transcriptional co-activator of the canonical Wnt/β-catenin pathway. We used an integrated approach combining in vitro assays with in vivo migration assays that simulate the human-human heterotypic interactions between MM and BM cells. Additionally, we performed proteomic analysis of signaling molecules secreted by BMECs, as well as shRNA-based loss-of-function assays, to identify and functionally validate eCyPA as a novel transcriptional target of the Wnt/β-catenin/BCL9 complex. eCyPA is secreted by BMECs and promotes pleiotropic signaling changes that enhance not only migration of MM cells toward the BM, but also proliferation mediated by binding to CD147 receptors on the MM cells. A comparison between BMECs and BMSCs from the same MM patient demonstrated that these cells play different roles in the migration and BM colonization of MM cells. In contrast to primary BMECs, primary BMSCs secrete very little eCyPA but instead secrete SDF-1, thereby promoting migration and BM homing of MM cells, less efficiently than primary BMECs. Consistent with this finding, BMEC-induced migration of MM cells was inhibited by a CD147 Ab, but not by a CXCR4 Ab. In addition, inhibition of the eCyPA/CD17 axis supressed migration, tumor growth, and BM-colonization in a mouse xenograt model of MM. Furthermore, we have documented that eCyPA promotes migration of CLL and LPL cells, two other B-cell malignancies that colonize the BM and express CD147. Taken together, our findings indicate that cells within the BM microenvironment play different roles in MM progression, and offer a potential link between chronic inflammation, immunomodulation, and the pathogenesis of MM, CLL and LPL. Moreover, our results provide a compelling rationale for exploring the role of eCyPA and CD147 as markers of disease progression and for the development of novel therapeutic approaches based on targeting the eCyPA/CD147 signaling complex.

Screening for Therapeutic Agents for Treating a Hematological Malignancy

Provided by the invention are methods for identifying therapeutic agents for treating multiple myeloma or another hematological malignancy that are based on the binding of cyclophilin A to CD147 on multiple myeloma cells.

For example, a method for identifying an agent for treating multiple myeloma (MM) or other hematological malignancies includes providing a first polypeptide comprising a CD147 polypeptide and a second polypeptide comprising an extracellular cyclophilin A (eCyPA) polypeptide sequence under conditions that allow for binding of the CD147 polypeptide and the eCyPA sequence to form a complex. The complex is then contacted with a test agent, and the complex is assayed to determine whether the test agent disrupts binding of the first and second polypeptide. Disruption of the binding of the first polypeptide and second polypeptide by the test agent indicates the test agent is a potential therapeutic agent for treating MM.

A test agent that disrupts CD147 binding to eCyPA can be further characterized to determine its suitability as a therapeutic agent for treating MM. For example, a promising test agent can be used as described in the examples below to determine whether it inhibits proliferation of an MM cell population and/or whether it inhibits migration of MM cells into bone marrow Inhibition of MM cell proliferation and/or migration indicates the test agent is a therapeutic agent for treating MM.

The first and second polypeptide sequences can be CD147 polypeptide sequences and cyclophilin A sequences known in the art. Thus, in some embodiments, extracellular cyclophilin A polypeptide sequences include the following amino acid sequence:

TABLE-US-00001

(SEQ ID NO: 1)
GGSMVNPTVFFDIAVDGEPLGRVSFELFADKVPKTAENFRALSTGEKGFG

YKGSCFHRIIPGFMCQGGDFTRHNGTGGKSIYGEKFEDENILKHTGPGIL

SMANAGPNTNGSQFFICTAKTEWLDGKVVFGKVKEGMNIVEAMERFGSRN

GKTSKKITIADCGQLE

In some embodiments the CD147 polypeptide sequences include a polypeptide with the following amino acid sequence of a human CD147 polypeptide:

TABLE-US-00002

(SEQ ID NO: 2)
MAAALFVLLGFALLGTHGASGAAGFVQAPLSQQRWVGGSVELHCEAVGSP

VPEIQWWFEGQGPNDTCSQLWDGARLDRVHIHATYHQHAASTISIDTLVE

EDTGTYECRASNDPDRNHLTRAPRVKWVRAQAVVLVLEPGTVFTTVEDLG

SKILLTCSLNDSATEVTGHRWLKGGVVLKEDALPGQKTEFKVDSDDQWGE

YSCVFLPEPMGTANIQLHGPPRVKAVKSSEHINEGETAMLVCKSESVPPV

TDWAWYKITDSEDKALMNGSESRFFVSSSQGRSELHIENLNMEADPGQYR

CNGTSSKGSDQAIITLRVRSHLAALWPFLGIVAEVLVLVTIIFIYEKRRK

PEDVLDDDDAGSAPLKSSGQHQNDKGKNVRQRNSS

Test Agents

The term "test agent" or "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of disregulation of apoptosis in a cell or tissue). Test agents comprise both known and potential therapeutic compounds. A test compound can be determined to be therapeutic by using the screening methods of the present invention.

A "known therapeutic compound" refers to a therapeutic compound that has been shown (e.g., through animal trials or prior experience with administration to humans) to be effective in such treatment or prevention.

The screening methods can include those known or used in the art or those first described herein. For example, in one embodiment a CD147 is immobilized on a microtiter plate and incubated with cyclophilin A in the presence of a test agent. Subsequently, the complex can be detected using a secondary antibody, and absorbance can be detected on a plate reader.

The test agent can be a small molecule or a large molecule. A "small molecule" as used herein, is meant to refer to a composition that has a molecular weight of less than about 5 kD and most preferably less than about 4 kD. Small molecules can be, e.g., nucleic acids, peptides, polypeptides, peptidomimetics carbohydrates, lipids or other organic or inorganic molecules. Libraries of chemical and/or biological mixtures, such as fungal, bacterial, or algal extracts, are known in the art and can be screened with any of the assays of the invention. Examples of methods for the synthesis of molecular libraries can be found in the art, for example in: DeWitt, et al., 1993. Proc. Natl. Acad. Sci. U.S.A. 90: 6909;

Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

The test agent need not be any particular structure or size. In some embodiments, the test agent is a nucleic acid, a polypeptide, a small molecule or combinations thereof, an inhibitory nucleic acid, e.g., a triplex forming oligonucleotide, an aptamer, a ribozyme, an antisense RNA, a short interfering RNA (siRNA), or a micro-RNA (miRNA).

In some embodiments, the polypeptide is a polypeptide binding partner of a cyclophilin A molecule or CD147 molecule, e.g., an antibody, e.g., an anti-CyPA antibody. Anti-CyPA antibodies for treating HIV infection are described in, e.g., U.S. Pat. No. 5,840,305.

Antibodies are preferably modified to reduce the likelihood of an unwanted host reaction. One example of such a modification is a humanized antibody. Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., Nature, 321:522-525 (1986); Riechmann et al., Nature 332:323-327 (1988); Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using other techniques known in the art, including phage display libraries (Hoogenboom and Winter, J. Mol. Biol., 227:381 (1991); Marks et al., J. Mol. Biol., 222:581 (1991)). The techniques of Cole and Boerner are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

In addition, cyclophilin A antibodies and anti-CD147 antibodies can be used to create a therapeutic agent for treating MM, or another disease by adapting methods for making humanized antibodies described in U.S. Pat. No. 8,673,593. The method includes providing a DNA encoding the variable domains of a donor CyPA antibody and determining the amino acid sequence of the CDR regions of the donor monoclonal antibody from the DNA, selecting human acceptor antibody sequences; and producing a humanized CyPA antibody comprising the CDRs from the donor antibody and variable region frameworks from the human acceptor antibody sequences. If desired, the method can further include determining whether humanized antibody disrupts binding of first polypeptide comprising a CD147 polypeptide and a second polypeptide comprising an extracellular cyclophilin A (eCyPA) polypeptide sequence under conditions that allow for binding of the CD147 polypeptide and the eCyPA sequence. Disruption of the binding of the first polypeptide and second polypeptide by the humanized antibody indicates it is a therapeutic agent for treating MM.

The antibody preferably binds specifically (or selectively) to either a cyclophilin A or CD147 molecule. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

If desired, the antibody can be provided conjugated or coupled to a detectable label, a radioactive label, an enzyme, a fluorescent label, a luminescent label, a bioluminescent label, or a therapeutic agent.

Detecting eCyPA and CD147 Complexes

The first and second polypeptide can be provided in either a cell-free or a cell-based system. Art recognized methods for measuring protein-protein interactions can be used to characterize binding of the eCyPA sequence and CD147 polypeptide in the presence of the test agent, for example, by coupling the test agent with a radioisotope or enzymatic label such that binding of the test compound to the antigen or biologically-active portion thereof can be determined by detecting the labeled compound in a complex. For example, test agents can be labeled with $^{125}I$, $^{35}S$, $^{14}C$, or $^{3}H$, either directly or indirectly, and the radioisotope detected by direct counting of radioemission or by scintillation counting. Alternatively, test agents can be enzymatically-labeled with, for example, horseradish peroxidase, alkaline phosphatase, or luciferase, and the enzymatic label detected by determination of conversion of an appropriate substrate to product.

In one embodiment, the assay comprises contacting eCyPA sequence-CD147 polypeptide complex with a test agent, and determining the ability of the test compound to interact with the complex or otherwise disrupt the existing complex. In this embodiment, determining the ability of the test compound comprises determining the ability of the test compound to preferentially bind to the eCyPA sequence and/or the CD147 or a biologically-active portion thereof, as compared to its binding partner.

Observation of the complex in the presence and absence of a test agent can be accomplished in any vessel suitable for containing the reactants. Examples of such vessels include microtiter plates, test tubes, and micro-centrifuge tubes. In one embodiment, a fusion protein that adds a domain that allows one or both of the proteins to be bound to a matrix can be provided. In one embodiment, GST-antibody fusion proteins or GST-antigen fusion proteins are adsorbed onto glutathione Sepharose® beads (Sigma Chemical, St. Louis, Mo.) or glutathione-derivatized microtiter plates, that are then combined with the test compound, and the mixture is incubated under conditions conducive to complex formation (e.g., at physiological conditions for salt and pH).

Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

In some embodiments, one of either the eCyPA sequence or the CD147 sequence is immobilized to facilitate separation of complexed from uncomplexed forms of one or both following introduction of the rest agent, as well as to accommodate automation of the assay. If desired, either member of the putative complex can be immobilized utilizing biotin and streptavidin. Biotinylated antibody or antigen molecules can be prepared from biotin-NHS (N-hydroxysuccinimide) using techniques well-known in the art (e.g., biotinylation kit, Pierce Chemicals, Rockford, Ill.), and immobilized in the wells of streptavidin-coated 96 well plates (Pierce Chemical). Methods for detecting such complexes, in addition to those described above for the GST-immobilized complexes, include immunodetection of complexes using such other antibodies reactive with the antibody or antigen.

In some embodiments, binding of the test agent to the complex is detected using assay AlphaScreen® technology (PerkinElmer, Waltham, Mass.).

Cells Used in Screening Assays

When cell-based assays are used, CD-147 expressing cells can be provided by any cell (e.g., MM1 S, OPM1, H929, U266 cells) that expresses CD147 in amounts sufficient to detectably bind an eCyPA polypeptide or CD147-binding fragment of an eCyPA polypeptide. Cells can be prokaryotic or eukaryotic cells. The cell can be provided in vitro or in vivo. Cells can be prokaryotic or eukaryotic, for example, mammalian cells including both human and non-human mammalian cells (e.g., a rodent such as a mouse or rat cell).

Cells can be primary cells or established cell lines. In some embodiments hematopoietic cells are used. The term "hemapoietic cells" as used herein includes all blood cell types, including those from the myeloid lineage (monocytes and macrophages, neutrophils, basophils, eosinophils, erythrocytes, megakaryocytes/platelets, dendritic cells), and lymphoid lineages (T-cells, B-cells, NK-cells).

In some embodiments, the methods described herein are performed on cell samples. A "sample" in the context of screening assays is understood within the scope of the invention to refer to a suitable cell, group of cells, animal model or human. These samples do not have to be derived from a subject. A sample in this context can be a group of cells from a cell line. Preferably cell lines are derived from a hematopoietic disorder. A non-limiting list of samples includes bone marrow aspirates or bone marrow biopsy (for myeloma, leukemias and other hematopoietic disorders), lymph node samples lymphomas and other hematopoietic disorders) and peripheral blood samples (for leukemias and other hematopoietic disorders). The sample may be of a particular type of hematopoietic cell, for example a population of B lymphocytes and/or T lymphocytes.

The presence and/or level of proteins used in the methods described herein (e.g., eCyPA protein and CD147 polypeptides) can be evaluated using methods known in the art, e.g., using quantitative immunoassay methods such as enzyme linked immunosorbent assays (ELISA), see above, immunoprecipitations, immunofluorescence, enzyme immunoassay (EIA), radioimmunoassay (RIA), and Western blot analysis.

Similarly, the presence and/or level of transcripts encoding these proteins can be evaluated using RNA detection methods known in the art, e.g., quantitative transcription detection such as a transcription-based amplification system (TAS). Some examples of RNA detection systems include PCR and QRT-PCR-based amplification systems, ligase chain reaction, QP, replicase, reverse transcriptase-coupled nucleic acid sequence-based amplification (NASBA), self-sustained sequence replication (3 SR), strand displacement amplification (SDA), or reverse transcriptase-coupled rolling circle amplification (RCA).

Diagnosing and Determining a Prognosis for a Subject with Multiple Myeloma

The link identified by the inventors between eCyPA and multiple myeloma also provides new methods for diagnosing and otherwise assessing MM in a subject. Multiple myeloma (MM) or a multiple myeloma precursor condition in a subject can be diagnosed by providing a sample from a subject and assaying the sample to determine a level of eCyPA in the sample to obtain an eCyPA test value. The test value is compared to an eCyPA reference value calculated for a sample whose MM status is known. An eCyPA test value greater than a reference eCyPA value in a reference sample known not to have MM indicates that the subject has MM or a MM precursor conditions. Conversely, an eCyPA test value equal to or less than a reference eCyPA value in a sample known to have MM indicates that the subject does not have multiple myeloma.

Similarly, the prognosis for a subject with multiple myeloma (MM) can be determined by providing a sample from a subject with MM and assaying the sample to determine a level of eCyPA in the sample to obtain an eCyPA test value, then comparing the eCyPA test value to an eCyPA reference value calculated for a sample whose MM status is known. An eCyPA test value greater than a reference eCyPA value in a sample known not to have MM indicates that the subject has a poor prognosis, while an eCyPA test value less than a reference eCyPA value in a sample known to have MM indicates that the subject has a good prognosis.

Efficaciousness of a treatment for multiple myeloma can be determined by providing a sample from a subject with MM and assaying the sample to determine a level of eCyPA in the sample to obtain an eCyPA test value. The eCyPA test value is compared to an eCyPA reference value calculated for a sample whose MM status is known. An eCyPA test value greater than a reference eCyPA value in a reference sample known not to have MM indicates that the treatment is not efficacious, and an eCyPA test value less than a reference eCyPA value in a sample known to have MM indicates that the treatment is efficacious. In some embodiments, the reference sample is obtained from the same subject prior to beginning treatment of MM or at an earlier point in treatment of MM.

The progression of multiple myeloma (MM) in a subject can similarly be determined; an eCyPA test value greater than a reference eCyPA value in a sample known not to have MM indicates that the subject has a MM more advanced than MM in subjects from which the reference eCyPA value is calculated, while an eCyPA test value less than the reference eCyPA value indicates that the subject has a MM less advanced than MM in subjects from which the reference eCyPA value is calculated.

The threshold for determining how a test sample is scored in the assays described herein, e.g., whether a test sample is scored positive, can be altered depending on the sensitivity or specificity desired. The clinical parameters of sensitivity, specificity, negative predictive value, positive predictive value and efficiency are typically calculated using true positives, false positives, false negatives and true negatives. A "true positive" sample is a sample that is positive according to an art recognized method, which is also diagnosed as positive (high risk for early attack) according to a method of the invention. A "false positive" sample is a sample negative by an art-recognized method, which is diagnosed positive (high risk for early attack) according to a method of the invention. Similarly, a "false negative" is a sample positive for an art-recognized analysis, which is diagnosed negative according to a method of the invention. A "true negative" is a sample negative for the assessed trait by an art-recognized method, and also negative according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of the measured trait. Sensitivity is calculated as the number of true positive results divided by the sum of the true positives and false negatives. Sensitivity essentially is a measure of how well a method correctly identifies those with disease. For example, cut-off values can be selected such that the sensitivity of diagnosing an individual is at least about 60%, and can be, for example, at least about 50%, 65%, 70%, 75%, 80%, 85%, 90% or 95%.

As used herein, the term "specificity" means the probability that a method is negative in the absence of the measured trait. Specificity is calculated as the number of true negative results divided by the sum of the true negatives and false positives. Specificity essentially is a measure of how well a method excludes those who do not have the measured trait. For example, cutoff values can be selected so that when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having the measured trait actually has the disease. Positive predictive value can be calculated as the number of true positives divided by the sum of the true positives and false positives. Positive predictive value is determined by the characteristics of the diagnostic method as well as the prevalence of the disease in the population analyzed. The cut-off values can be selected such that the positive predictive value of the method in a population having a disease prevalence of 15% is at least about 5%, and can be, for example, at least about 8%, 10%, 15%, 20%, 25%, 30% or 40%.

As used herein, the term "efficiency" means the accuracy with which a method diagnoses a disease state. Efficiency is calculated as the sum of the true positives and true negatives divided by the total number of sample results, and is affected by the prevalence of the trait in the population analyzed. The cut-off values can be selected such that the efficiency of a method of the invention in a patient population having a prevalence of 15% is at least about 45%, and can be, for example, at least about 50%, 55% or 60%.

For determination of the cut-off level, receiver operating characteristic (ROC) curve analysis can be used. In some embodiments, the cut-off value for the classifier can be determined as the value that provides specificity of at least 90%, at least 80% or at least 70%.

Treating Subjects with High Levels of eCyPA

Subjects determined to have multiple myeloma, a multiple myeloma related condition, or inflammation based on elevated levels of eCyPA can be treated using one or more treatment modalities known in the art. For example, treatment multiple myeloma, a multiple myeloma related condition can be with a chemotherapeutic agent, radiation agent, hormonal agent, biological agent, an anti-inflammatory agent, or a combination of two or more of these agents.

Chemotherapeutic agents include, e.g., sanglifehrin A, sarcosine-3(4-methylbenzoate) (SmBz), voclosporin, cyclosporin A, NVP018, alisporivir, NIM811, MMM284, CD147 antibody, CyPA antibody, tamoxifen, trastuzamab, raloxifene, doxorubicin, fluorouracil/5-fu, pamidronate disodium, anastrozole, exemestane, cyclophosphamide, epirubicin, letrozole, toremifene, fulvestrant, fluoxymester one, trastuzumab, methotrexate, megastrol acetate, docetaxel, paclitaxel, testolactone, aziridine, vinblastine, capecitabine, goselerin acetate, zoledronic acid, taxol, vincristine, and/or HDAC/TDAC inhibitors and aggresome inhibitors disclosed in U.S. Pat. No. 8,999,289. Additional treatment strategies include, e.g., autologous stem cell transplantation and allogeneic effector cell transplantation, to develop an effective treatment strategy based on the stage of myeloma being treated (see, e.g., Multiple Myeloma Research Foundation, Multiple Myeloma: Stem Cell Transplantation 1-30 (2004); U.S. Pat. Nos. 6,143,292, and 5,928,639, Igarashi, et al.

Blood 2004, 104(1): 170-177, Maloney, et al. 2003, Blood, 102(9): 3447-3454, Badros, et al. 2002, J. Clin. Oncol., 20:1295-1303, Tricot, et al. 1996, Blood, 87(3):1196-1198; the contents of which are incorporated herein by reference).

The effectiveness of a multiple myeloma diagnosis or prognosis using eCyPa levels can be compared to other methods known in the art for assessing multiple myeloma or a related condition. The multiple myeloma staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value <2.0 mg/dL) and B (abnormal renal function, creatinine value.gtoreq.2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta.sub.2-microglobulin ($\beta_2$-M) and albumin, which separates patients into three prognostic groups irrespective of type of therapy.

Administration of the pharmaceutical compositions at selected dosage ranges and routes typically elicits a beneficial response as defined by the European Group for Blood and Marrow transplantation (EBMT) in Table 1, below (taken from U.S. Pat. No. 8,632,772).

| EBMT/IBMTR/ABMTR[1] Criteria for Response | |
|---|---|
| Complete Response | No M-protein detected in serum or urine by immunofixation for a minimum of 6 weeks and fewer than 5% plasma cells in bone marrow |
| Partial Response | >50% reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/ or >25% increase in bone marrow plasma cells (at least 10% in absolute terms)[2] |
| Relapse | Reappearance of disease in patients previously in complete response, including detection of paraprotein by immunofixatian |

[1]EBMT: European Group for Blood and Marrow transplantation; IBMTR: International Bone Marrow Transplant Registry; ABMTR: Autologous Blood and Marrow Transplant Registry.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the composition elicits a response in an individual clinically manifesting at least one symptom associated with MM, depends in part, on the severity of disease, e.g., Stage I, II, or III, and in part, on whether the patient is newly diagnosed or has late stage refractory MM. Thus, in some embodiments, administration of the pharmaceutical composition elicits a complete response.

In some embodiments, administration of the pharmaceutical composition elicits a very good partial response or a partial response. In other embodiments, administration of the pharmaceutical composition elicits a minimal response. In other embodiments, administration of the pharmaceutical composition prevents the disease from progressing, resulting in a response classified as "no change" or "plateau" by the EBMT.

Computer Implemented Embodiments

Information from the eCyPA levels and other test results can implemented in computer programs executed on programmable computers that include, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

In some embodiments, the a machine-readable storage medium can comprise a data storage material encoded with machine readable data or data arrays which, when using a machine programmed with instructions for using the data, is capable of use for a variety of purposes, such as, without limitation, subject information relating to a diagnosing a type or subtype of ovarian cancer, evaluating the effectiveness of a treatment (e.g., surgery or chemotherapy).

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein.

The health-related data management system of the invention may also be considered to be implemented as a computer-readable storage medium, configured with a computer program, where the storage medium so configured causes a computer to operate in a specific and predefined manner to perform various functions described herein.

Bone Marrow Scaffolding Substrates

Also provided by the invention is a composition that includes a biocompatible substrate and bone marrow-derived endothelial cells (BMEC) admixed with a biocompatible substrate. The BMEC cells express eCyPA in an amount sufficient to stimulate proliferation or migration of multiple myeloma (MM) cells. In some embodiments, the substrate is a poly-caprolactone scaffolding (PCLS). To admix the BMEC with a biocompatible substrate, the PCLS is precoated with fibronectin.

Other Malignancies and Conditions

While illustrated with multiple myeloma cells, the methods and compositions described herein can be adapted for any malignancy in which increased cyclophilin A levels or activity promotes proliferation and/or migration of malignant cells to bone marrow, and/or is associated with CD147 expression. This includes chronic lymphocytic leukemia (CLL) and lymphoplasmacytic lymphoma (LPL) (see examples below showing eCyPA affects these cells in ways similar to its effects on MM cells).

Additional conditions include precursor conditions or other conditions related to MM, such as Monoclonal Gammopathy of Undetermined Significance (MGUS), smoldering myeloma, asymptomatic MM, and symptomatic MM, ranging from newly diagnosed to late stage relapsed/refractory.

Additional non-limiting examples of hematopoietic cancers for which methods of the invention can be used include leukemias (myeloid and lymphoid types), and lymphomas of B- and T-cell lineages), polycythermis vera and other myeloproliferative diseases. Examples of leukemias include acute lymphoblastic leukemia (ALL), adult T cell leukemia (ATL), acute myeloblastic leukemia (AML) and chronic myeloid leukemia (CML). The method can also be used to treat carcinomas that frequently metastasize to the bone marrow such as breast and prostate cancers.

In addition, the methods disclosed herein are useful in treating inflammation generally. The screening methods are useful for identifying new therapeutic agents for treating inflammation. Similarly, the methods discussed above can be used in diagnosing, prognosis, efficaciousness and assessing the progression of inflammation in a subject.

The invention will be further illustrated in the following non-limiting examples. The examples show that B-cell malignancies frequently colonize the bone marrow (BM). New insights into the pathogenesis of these malignancies suggest that cells in the BM microenvironment play a critical role. Using multiple myeloma (MM) as a model of a terminally differentiated B-cell neoplasm that selectively colonizes the BM, and taking advantage of a broadly adaptable mouse xenograft model system employing bone-like scaffolds coated with human BM-derived cells, we demonstrated that BM-derived endothelial cells (BMECs), but not BM-derived stromal cells (BMSCs), secrete cyclophilin A (eCyPA), an extracellular pleiotropic signaling factor that promotes migration, growth, and BM colonization of MM cells via binding to its cognate receptor, CD147, on MM cells. The clinical/translational implications of this work are highlighted by the observation of significantly higher eCyPA levels in BM serum than in peripheral blood (PB) of the same MM patient, and that blockade of the eCyPA/CD17 axis supresses BM-homing and tumor growth in a mouse xenograft model of MM. Furthermore, eCyPA also promotes cell migration in chronic lymphocytic lymphoma and lymphoplasmacytic lymphoma, two other B-cell malignancies that colonize the BM and express CD147. Taken together, these findings provide evidence of a possible link between chronic inflammation, immune dysregulation, and the pathogenesis of these B-cell malignancies. Importantly, our findings also offer a compelling rationale for targeting the eCPA/CD147 signaling complex as a novel treatment approach for these malignancies.

Figure 14A:
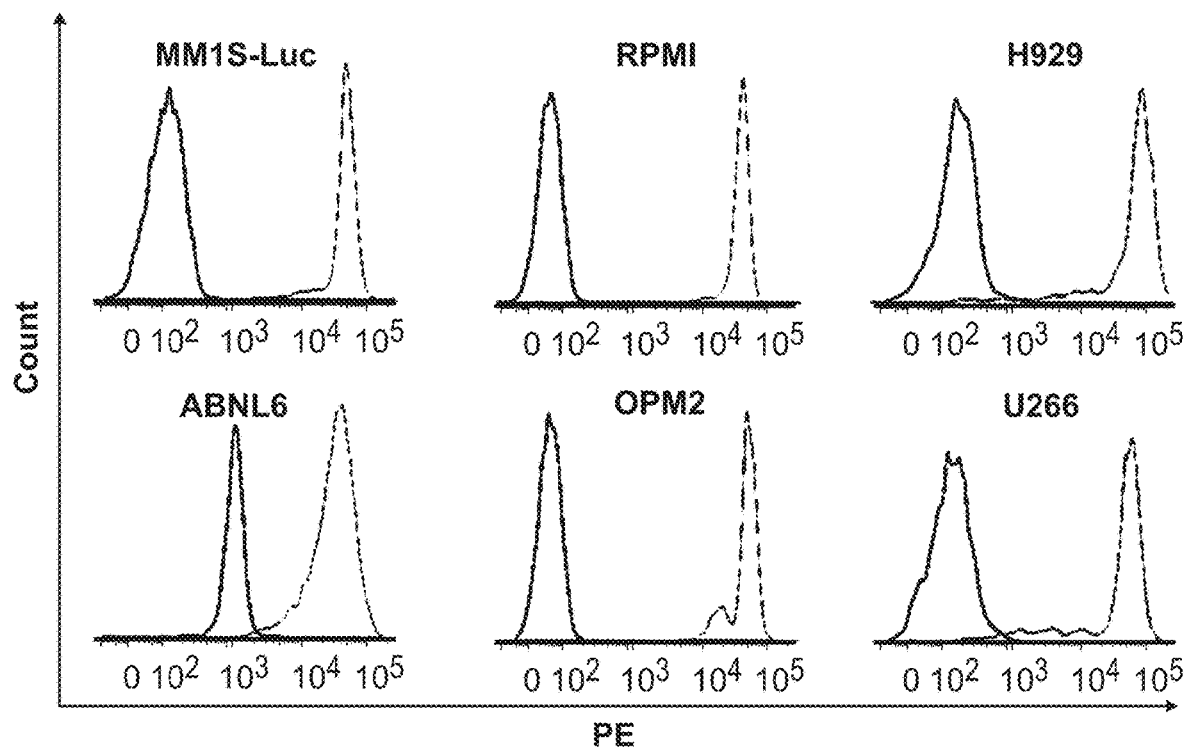
(FIG. 14A) Flow cytometry of CD147 (red line) and control isotype (black line) expression in six different MM cell lines.
Figure 14B:
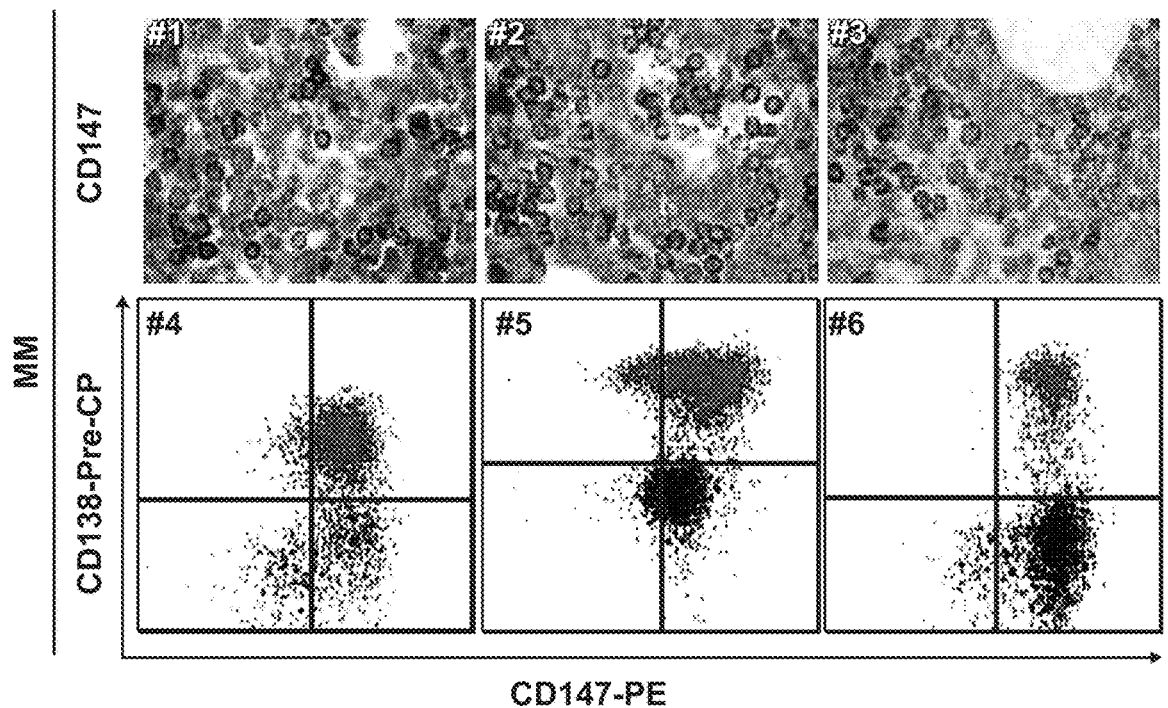
(FIG. 14B) Top: CD147 immunostain in three representative cases of BM biopsies from MM patients (n=60). Bottom: flow cytometry of CD147 in MM cells from three representative BM aspirates from MM patients (n=10).
Figure 14C:
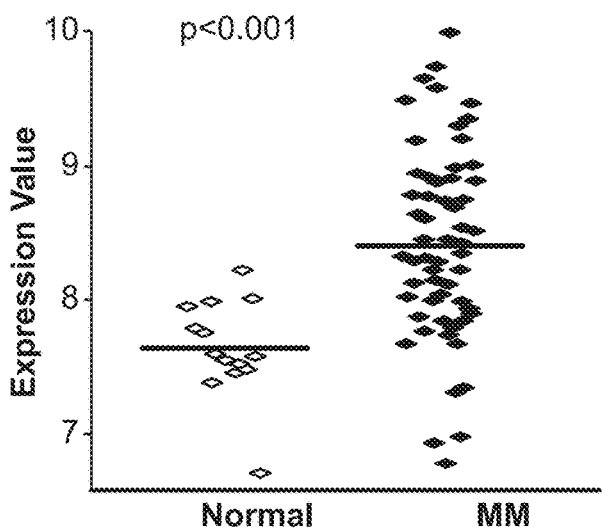
(FIG. 14C) mRNA expression of CD147 (GSE6477) in BM plasma cells from a normal subjects (12) and MM patients (n=60).
Figure 14D:
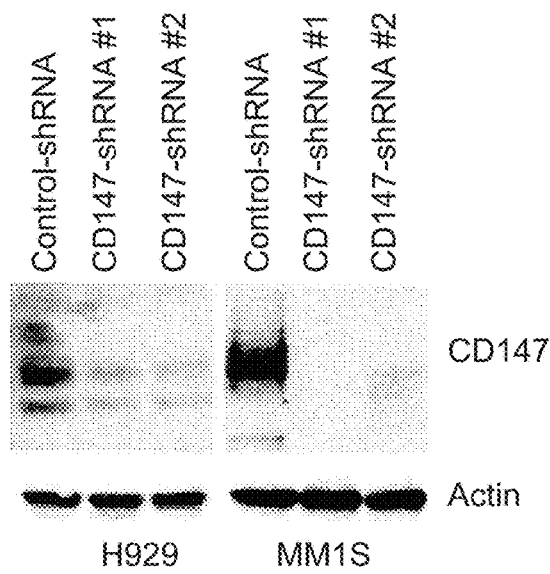
(FIG. 14D) Immunoblots of CD147 in total protein extracts from H929 and MM1S cells lentivirally transduced with control-shRNA or CD147-shRNA.
Figure 14E:
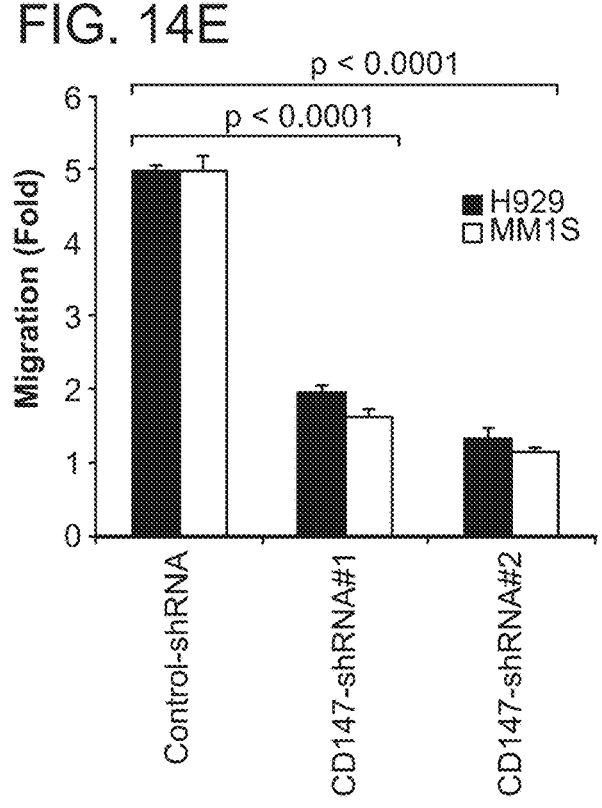
(FIG. 14E) Transwell migration assay of H929 and MM1S cell co-cultured with BMEC-60 cells lentivirally transduced with control-shRNA or CD147-shRNA.
Figure 14F:
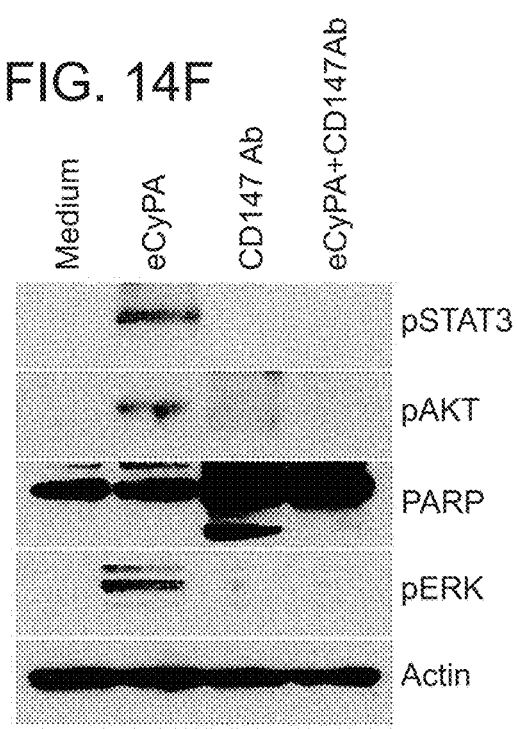
(FIG. 14F) Immunoblot analysis of pSTAT, pAKT, pERK and PARP in MM1S cells incubated with medium alone, 50 ng/ml of recombinant eCyPA, 100 ug/ml of CD147 Ab, or 50 ng/ml of recombinant eCyPA plus 100 ug/ml of CD147 Ab.
Figure 14G:
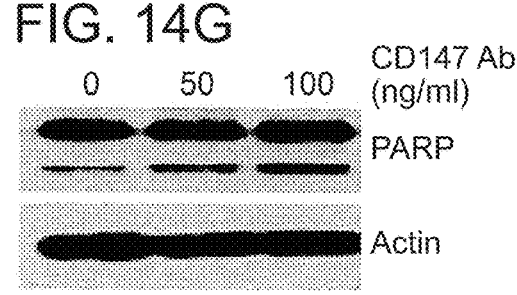
(FIG. 14G) Immunoblot analysis of total protein extracts from MM1S cells incubated with two different concentrations of CD147 Ab.
Figure 14H:
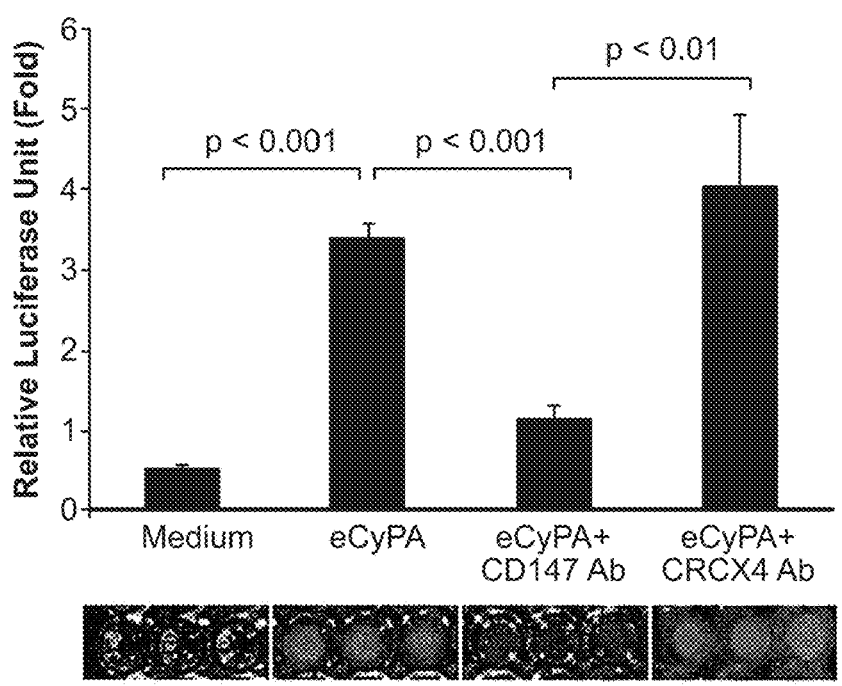
(FIG. 14H) Transell migration assay of MM1 S-luc cells incubated with medium alone, or 50 ng/ml of recombinant eCyPA, or a combination of either 50 ng/ml of recombinant CyPA plus 100 ug/ml of CD147 Ab or 50 ng/ml or recombinant CyPA plus 100 ug/ml of CXCR4 Ab.
Figure 14I:
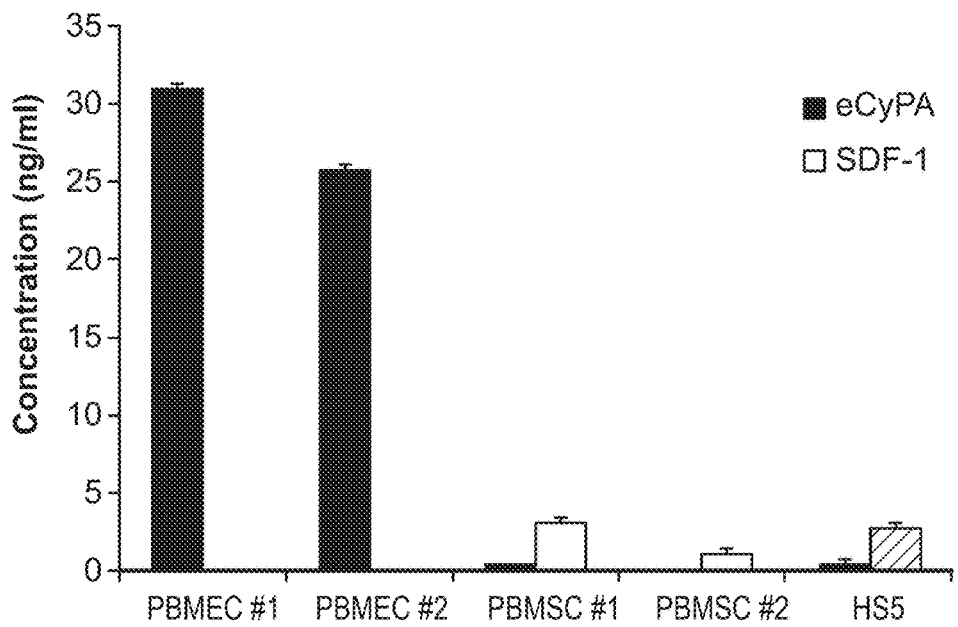
(FIG. 14I) ELISA assay of CyPA and SDF-1 in CM from the indicated primary cells. 5.times.10.sup.5 cell were plated for each cell and incubated for 72 hrs. Results are means.+−. SD for assays performed in triplicate.

The examples offer experimental, as well as clinical and translational, evidence of a novel molecular mechanism for the migration and BM homing of MM cells. We document that eCyPA, but not its homolog CyPB, is produced in (FIG. 4H) and secreted by (FIG. 4E) BMECs, but not endothelial cells from other vascular beds (FIG. 12A) or by other stromal cells in the BM (FIG. 4G). eCyPA functions as a pleiotropic signaling factor (FIG. 5C) that promotes migration (FIG. 5A), growth (FIG. 5F), and BM colonization of MM cells (FIGS. 5G-I) via binding to its cognate receptor, CD147, on MM cells (FIG. 6). In the process, we have identified eCyPA as a novel target of the β-catenin/BCL9 transcriptional complex (FIG. 10I), and have provided evidence for a novel functional role of the Wnt signaling pathway and of BMECs in trafficking, recruitment, growth, and progression of MM (FIGS. 1-3). In addition, we have identified BMECs as the main source of eCyPA, but not SDF-1 which is secreted by other stromal cells (FIG. 14I). Thus our findings provide the first indication that BMECs and BMSCs play different roles in MM pathogenesis, and do so via different molecular mechanisms.

Although CyPA was initially recognized as the host cell receptor for the potent immunosuppressive drug Cyclosporine A, recent studies have revealed that it can be secreted by cells in response to inflammatory stimuli. Secreted eCyPA can initiate a signaling response in target cells and is a potent neutrophil, eosinophil, and T cell chemoattractant 31-34. Studies aimed at establishing the mechanism whereby eCyPA mediates its chemotactic activity have identified CD147 as the principal signaling receptor for eCyPA. Indeed, all human 37 and mouse 32 leucocytes examined to date require CD147 expression for eCyPA-mediated chemotaxis to occur.

CD147, also known as Extracellular Matrix Metalloproteinase Inducer (EMPRIN), is a type I integral transmembrane glycoprotein that belongs to the immunoglobulin super family. It plays critical roles in intercellular communication involved in chronic inflammation, immune-related functions, tumor metastasis and angiogenesis, and HIV infection. CD147 induces expression of the matrix metallopeptidases required for tumor invasion and metastasis via cell-cell and cell-matrix interactions. Recently, expression of CD147 has been broadly correlated with progression in ovarian, hepatocellular, bladder, cervical, lung, and gallbladder carcinomas, as well as hematological malignancies such as MM.

In regard to MM, we show that CyPB, although tested at much higher concentrations than those in BM serum of MM patients (FIG. 4J), induces proliferation of MM cells. Of particular relevance to our studies, however, is the observation that CD147 is not expressed in normal plasma cells, yet its expression correlates with MM progression.

Example 1 General Materials and Methods

Patient Samples and Cell Lines

BM specimens were obtained from patients with MM or from normal donors in accordance with Dana-Farber Cancer Institute Review Board protocols, and with informed consent in compliance with the Helsinki Declaration. BM mononuclear cells were isolated with the aid of a Ficoll gradient, and BMECs as well as MM primary cells were isolated using CD34 or CD138 magnetic beads (Miltenyi Biotec, Auburn, Calif.), respectively, as described in Sukhedo et al., Proc. Nat. Acad. Sci. (USA) 104:7516-7521 (2007). Primary BMECs and primary BMSCs from the same MM patient were prepared as follows: after Ficoll gradient, BM mononuclear cells were treated with collagenase, and single-cell suspensions were placed on plastic dishes. When only attached cells remained in the cultures, they were divided into two fractions and one was stored without further processing for subsequent use as BMSCs. From the other fraction, we purified BMECs using CD34 immunomagnetic beads. Purified BMECs cells were further expanded in culture ex-vivo and their identity confirmed by FC and immunoblot analysis using several endothelial cell markers (CD31, VEGF R1, CD138, and Factor VIII). Primary CLL and LPL cells were purified using CD19 magnetic beads (Miltenyi Biotec, Auburn, Calif.). All primary cells were >90% pure and fresh for functional studies or stored in liquid nitrogen for other subsequent studies. Established MM cell lines (MM1S, ABNL6, U266, H929, OPM2, and RPMI) were all from the Carrasco laboratory. The HG3 (CLL) and BCWM. 1 (LPL) cells were provided by Drs. Wu and Treon, respectively. Human BM-derived endothelial cell lines BMEC-60 and HBME-1 were kindly provided by Drs. van der Schoot and Giuliani, respectively. The stromal cell line HS5 was obtained from Dr. Mitsiades's lab. All cells were grown at 37° C. under a 5% $CO_2$ humidified atmosphere in RPMI 1640 medium supplemented with 10% fetal bovine serum (FBS). All cell lines were routinely tested using Human Cell Line Genotyping System (Promega), and were periodically surveyed for mycoplasma contamination with the help of a commercial detection kit (LT07-218, Lonza). Serum from BM and PB of MM patients were obtained from the Jerome Lipper Multiple Myeloma Center, Dana-Farber Cancer Institute. Studies with human subjects were approved by the Dana-Farber Cancer Institute Review Board Committee (IRB #01-206), and informed consent was obtained from all subjects.

Scaffold Mouse Xenograft Model $2 \times 10^6$ BMEC-60 cells, HS5 cells, PBMEC or PBMSC were trypsinized and seeded into poly-.epsilon.-caprolactone polymeric scaffolds generously provided by Dr. Tassone (see Calimeri et al., Leukemia 25: 707-711 (2011). Scaffolds were first coated with 50 µg/ml fibronectin (Santa Cruz). The seeded scaffolds were cultured in vitro for 2 weeks and implanted s.c. in the right or left flank of five-week old non-γ-irradiated CB17.Cg-PrkdcscidLystbg-J/Crl male mice (Charles River). Two weeks later, $5 \times 10^6$ luciferase-labeled MM1S or H929 cells were injected via the tail-vein into scaffold-implanted mice. Tumor burden was analyzed on the basis of luciferase bioluminescence using an LAS-4000 Luminescent Imager Analyzer (Fujifilm). Mice were euthanized 4 weeks later and the scaffolds removed for histological and IHC examination as described in Mani et al., Cancer Res. 69: 7577-86, 2009. Experiments were repeated independently three times. Animal experiments were approved by the Dana-Farber Cancer Institute Institutional Animal Care and Use Committee (IRB #10-039) and were in compliance with ethical practice. All the experiments were performed blindly, as the investigator who implanted the mouse did not know the content of the scaffolds. In animal studies using the Xenograft scaffold system, one experiment was excluded because MM1 S-luc or H929-luc cells grew within both the BMEC-60 coated scaffold and the spine and skull of the mouse, precluding optimal evaluation using the Xenogen system.

For in vivo treatment with CD147 Ab, the mouse scaffold system was modified as follows: scaffolds were pre-coated with BMEC-60 cells, incubated with MM1S-luc cells, and then implanted into the flank of non-γ-irradiated CB17.Cg-PrkdcscidLystbg-J/Crl mice. One week post-implantation the mice were subjected to whole-body imaging, and those with a comparable tumor burden were selected for Ab therapy. Mice were injected with 100 µl of a solution containing either 100 ng of isotype Ab or anti-CD147 Ab sc every other day in a region adjoining the scaffold. Tumor growth within each scaffold was evaluated by Xenogen imaging every five days. After 15 days, the scaffolds were removed and processed for histological and IHC analysis.

Complement-Dependent Cytotoxicity (CDC)

MM.1S-Luc cells ($1 \times 10^6$) were labeled with Calcein-AM (1 t/ml, Technologies, Grand Island, N.Y.) for 30 min in a $CO_2$ incubator at 37° C., washed twice with fresh mouse medium, and then cultured for 1 h with anti-CD147 Ab or isotype control Ab (10 µg/ml), in the absence or presence of mouse serum (20% final concentration). Cells were spun down and fluorescence in the supernatant was measured using a 490 nm excitation filter and a 520 nm emission filter. Percent specific lysis was calculated from the formula % Lysis=(Sample RFU-Background RFU/Total RFU-Background RFU).times. 100.

Immunoblot Analysis

Total protein samples were prepared from non-attached H929 and MM1S cells grown in CM from cultures of BMEC-60 or BMEC-1 cells attached for 72 hr. In some experiments, the cells were co-cultured with BMEC-60 cells using transwell chambers (Corning Costar, 0.45 .mu.m pore diameter). Immunoblotting was performed as described in Takada et al., Sci. Transl. Med. 4, 148ra117 (2012). When MM1S and H929 cells were treated with eCyPA or CD147 Ab, they were first incubated with eCyPA or CD147 Ab for 5 hrs in serum-free medium. Then 0.5% serum was added, and incubation was resumed for another 72 hrs before performing protein preparation. Anti-human primary antibodies included: BCL9 (2D4, Abnova), CyPA (ERPR7511, Abcam), CD147 (#13287, Cell Signaling), pSTAT3 (#9131, Cell Signaling), pERK (#4370, Cell Signaling), PARP (#9542, Cell Signaling), pAKT (#9271, Cell Signaling), Active-.beta.-catenin (05-665, Millipore), Factor VIII (A0082, DAKO), MMP-9 (MAB911, R&D), CyPB (MAB5410, R&D), and horseradish peroxidase (HRP)-conjugated actin (C-11, Santa Cruz). Actin Ab was used as a loading control. Secondary antibodies included: anti-rabbit IgG (HRP)-conjugated (W402b, Promega), and anti-mouse IgG (HRP)-conjugated (W401b, Promega). Protein concentrations were measured in triplicate by Bradford assay (BioRad). Optimal antibody concentrations were used according to the manufacturer's recomendations.

Lentiviral Infection

Validated expression plasmids for pLKO-shCyPA: #1, CCGGGTTCCTGCTTTC ACAGAATTACTCGAGTAAT-TCTGTGAAAGCAGGAACTTTTTG (SEQ ID NO:3); #2, CCGGCTGACTGTGGACAACTCGAATCTCGAGAT-TCGAGTTGTCCACAGTCA GTTTTG (SEQ ID NO:4) and pLKO-shCD147: #1, CCGGCCAGAATGACAAAGGCAAGAACTCGAGT (SEQ ID NO:5) TCTTGCCTTTGTCATTCTGGTTTTT (SEQ ID NO:6); #2, CCGGACAGTCTTCAC-TACCGTAGAACTCGAGTTCTACGGTAGTGAA-GACTGTT TTTTG (SEQ ID NO:7) were purchased from Sigma. The pLKO-Control-shRNA and pLKO-shBCL9 expression vectors are described in Mani et al., Cancer Res. 69: 7577-7586 (2009). Lentiviral packaging and infection of MMIS-luc and BMEC-60 cells was done according to manufacturer's protocol (Sigma). To minimize off-target effects of shRNAs, we implemented a series of assay conditions: i) shRNAs were designed to target the 3'UTR region, ii) the effect of the target shRNAs had to differ from that of a control shRNA containing scrambled nucleotide sequences, iii) the phenotypic response had to be reproducible using two distinct target shRNAs (#1 and #2), and iv) identical results had to be obtained with more than one targeted cell.

Cell Migration Assays

For cell migration assays, the top chamber of transwell plates (8 μM pore diameter, Corning Costar) was seeded with $2\times10^5$ MM1S-luc cells, and the bottom chamber was seeded with either medium (0.1% FBS) alone, BMEC-60 cells, BMEC-60 cell-conditioned medium, or plain medium containing CyPA and/or CD147. After 12 hrs of incubation, MM1S-luc cells that had migrated to the bottom chamber were collected and quantified by Xenogen Imaging. Migration of RPMI, U266, CLL, LPL, or primary tumor cells was evaluated by counting the number of unlabeled cells in the lower chamber. Each experiment was done in triplicate and repeated twice. Recombinant HPLC-purified eCyPA was purchased from BioMart Inc. and eCyPB (PPIB) human recombinant protein was purchased from Abnova. In most instances, 50 ng/ml of eCyPA or eCyPB diluted in serum-free RPMI medium was used. CM was collected from confluent cultures of BMEC-60 cells incubated for 48 hours. When needed, the CM was treated with 100 μ/ml proteinase K (19133, Qiagen) for 2 hrs and then deactivated for 15 min at 70° C. Anti-CD147 (UM-8D6) antibody and monoclonal mouse IgG1 (MOPC31C) were obtained from Ancell; anti-CXCR4 (MAB171) was from R&D systems. Migration data were normalized using the data obtained with medium alone. Results are means.±SD for triplicate assays.

Reporter Assays

Luciferase activity was measured using the Dual Luciferase Reporter Assay System (Promega), as described in Mani et al., Cancer Res. 69: 7577-7586 (2009). To measure Wnt reporter activity, BMEC-60 cells were transfected with TOP-FLASH, FOP-FLASH plasmid (Millipore), along with an internal Renilla control plasmid (hRL-null). Transfection was performed using FuGENE® (Roche) according to the manufacturer's protocol. The results were normalized to control for Renilla activity. The reported data represent the average of three independent transfection experiments in triplicate.

Cell Proliferation and Viability Assays

Cell proliferation was evaluated by [$^3$H]TdR incorporation as described in Mani et al., Cancer Res. 69: 7577-7586 (2009). When proliferation of MM cells was determined in the presence of HS5 or BMEC-60 cells, the latter were previously gamma-irradiated (10,000 rads) and dispensed into 96-well plates. Then, MM1S and H929 cells were co-cultured with either BMEC-60 cells, CM alone, CyPA, or CyPB for 72 hrs. Viability of MM1s-Luc cells were co-cultured with BMEC-60 cells and then treated with drugs as described was assessed, using the tumor cell-specific in vitro bioluminescence imaging (SS-BLI).

Histopathological and IHC Analysis

Tissue sections were processed as described in Mani et al., Cancer Res. 69: 7577-7586 (2009). Human tissue samples were obtained from the Department of Pathology, Brigham and Women's Hospital. Sections were incubated with primary antibodies (5 μg/ml) or the corresponding IgG fraction of pre-immune serum overnight at 4° C. in blocking solution (3% BSA/PBS). Anti-human primary specific antibodies included: BCL9 (ab37305, Abcam), CD138 (PN IM 2757, Beckman Coulter), CD34 (M71165, DAKO), ERG (5115-1, Epitomics), Caspase-3 (#9664, Cell Signaling), CD147 (MEM-M6/1, LifeSpan BioSciences), CyPA (ERPR7511, Abcam) and CyPB (AV44365, Sigma); and were visualized with the aid of the corresponding biotinylated antibody coupled to streptavidin-peroxidase complex (Vector Labs). For CD147 immunohistochemistry, non-decalcified BM clots were used. For negative controls, tissue sections were incubated in the absence of primary antibodies or pre-immune serum from the species of origin of the primary antibody. Optimal antibody concentrations were used according to manufacturer's recommendation.

Immunofluorescence

Single-cell suspensions were spun onto glass slides using a cytocentrifuge (Shandon) or were grown on polylysine-coated slides (p8920, Sigma), as described in Mani et al., Cancer Res. 69: 7577-7586 (2009). Cells were fixed at room temperature in 2% paraformaldehyde for 20 min, permeabilized in TBS-Tween 20 for 20 min, washed three times in PBS, and then blocked with 5% bovine serum albumin in PBS for 2 h before addition of primary antibodies against BCL9 (ab37305, Abcam), β-catenin (CAT5-H10, Zymed), Myeloperoxidase (A0398, DAKO), CyPA (ERPR7511, Abcam), Alexa Fluor 647-conjugated CD147 (HIM6, Biolegend), or FITC-conjugated CD138 (MI15, Becton Dickinson). Cells were incubated overnight with primary antibodies at 4° C., and then washed three times in PBS before staining with secondary antibodies conjugated to Alexa Fluor 488 (A11034, Molecular Probes) or Alexa Fluor 546 (A11035, Molecular Probes). Images were acquired with the aid of a Bio-Rad Radiance 2000 laser scanning confocal or Nikon Eclipse E800 phase-contrast microscope. Optimal antibody concentrations were used according to manufacturer's recommendations.

Flow Cytometry (FC)

Harvested cells in aliquots of up to $1\times10^6$ cells/100 μL were dispensed into FACS tubes and stained for FC, as described Mani et al., Cancer Res. 69: 7577-7586 (2009). Anti-human antibodies included: CD147-Alexa Fluor 647 (HIM6, Biolegend), CD147-PE (8D12, eBioscience), CD19-FITC (SJ25C1, Becton Dickinson), CD19-APC (HIB19, Becton Dickinson), CD5-FITC (53-7.3, Becton Dickinson), CD138-APC (MI15, Becton Dickinson), and isotype control mouse IgG1 к (P3.6.2.8.1, Bioscience). Optimal antibody concentrations were used according to manufacturer's recommendations.

ELISA

Serum levels of eCyPA and eCyPB in BM and peripheral blood samples from MM patients were measured by ELISA according to the manufacturer's protocols for eCyPA (KA1176, Abnova), eCyPB (ABIN414776, USCN Life Science), and SDF-1 (DSA00, R&D), respectively. For the measurement of eCyPA, eCyPB, and SDF-1 from cell supernatants, $1\times10^6$ cells were dispensed in triplicate into 12-well plates and cultured for different times. The spent medium was then replaced with an equal volume of fresh medium, the incubation was resumed for another 12 h, and finally triplicate samples of supernatant containing equal amounts of total protein were used for ELISA analysis. Standard curves were linear, and 100 μl of each sample was used for analysis in triplicate.

Mass Spectrometry (MS)

Bands excised from silver-stained gels were cut into approximately 1 mm³ pieces, and the latter were analyzed by mass spectrometry, as described in Peng et al., J. Mass Spectrom. 36: 1083-1091 (2001) and Levanon et al., Oncogene 29: 1103-1113 (2010). BMEC secretomes were analyzed directly, according to a previously described protocol (Ria et al., Clin. Cancer Res. 15: 5369-5378 (2009)). Approximately $1\times10^6$ BMEC-60 cells were lentivirally transduced with control shRNA or shBCL9. These, along with HS5 cells, PBMEC #1, and PBMEC #2, were dispensed into 12-well plates, which were kept for 6 h at 37° C. under 5% $CO_2$, and rinsed twice with 2 ml of PBS. Then, 200 μl of fresh PBS was added and the cells were incubated at 37° C. under 5% $CO_2$ for another 24 h. Supernatants were collected and centrifuged for 5 min at 300 rpm to remove floating cells, and the amount of total protein in each sample was measured. Total protein was loaded onto agarose gels in amounts commensurate with the decreased levels resulting from BCL9 knockdown; after electrophoresis, the gels were silver-stained according to the manufacturer's protocol (Bio-Rad 161-0449). The remaining aliquots were processed for LC-MS/MS analysis. Proteins were reduced with 10 mM DTT at 56° C. for 1 h, alkylated with 22.5 mM IAA for 30 min at room temperature in the dark, and digested with 2.5 µg of trypsin (Promega) at 37° C. overnight. Peptides were desalted using POROS10R2 (Applied Biosystems) and reconstituted with 0.1% TFA. Peptides were then analyzed by LC-MS/MS on an Orbitrap-XL mass spectrometer (Thermo Scientific), as described in Ficarro et al., Anal. Chem. 81: 3440-3447 (2009). MS/MS spectra were searched against a forward-reversed human NCBI Refseq database using Mascot (Matrix Science, version 2.2.1), and were filtered to a 1% false-discovery rate. Five different criteria were used to select proteins from MS raw data: 1) molecular weights had to be <28 kDa; 2) more than two unique target peptides had to be identified for each protein; 3) peptides giving an overly weak signal were discarded; 4) the protein was cytoplasmic or secreted; 5) nucleoprotein or cytoskeleton proteins were excluded.

Statistical Analysis

Statistical differences between groups were estimated by means of the unpaired Student's t-test, with p≤0.05 being considered significant. Analysis of tumor burden was done using factorial analysis in SPSS 13.0. mRNA expression of CD147 (GSE6477) was measured in BM plasma cells from a normal subject or a MM patient. All experiments were done blindly, without the investigator's knowing the identity of the samples, which were labelled only with code numbers.

Figure 1B:
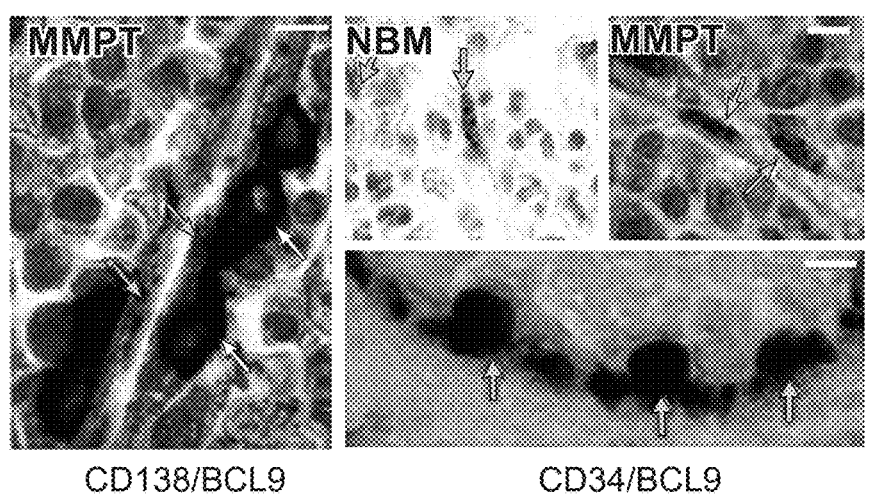
(FIG. 1B) Representative immunohistochemical analysis of BCL9 expression (brown color) in endothelial cells (arrows) in BM biopsies from MM patients (MMPT) or normal bone marrow (NBM) from otherwise healthy subjects. Selected representative cases are shown. Anti-CD138 staining (red color) is used as a marker of plasma cells on the left panel (arrows). Anti-CD34 staining (red color) is used as a marker of endothelial cells (right bottom panel). Immunoblots (FIG. 1C) and immunofluorescence (FIG. 1D) analysis of BCL9 (left panel) and β-catenin expression (middle panel) in primary endothelial cells derived from BM from two MM patients (PBMEC #1, PBMEC #1) and two BM endothelial cell lines (BMEC-1, BMEC-60). Note co-expression of BCL9 and β-catenin by immunoblotting and by nuclear co-localization immunofluorescence (right panel). Factor VIII is used as marker of endothelial cells in immunoblots.
Figure 1C:
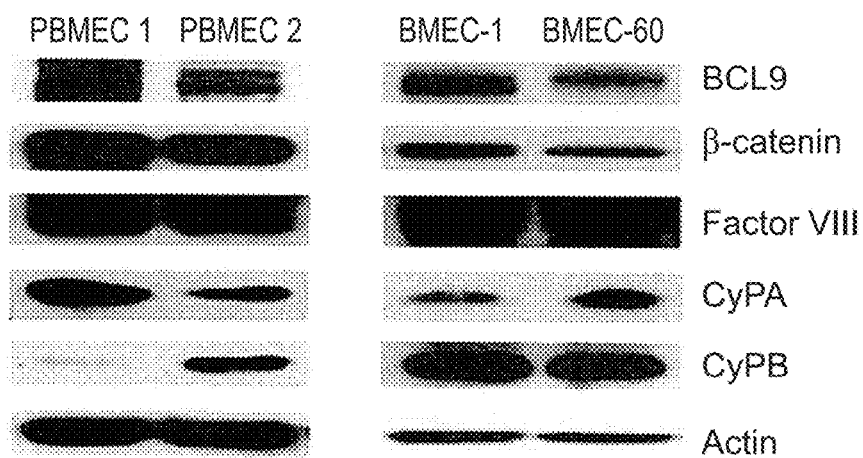
FIG. 1. Analysis of BCL9 expression and canonical Wnt activity in BMECs.
(FIG. 1E) Wnt reporter activity of BMEC-1, BMEC-60 and PBMEC #1 cells lentivirally transduced with shRNAs against BCL9 (BCL9-shRNA) compared with cells lentivirally transduced with scrambled shRNAs (Control).
(FIG. 1F) Proliferation of BMEC-1, BMEC-60 and PBMEC #1 cells treated with medium alone (Vehicle) or in the presence of 10 uM Stabilized Alpha Helix peptides of BCL9 SAH-BCL9 ($P<0.006$). Proliferation and Wnt reporter data was normalized based on control or vehicle data. Results are means±SD for assays performed in triplicate. Statistical significance of differences between groups was determined by applying the unpaired Student's t-test.
Figure 1D:
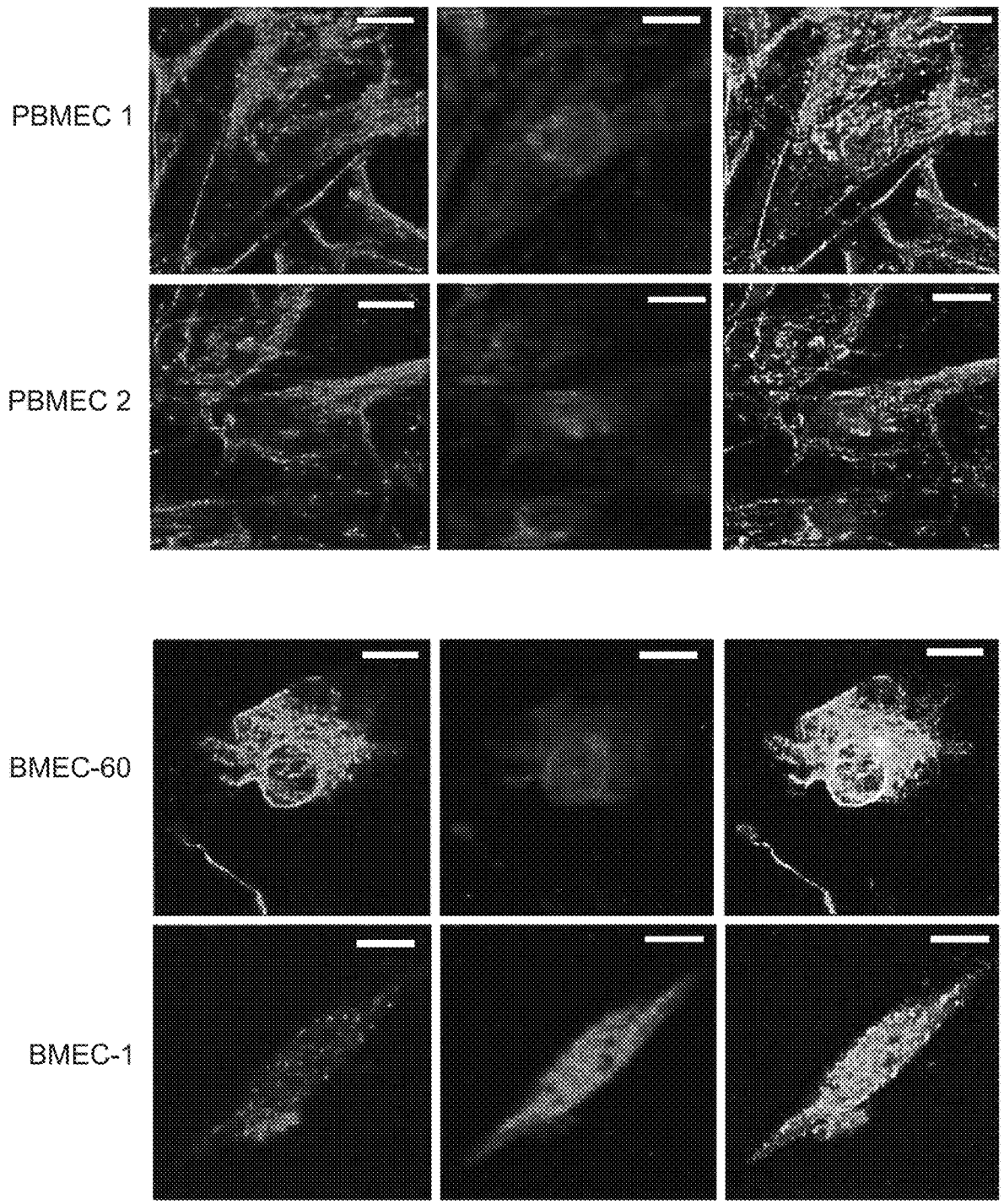
Figure 1E:
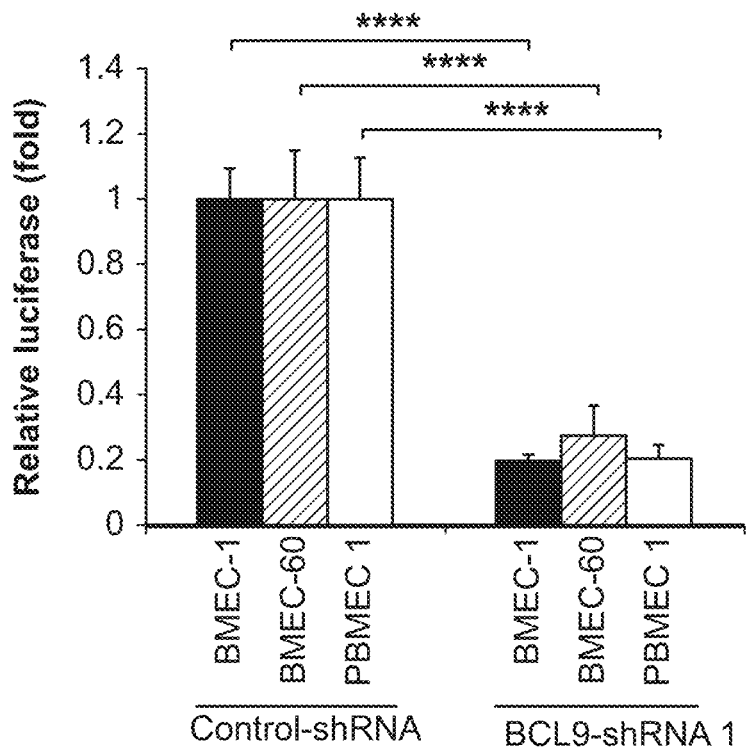
Figure 1F:
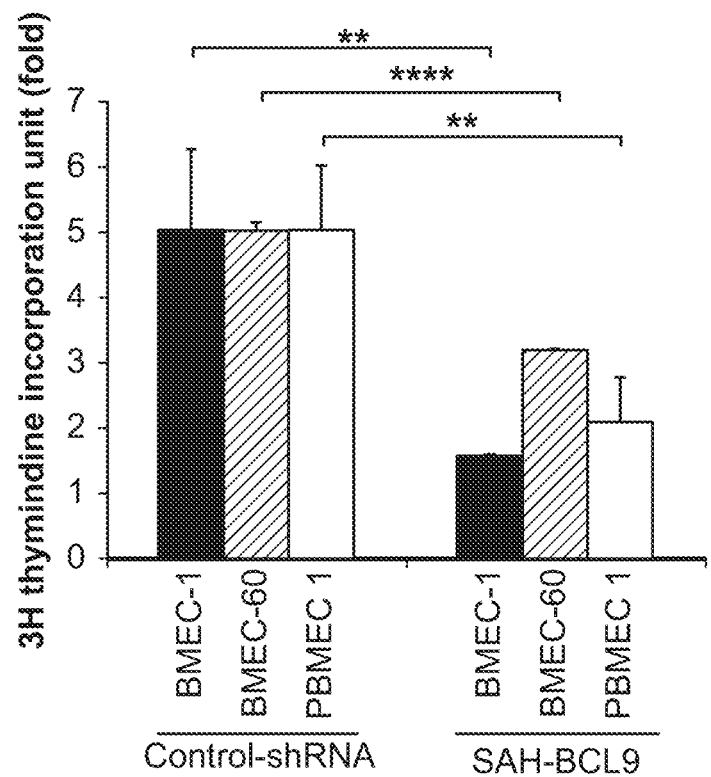
Figure 9A:
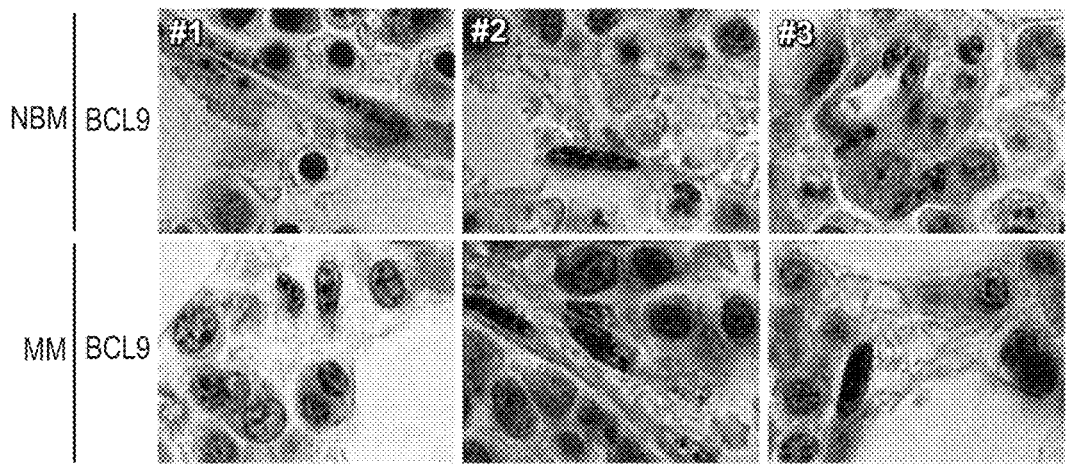
(FIG. 9A) Representative BCL9 immunostains (brown) in BMECs from normal individuals (NBM) (n=20) and MM patients (n=60).
Figure 9B:
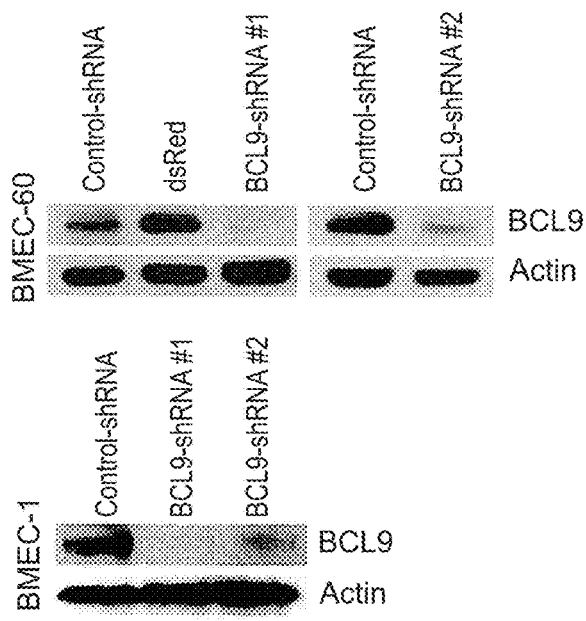
(FIG. 9B) BCL9 immunoblots in total protein extracts from BMEC-60 and BMEC-1 cells lentivirally transduced with control-shRNA or BCL9-shR-NAs. Actin was used as a loading control.
Figure 9C:
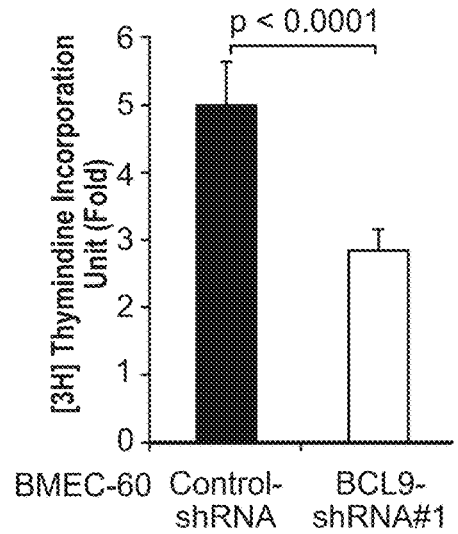
(FIG. 9C) Proliferation of BMEC-60 cells lentivirally transduced with Control-shRNA or BCL9-shRNA.

Example 2 the BCL9 Oncogene Promotes Proliferation of Bone-Marrow-Derived Endothelial Cells BM angiogenesis is a hallmark of MM progression and a positive correlate of disease activity (FIG. 1A), suggesting that BMECs promote MM progression. However, the mechanism(s) by which BMECs exert this effect are not fully understood. The BCL9 oncogene is an essential transcriptional co-activator of the Wnt/β-catenin complex, and plays critical roles in the pathogenesis of a broad range of human cancers, including colorectal cancer (CC) and MM. Stabilized Alpha-Helix peptides of BCL9 (SAH-BCL9) that dissociate native β-catenin/BCL9 complexes selectively suppress Wnt transcription, elicit mechanism-based anti-tumor responses in vitro, and ablate intra-tumoral blood vessel formation in mouse xenograft models of CC and MM 23. These results suggested that BCL9 plays a role in MM-associated angiogenesis and disease progression, prompting us to evaluate its expression in BMECs by immunohistochemistry (FIGS. 1B and 9A). High levels of BCL9 expression were detected in the nucleus of spindled cells in close physical contact with MM cells (FIG. 1B, left). High expression was observed in all BM biopsies examined, from normal individuals (NBM) (n=20) (FIG. 1B, right, top-left and FIG. 9A, top) as well as MM patients (n=60) (FIG. 1B, right, top-right and FIG. 9A, bottom). No major differences in BCL9 expression in BMECs were noted between normal individuals and MM patients. Specific expression of BCL9 in BMECs was confirmed by double immunostains, which detected BCL9 and the endothelial cell marker CD34 on the same cells (FIG. 1B, right-bottom). Co-expression and nuclear co-localization of BCL9 and β-catenin in two primary BMECs isolated from MM patients (PBMEC #1 and PBMEC #2), as well as in two established cell lines BMEC-60 and BMEC-1, was confirmed by immunoblotting (FIG. 1C) and double immunofluorescence (FIG. 1D) analysis. Knockdown of BCL9 in BMEC-60, BMEC-1 and PBMEC #1 cells using previously validated shRNA lentiviral approaches (BCL9-shRNAs) (FIG. 9B) 19 was associated with a significant decrease in Wnt reporter activity (FIG. 1E) and cell proliferation (FIG. 9C). Consistent with our previous in vivo studies, proliferation of BMECs in culture was likewise inhibited by SAH-BCL9 (FIG. 1F).

Figure 2A:
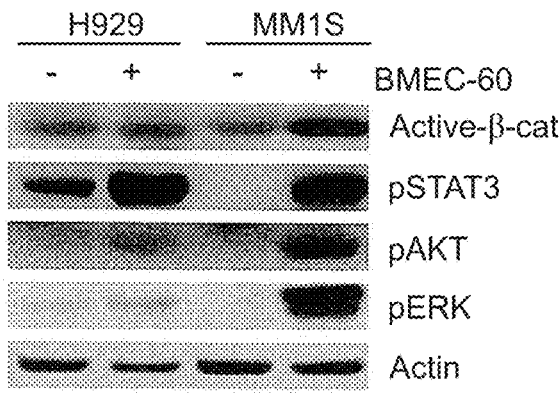
FIG. 2. Biochemical and functional analysis of MM cells upon interaction with BMECs. Immunoblot analysis of total protein extracts from H929 and MM1S cells incubated in the absence (−) or presence (+) of BMEC-60 cells in the same (FIG. 2A) or separate (FIG. 2B) chambers (transwells).
(FIG. 2C) Immunoblot analysis of total protein extracts from MM1S cells incubated in the absence (−) or presence (+) of endothelial cells derived from BM from two different MM patients (PBMEC #1, PBMEC #2) using transwell chambers. Cell proliferation assays of MM1S cells (FIG. 2D) and MM cells from two different MM patients (MMPT #1 MMPT #2) (FIG. 1E), and incubated in the absence (−) or presence (+) of BMEC-60 cells using transwell chambers.
(FIG. 2F) Cell viability assays using the tumor cell-specific in vitro bioluminescence imaging (CS-BLI) 44 of MM1S-luc cells incubated in the presence or absence of increasing concentrations of doxorubicin (top) or dexamethasone (bottom), without (−) or with (+) BMEC-60 cells.
(FIG. 2G) Proliferation of MM1S and H929 cells in the absence (−) or presence (+) of endothelial cells from BM of two different MM patients (PBMEC #1, PBMEC #2).
(FIG. 2H) Immunoblot analysis of total protein extracts from H929 and MM1S cells incubated in transwell chambers in the presence of γ-irradiated BMEC-60 cells lentivirally transduced with either scrambled shRNAs (Control) or shRNAs against BCL9 (BCL9-shRNAs).
(FIG. 2I) Knockdown expression of BCL9 in γ-irradiated BMEC-60 cells was associated with reduced proliferation of co-cultured MM1S cells. Proliferation data was normalized based on control data. Results are means±SD for assays performed in triplicate. Statistical significance of differences between groups was determined by unpaired Student's t-test.
Figure 2B:
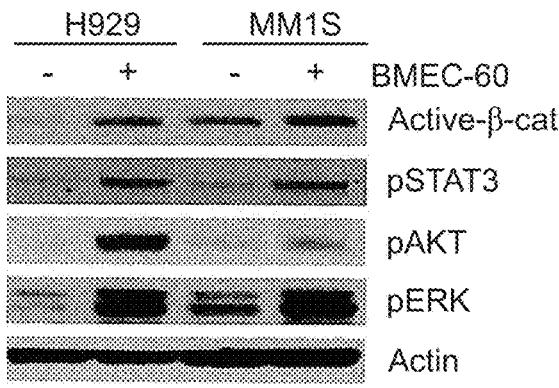
Figure 2C:
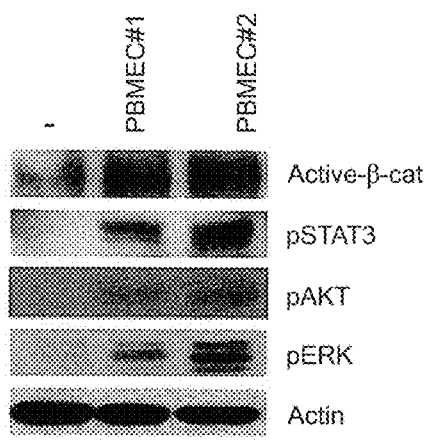
Figure 2D:
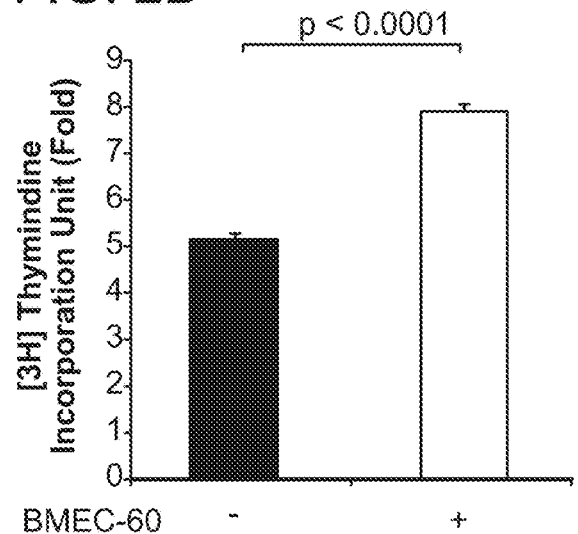
Figure 2E:
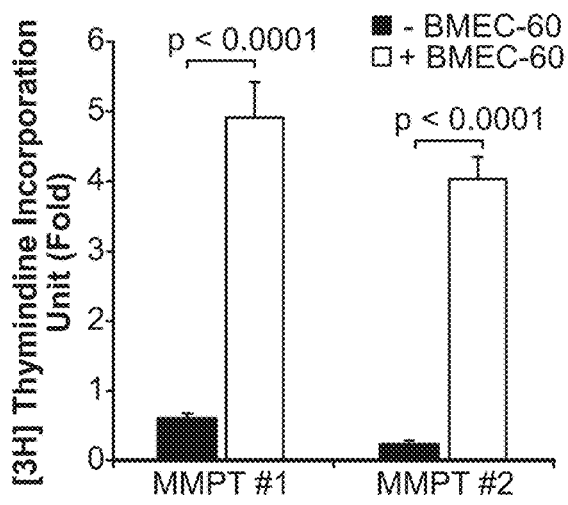
Figure 2F:
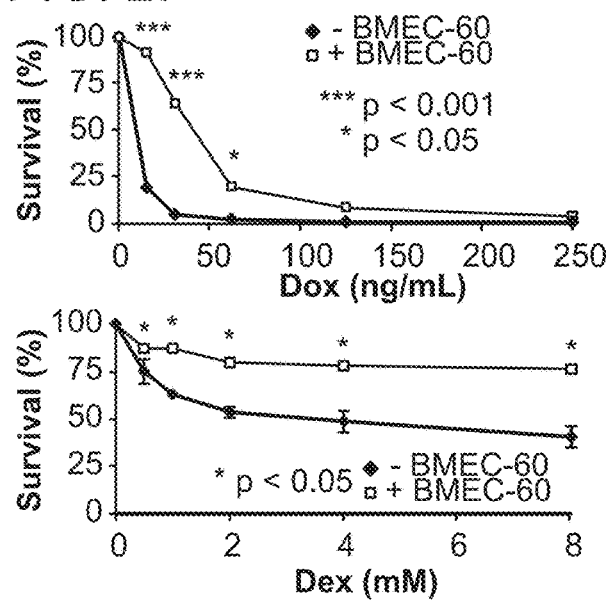
Figure 2G:
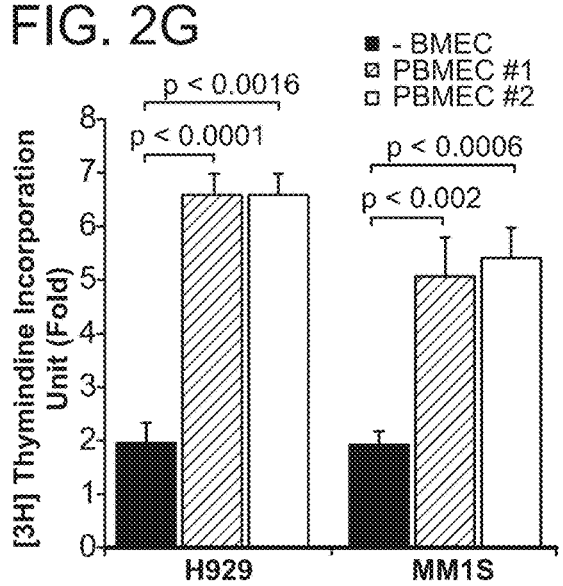
Figure 2H:
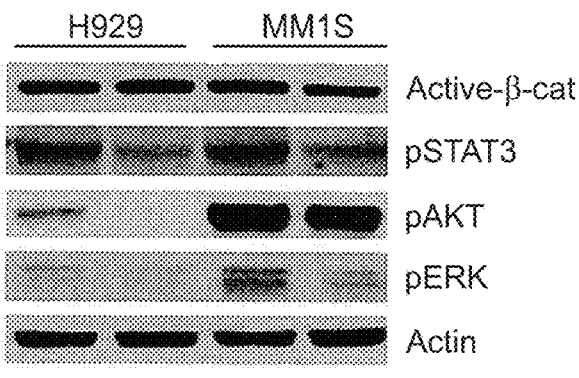
Figure 2I:
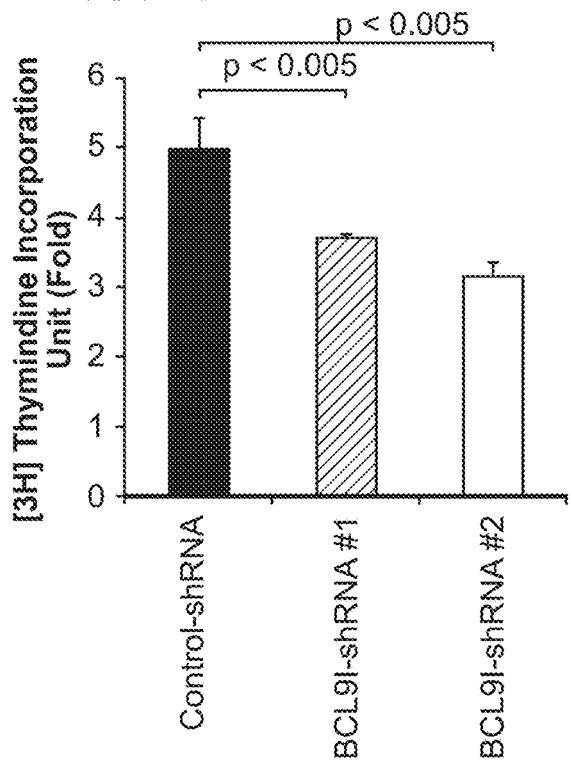

Example 3 Bone Marrow Endothelial Cells (BMECs) Promote Proliferation and Survival of MM Cells For a long time, BM-derived stromal cells were considered to be the main and only cell type with which MM cells interact functionally. However, once BM angiogenesis was recognized as a positive correlate of disease activity (FIG. 1A), it became clear that BMECs contribute to MM progression. To understand the molecular mechanisms by which BMECs promote MM progression and to evaluate the possible role of BCL9 in this process, we performed biochemical and functional assays of co-cultured cells. As determined by immunoblot analysis of total protein extracts, incubation of MM cells in the presence of BMEC-60 cells activates several signaling pathways compared with MM cells incubated alone (FIG. 2A). Among these pathways were found to be the Wnt/.beta.-catenin, STAT3, AKT, and ERK pathways, which are known to promote survival, proliferation, and migration of MM cells. Similar changes were observed when MM and BMEC-60 cells were co-cultured in separate chambers (i.e. transwell assay) (FIG. 2B), indicating that soluble factor(s) secreted by BMEC-60 cells promote(s) these signaling changes. Primary BMECs were as effective as BMEC-60 cells in secreting this factor(s) and promoting signaling changes (FIG. 2C). In addition, co-culture with BMEC-60 cells likewise promoted proliferation of MM cells (FIG. 2D) and MM primary tumors (FIG. 2E), and elicited drug resistance in MM1S cells (FIG. 2F). Primary BMECs were as effective as BMEC-60 cells in promoting proliferation of H929 and MM1S cells (FIG. 2G). Furthermore, knockdown of BCL9 in BMEC-60 cells was associated with decreased pSTAT3, pAKT, and pERK activation in transwell assays (FIG. 2H) using H929 and MM cells (FIG. 2H), and was associated with lower proliferation of co-cultured MM cells (FIG. 1).

Example 4 Bone Marrow Endothelial Cells Promote Migration and Bone Marrow Colonoization of Multiple Myeloma Cells Since activation of the ERK pathway has been previously implicated in promoting cell migration, our finding of enhanced pERK expression in MM cells co-cultured with BMEC-60 cells (FIGS. 2A, B, H) prompted us to ask whether this activation was also associated with increased migration. In vitro transwell assays revealed that conditioned medium (CM) derived from cultures of BMEC-60 cells (FIG. 3A) or primary BMECs (FIG. 3B), but not from BM derived stromal HS5 cells (FIG. 3C), promoted migration of MM1S cells labeled with luciferase (MM1S-luc), compared with the same cells incubated without CM (FIG.

Figure 3A:
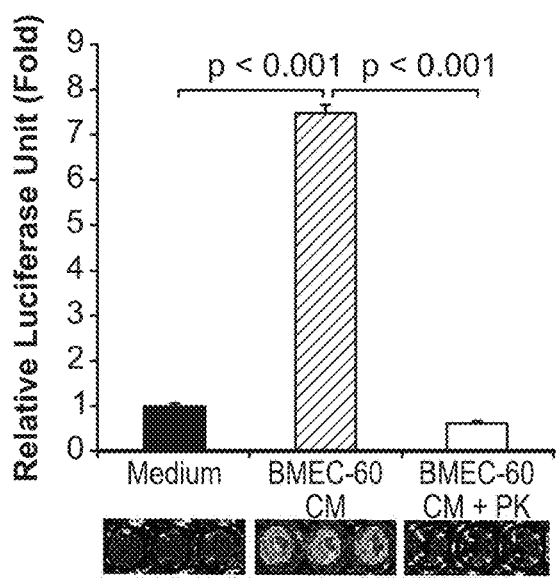
(FIG. 3A) growth in medium alone (medium), conditioned medium from BMEC-60 cells (BMEC-60-CM) or conditioned medium derived from BMEC-60 cells and treated with proteinase K (BMEC-60 CM+PK)
Figure 3B:
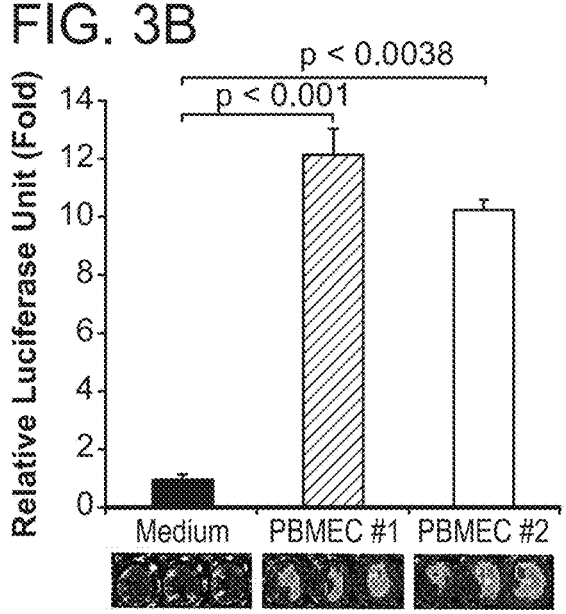
(FIG. 3B) growth in the absence or presence of endothelial cells derived from BM from two different MM patients (PBMEC #1, PBMEC #2)
Figure 3C:
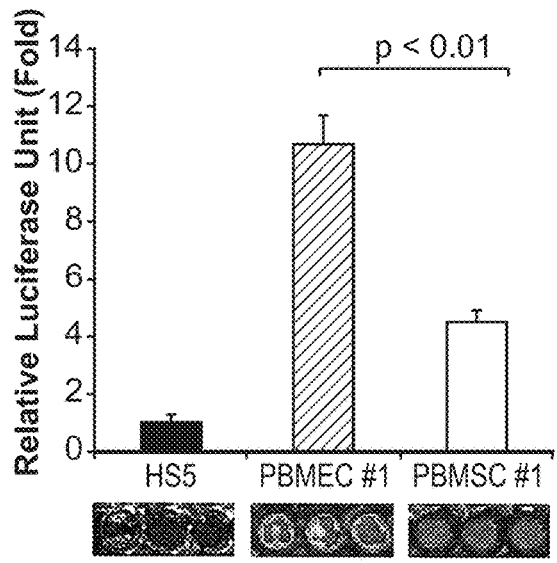
(FIG. 3C) growth in the presence of HS5 cells or PBMEC #1 and PBMSC #1 isolated from same patient. Migration data was normalized based on data of medium alone. Results are means±SD for assays performed in triplicate. Statistical significance of differences between groups was determined by unpaired Student's t-test.
Figure 9D:
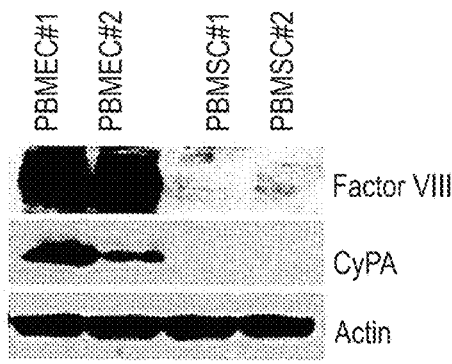
(FIG. 9D) Immunoblot analysis of Factor VIII and CyPA expression in primary BMECs (PBMEC #1 and PBMEC #2) and primary BMSCs (PBMSC #1 and PBMSC #2) isolated from the same MM patient.
Figure 9E:
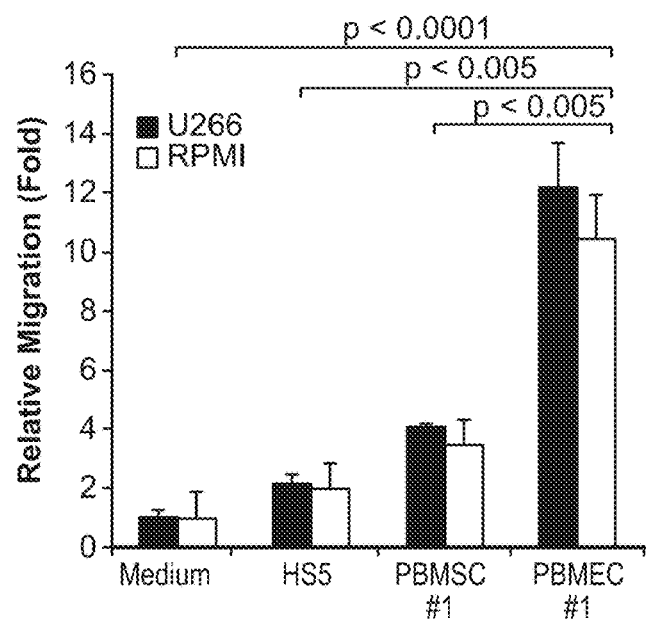
(FIG. 9E) Transwell migration assays of U266 and RPMI cells incubated in the presence of medium alone or HS5, PBMSC #1 or PBMEC #1 cells.

3A). Protease treatment (i.e., Proteinase K) of BMEC-60-derived CM (FIG. 3A) markedly reduced migration of MM1S-luc-cells. Migration of other representative MM cell lines (i.e., U266 and RPMI) was also significantly enhanced by CM derived from cultures from primary BMECs, but not from primary BMSCs, isolated from the same patient or from HS5 cells (FIGS. 9D, E). Furthermore, migration of MM1S-luc cells was enhanced to a greater degree by primary BMECs than by primary BMSCs isolated from the same MM patient (FIG. 3C).

Figure 3D:
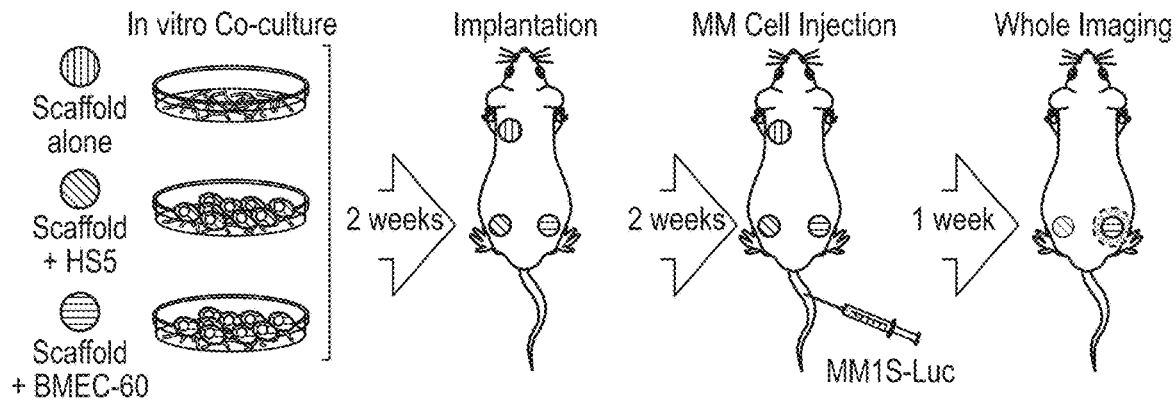
(FIG. 3D) Diagram of the three-dimensional poly-E-caprolactone scaffold xenograft mouse model. Xenogen data (FIG. 3E), time course (FIG. 3F), and histologic analysis (FIG. 3G) of MM1S-luc cell growth within non-coated scaffolds (orange) or within scaffolds coated with HS5 (green) or BMEC-60 (blue) cells. ERG (Ets-related gene): Endothelial cell marker. Xenogen data (FIG. 3H), time course (FIG. 3I), and histologic analysis (FIG. 3J) of MM1S-luc cell growth within scaffolds coated with primary BM endothelial cells (PBMEC #1 and PBMEC #2) or primary BM stromal cells (PBMEC #1 and PBMEC #2) isolated from same MM patient. Statistical analysis of tumor burden was done using factorial analysis in SPSS 13.0. The results of two representative experiments of three are shown.
Figure 3H:
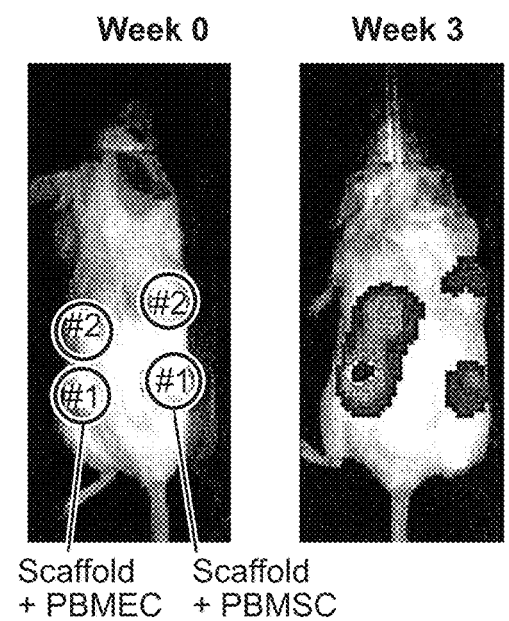
FIG. 3. In vitro and in vivo migration of MM cells toward BMECs. Transwell migration assays of MM1 S-luc cells incubated under different conditions.
Figure 3I:
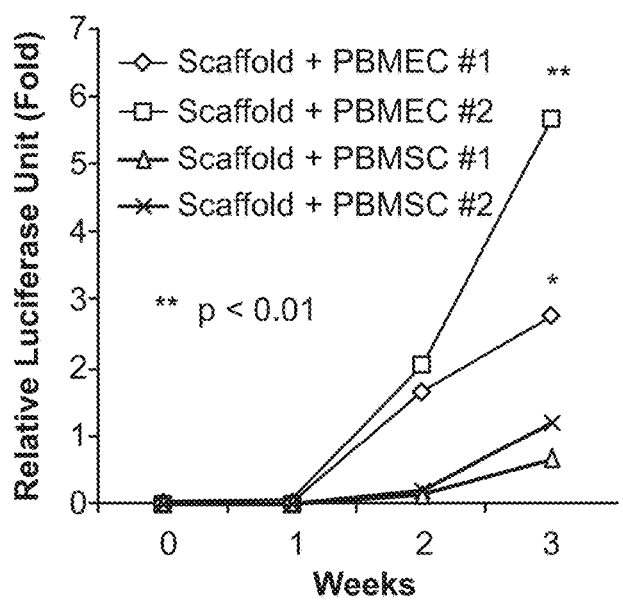
Figure 3J:
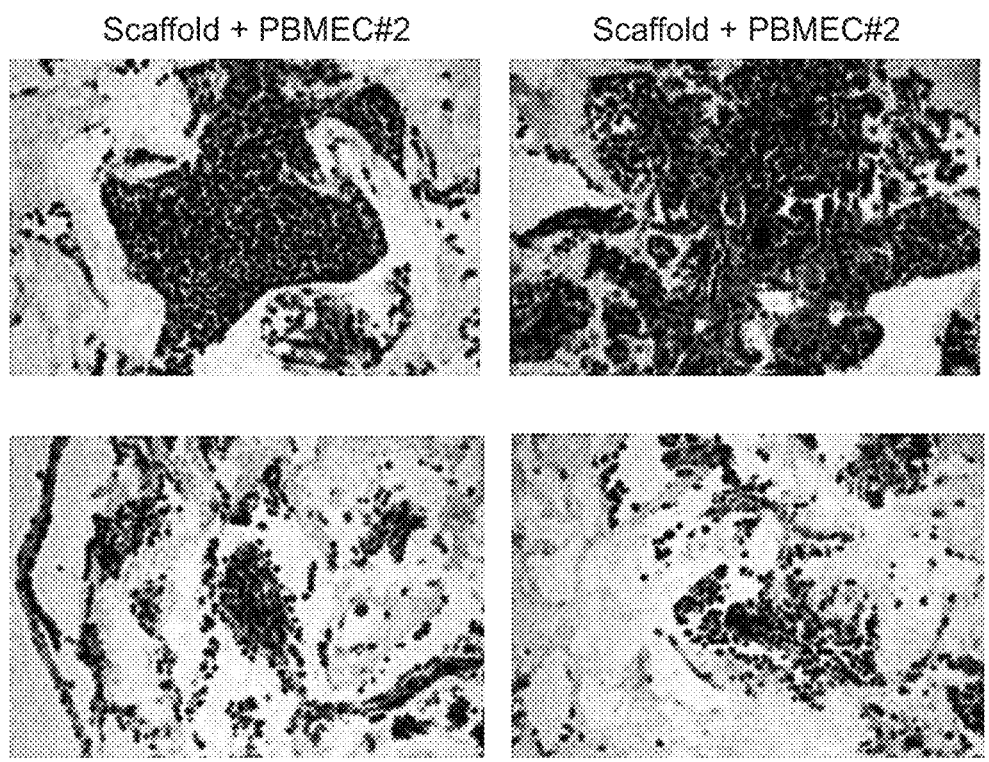
Figure 9F:
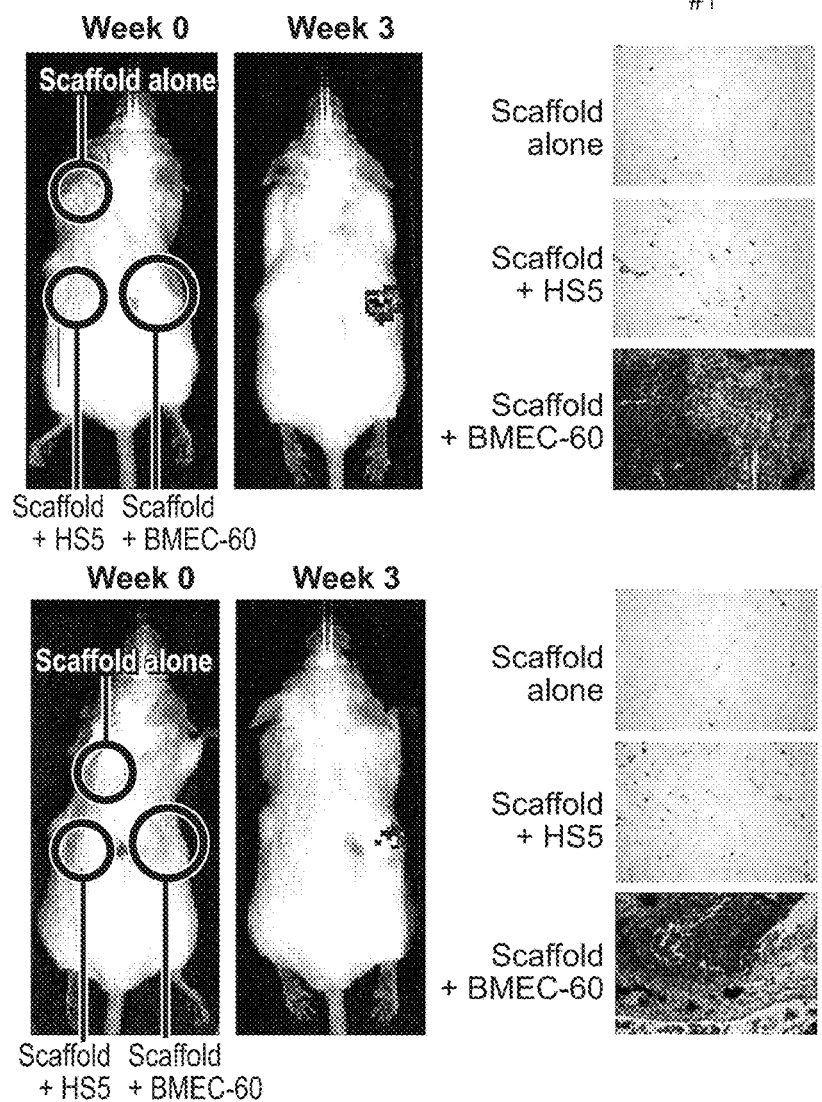
(FIG. 9F) Left and right, results of two independent experiments shown in FIGS. 3E-G. Xenogen data (FIG. 9G), time course (FIG. 9H), and histologic analysis (FIG. 9I) of H929-luc cell growth within scaffolds coated with PBMEC #1 cells, but not in uncoated, scaffolds.
Figure 9G:
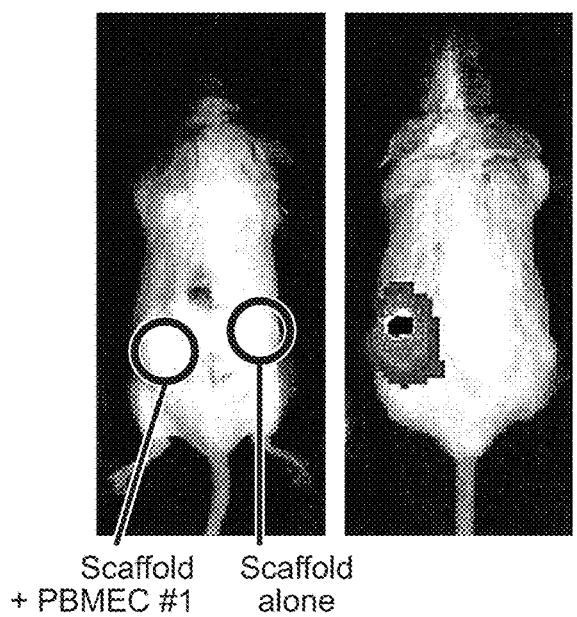
FIG. 9.
Figure 9H:
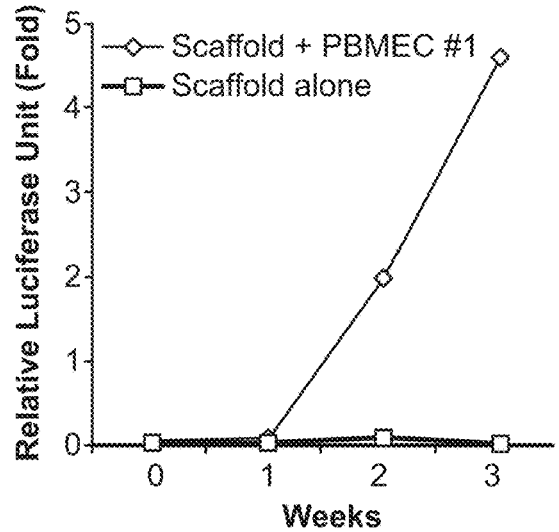
Figure 9I:
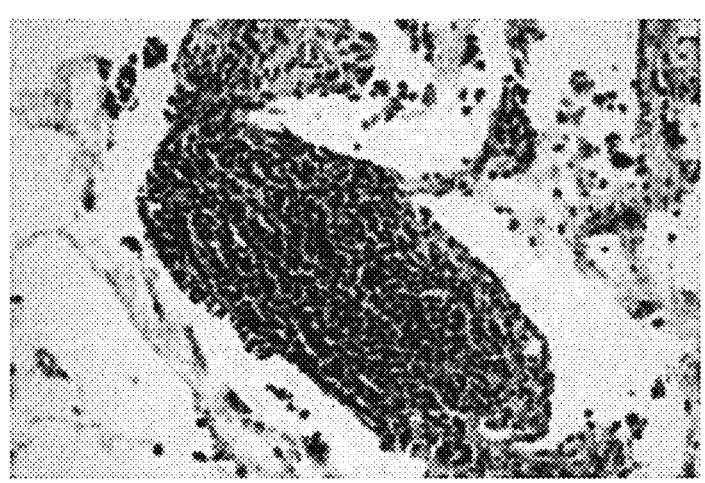
Figure 9I:
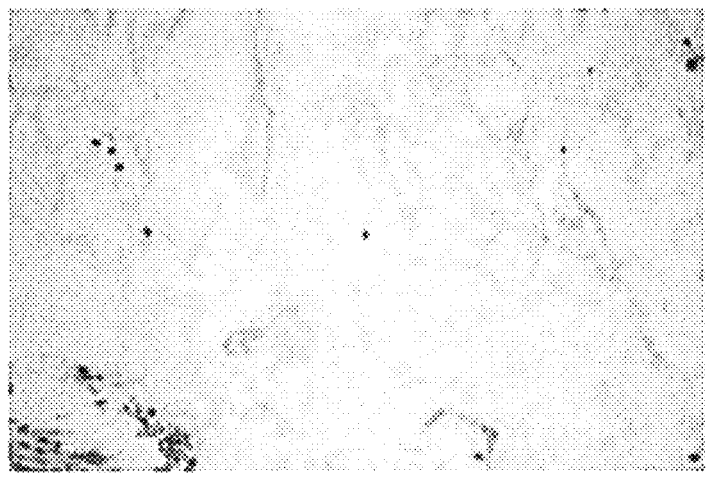
Figure 10A:
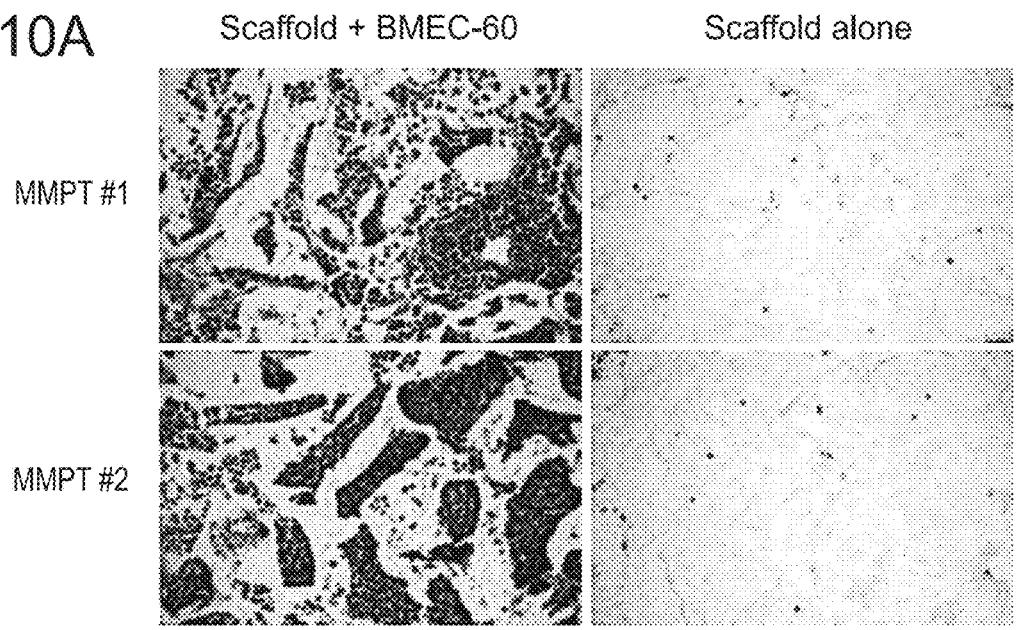
(FIG. 10A) Histologic analysis of primary MM cell growth (MMPT #1 and MMPT #2) in scaffolds coated with BMEC-60 cells, but not in uncoated scaffolds in the scaffold mouse xenograft model.

To further investigate the role of BMECs in the migration and chemoattraction of MM cells in vivo, we used a scaffold mouse xenograft system. Fibronectin-precoated scaffolds were cultured alone or in the presence of BMEC-60 or HS5 cells for two weeks until uniform coating of the scaffold meshwork was observed. Scaffolds were implanted subcutaneously at different sites in the flank of the same non-γ-irradiated CB17.Cg-PrkdcscidLystbg-J/Crl mouse, as depicted in FIG. 3D. Two weeks after implantation when growth of host connective tissue and blood vessels surrounding the scaffolds was demonstrable (as determined in pilot experiments), $2×10^6$ MM1S-luc cells were injected into the tail vein. In vivo tumor growth within each scaffold was followed over time by xenogen whole-body imaging. Since transplanted human MM cell lines can grow within the BM of γ-irradiated mice, non-irradiated mice were used to reduce the background signal and delay the spread of MM1S-luc cells to the spine. In three independent experiments, we consistently observed that only scaffolds coated with BMEC-60 cells could support growth of MM1S-luc cells, whereas MM1S-luc cells failed to propagate either in scaffolds without cells or in those coated with HS5 cells (FIGS. 3E-G). Four weeks post-transplantation, scaffolds were removed and subjected to histological (FIG. 3G, top) and immunohistochemical (FIG. 3G, bottom) analysis, confirming the presence of HS5 or BMEC-60 cells within the scaffolds and the infiltration of MM1S-luc cells in scaffolds coated with BMEC-60 cells, but not in those without cells. Only rare scattered MM1S-luc cells were observed in scaffolds coated with HS5 cells (see also FIG. 9F for triplicate experiments). Migration and growth of H929-luc cells were similarly observed in scaffolds coated with primary PBMECs, but not in uncoated scaffolds (FIGS. 9G-I). Furthermore, migration and growth of primary MM cells in scaffolds coated with BMEC-60 cells were observed (FIG. 10A), albeit at much lower frequency than that of MM1S-luc cells (2/10 vs. 2/2). Since MM primary cells are not susceptible to transduction with lentivirally expressed luciferase, growth of these cells in the scaffold was evaluated only by histologic examination of scaffolds after four weeks of tail-vein injection (FIG. 10A). Primary BMECs were observed to be much more efficient than primary BMSCs from the same patient's BM in promoting migration and growth of MM1S-luc cells within scaffolds (FIGS. 3H-J).

Example 5 BCL9 Knockdown in BMECs Reduces Migration and Growth of MM Cells

Figure 4A:
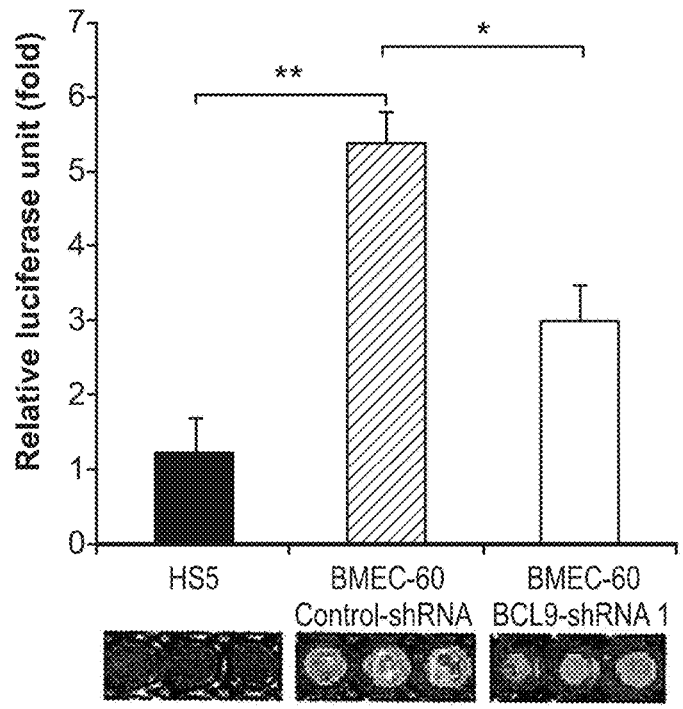
(FIG. 4A) Transwell migration assays of MM1S-luc cells incubated in the presence of HS5 cells or BMEC-60 cells lentivirally transduced with scrambled shRNAs (Control-shRNA) or shRNAs against BCL9 (BCL9-shRNA). Xenogen data (FIG. 4B), time course (FIG. 4C), and histologic analysis (FIG. 4D) of MM1S-luc cell growth within scaffolds coated with BMEC-60 cells lentivirally transduced with scrambled shRNAs (Control-shRNA) or shRNAs against BCL9 (BCL9-shRNA).
Figure 4B:
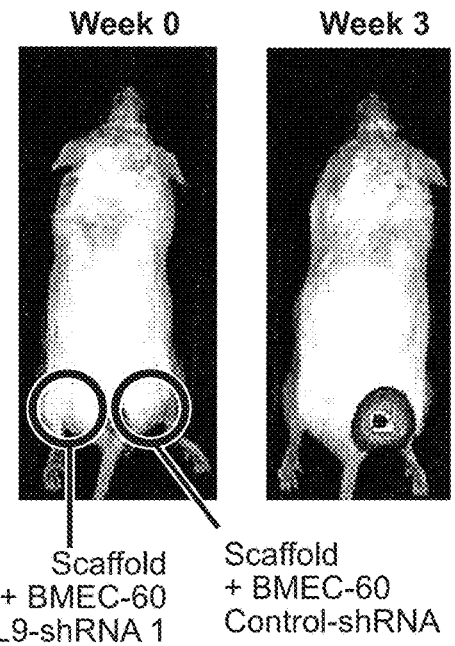
FIG. 4. Secretion of eCyPA and eCyPB by BMEC and increased BM serum levels of eCyPA in MM patients.
(FIG. 4E) Histogram representation of proteins identified by mass spectrometric analysis of excised bands (blue) and whole protein supernatants from BMEC-60 transduced with Control-shRNA (pink), as well as PBMEC #1 (yellow) and PBMEC #2 (green) cells. At the intersection of the diagram is eCyPA and eCyPB identified by both procedures.
(FIG. 4F) ELISA of eCyPA and eCyPB levels in CM from HS5 and BMEC-60 cells lentivirally transduced with Control-shRNAs or BCL9-shRNA. CM was taken after 24 hrs incubation in PBS.
(FIG. 4G) ELISA of eCyPA and eCyPB in CM from primary BM endothelial cells (PBMEC #1 and PBMEC #2) or primary BM stromal cells (PBMSC #1 and PBMSC #2) isolated from same MM patient. Results are means±SD for assays performed in triplicate. Statistical significance of differences between groups was determined by unpaired Student's t-test. CM was taken after 72 hrs culture.
(FIG. 4H) Representative immunohistochemical stains of CyPA and CyPB expression in BM from healthy subjects (NBM) (n=20) and MM patients (n=60) (MMPT). Black and yellow arrows indicate expression of CyPA or CyPB in BMECS and myeloid cells, respectively, in a NBM. ELISA quantification of eCyPA (FIG. 4I) and eCyPB (FIG. 4J) levels in serum from BM and PB isolated from same MM patients (n=12).
Figure 4C:
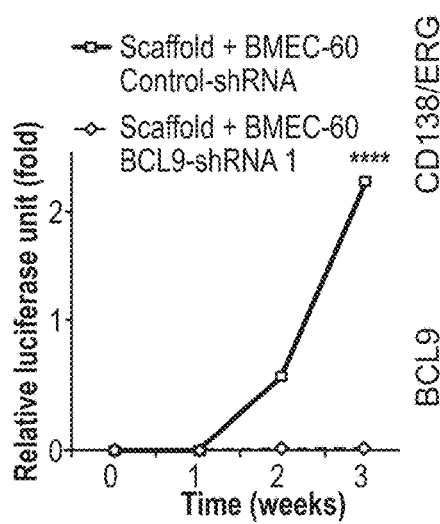
Figure 4D:
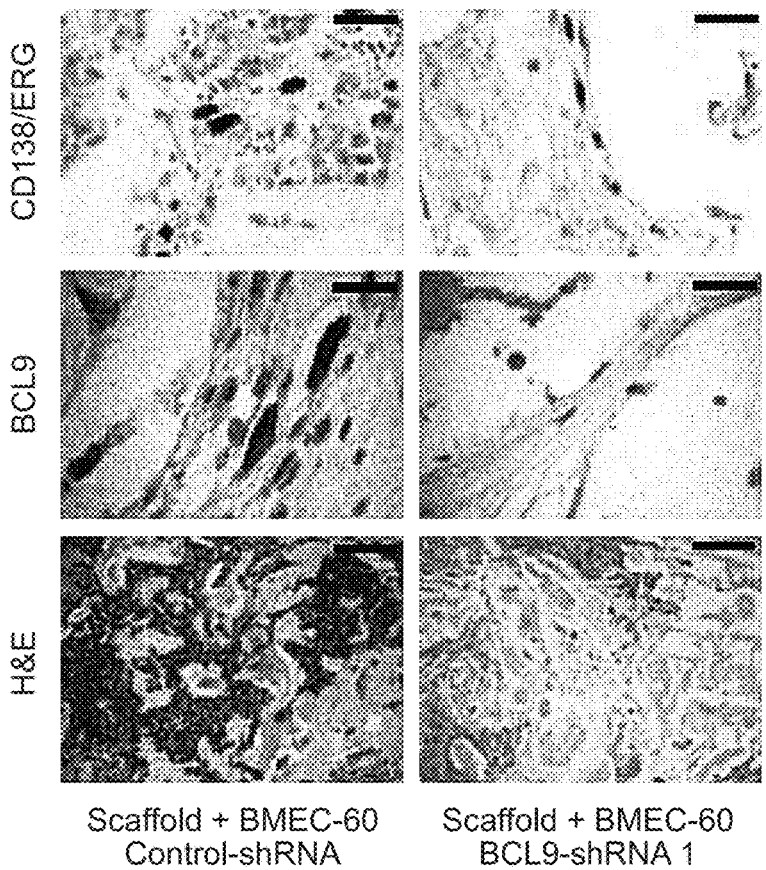
Figure 10B:
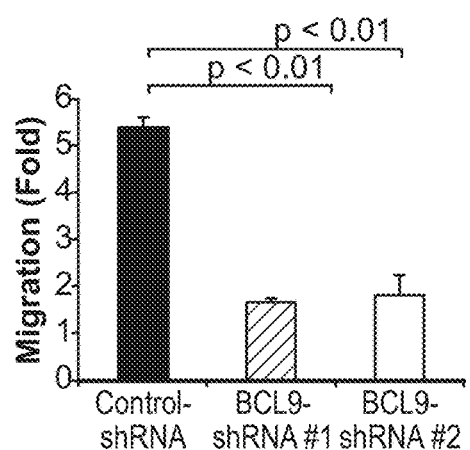
(FIG. 10B) Transwell migration of H929 cells co-cultured with BMEC-1 cells lentivirally transduced with Control-shRNA or BCL9-shR-NAs.
Figure 10C:
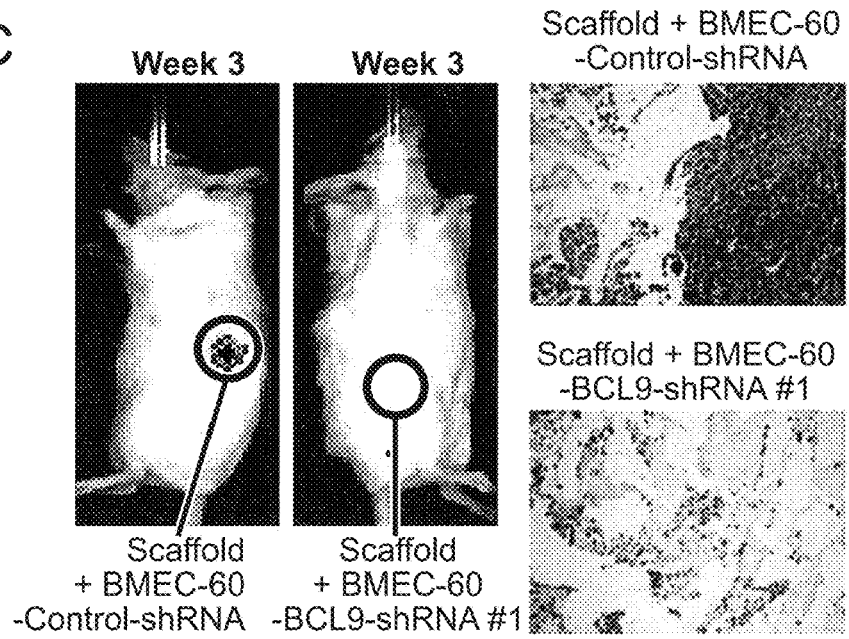
(FIG. 10C) and (FIG. 10D) display data from two experiments shown in FIGS. 4B-D. Xenogen data (FIG. 10E), time course (FIG. 10F), and histologic analysis (FIG. 10G) of H929-luc cell growth within scaffolds coated with BMEC-60 cells lentivirally transduced with Control-shRNA or BCL9-shRNA #2.
Figure 10D:
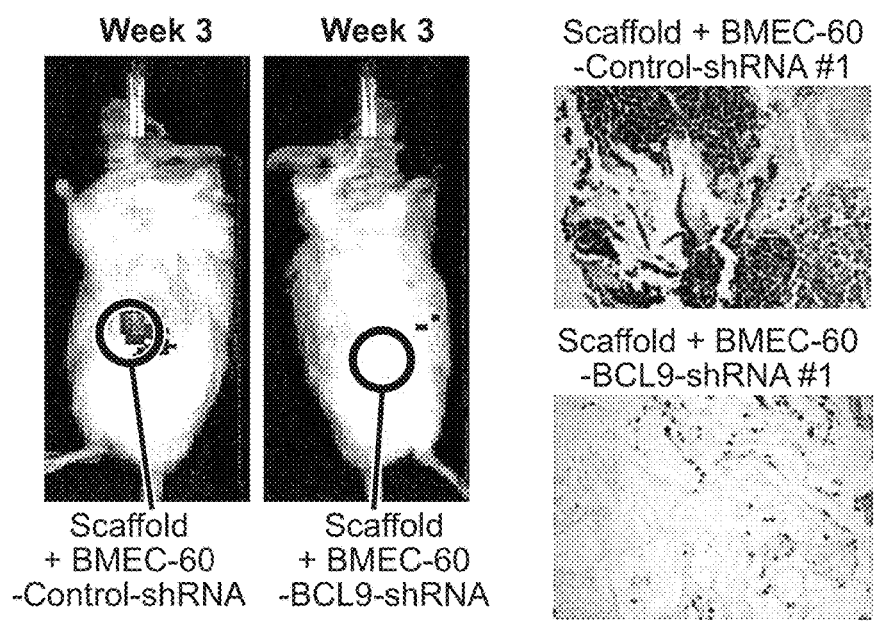
FIG. 10.
(FIG. 10H) Silver-stained agarose gels of proteins secreted by BMEC-60 cells lentivirally transduced with Control-shRNA or BCL9-shRNAs, PBMEC #1, PBMSC #1 or HS5 cells. Bars indicate low-molecular weight bands present in CM from BMEC-60 cells transduced with control-shRNA but not transduced with BCL9-shRNA, which were excised and analyzed by mass spectrometry.
(FIG. 10I) Immunoblot analysis of BCL9, CyPA and CyPB expression in total protein extracts from BMEC-60 cells transduced with control-shRNA or BMEC-60 cells transduced with BCL9-shRNAs.
Figure 10E:
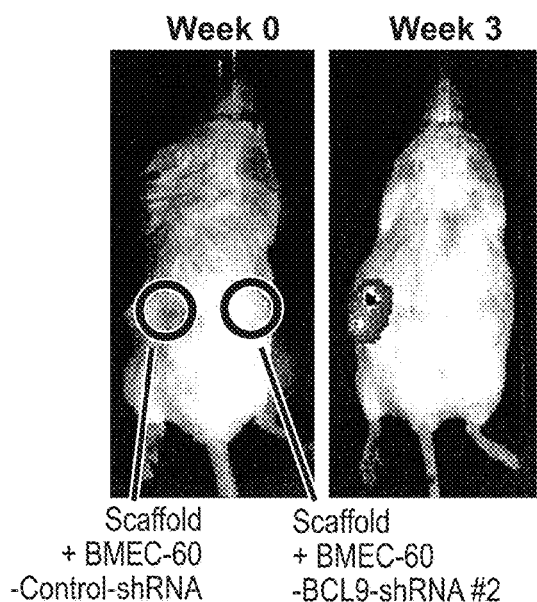
Figure 10F:
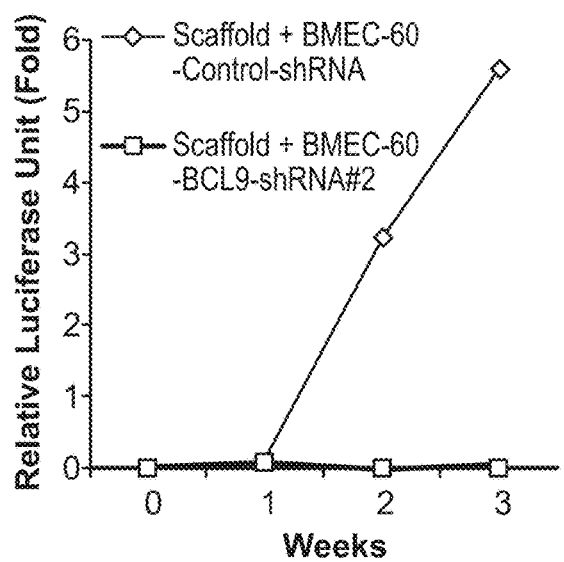
Figure 10G:
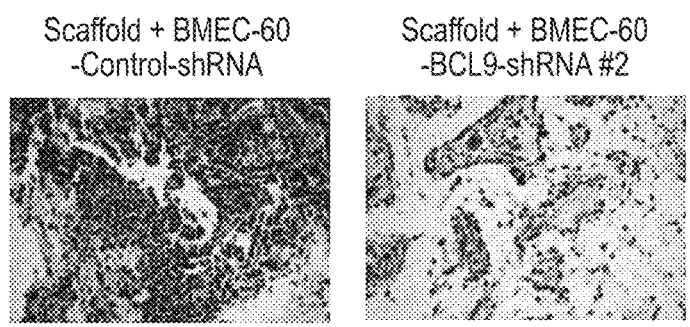

We knocked down expression of BCL9 in BMECs (FIG. 9B) to investigate whether BCL9 was needed to promote the migration and growth of MM cells. In vitro migration of MM1S-luc (FIG. 4A) and H929 cells (FIG. 10B) was significantly reduced when co-cultured with BMEC-60 or BMEC-1 cells lentivirally transduced with BCL9-shRNAs. In vivo migration and growth of MM1S-luc cells within scaffolds were also inhibited when BMEC-60 cells were lentivirally transduced with BCL9-shRNA. Migration and growth were similarly observed within control scaffolds coated with BMEC-60 cells lentivirally transduced with control shRNAs (FIGS. 4B, C and 10C, D). Histological and immunohistochemical analysis at the end of the experiment confirmed uniform scaffold coating by both BMEC-60-control-shRNA (FIG. 4D top) and BMEC-60-BCL9-shRNA (FIG. 4D, bottom) cells, as well as the absence of MM1S-luc cells in scaffolds coated with BMEC-60-BCL9-shRNA cells, ruling out the possibility that the decrease in growth of MM cells within the scaffolds when coated with BMEC-60 cells transduced with BCL9-shRNA is due to a proportionally decrease in number of cells as a consequence of a decrease in endothelial cell proliferation (FIG. 21). Similar results were observed with luciferase-labeled H929 cells using scaffolds coated with BMEC-60 cells (FIGS. 10E-G).

Figure 10H:
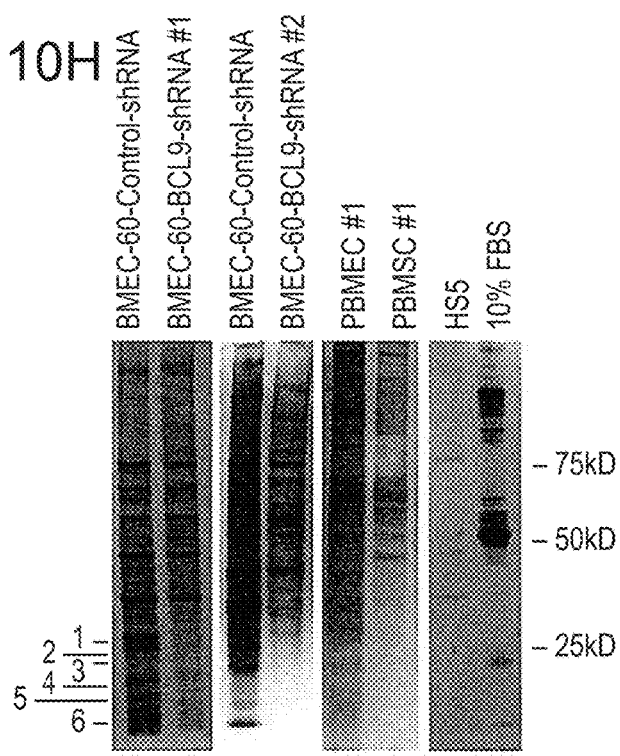
Figure 10I:
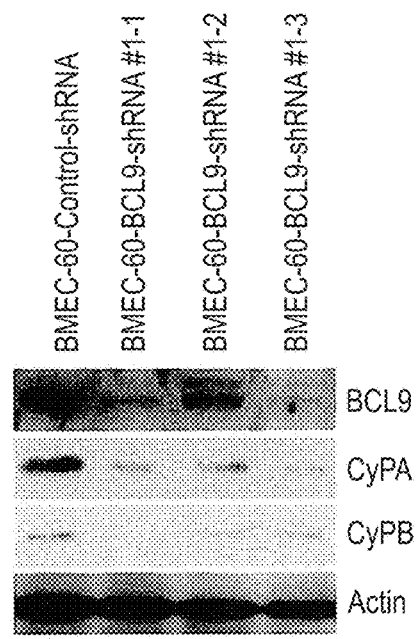

Example 6 Proteomic Analysis Identifies eCyPA and eCyPB as Signaling Factors Secreted by BMECs The foregoing results prompted us to perform proteomic analysis to identify signaling molecules secreted by BMECs, whose expression is regulated by BCL9, and that promote chemoattraction, migration, and proliferation of MM cells. Silver-stained agarose gels revealed qualitative and quantitative differences, particularly among lower-molecular weight proteins, in CM from BMEC-60 cells lentivirally transduced with control-shRNAs or BCL9-shRNAs, as compared with medium alone. The same was observed in HS5 cells, indicating secretion of a discrete protein by the control BMEC-60 cells, but not the others (FIG. 10H). The absence of lower-molecular weight bands after 1 hr of incubation (data not shown) in the presence or absence of 10% fetal bovine serum (FBS) rules out the possibility that these differences are related to FBS. To identify the low-molecular weight proteins (<28 kD) secreted by BMEC-60 cells, we performed proteomic analysis of the six major bands (bands 1 to 6) with molecular weights of <28 kD from silver-stained gels (FIG. 4E, blue), as well as analysis of whole CM from BMEC-60 (FIG. 4E, pink), PBMEC #1 (FIG. 4E, yellow), and PBMEC #2 (FIG. 4E, green) cells.

Figure 4E:
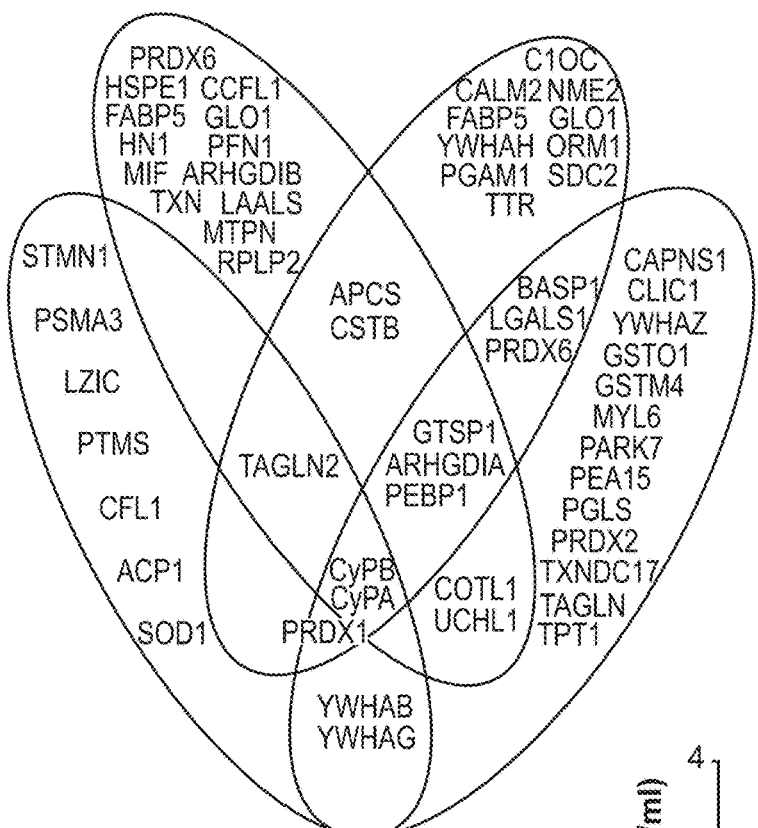
Figure 4F:
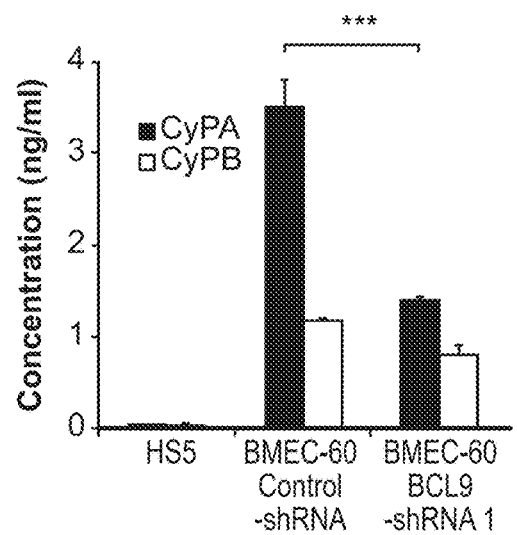
Figure 4G:
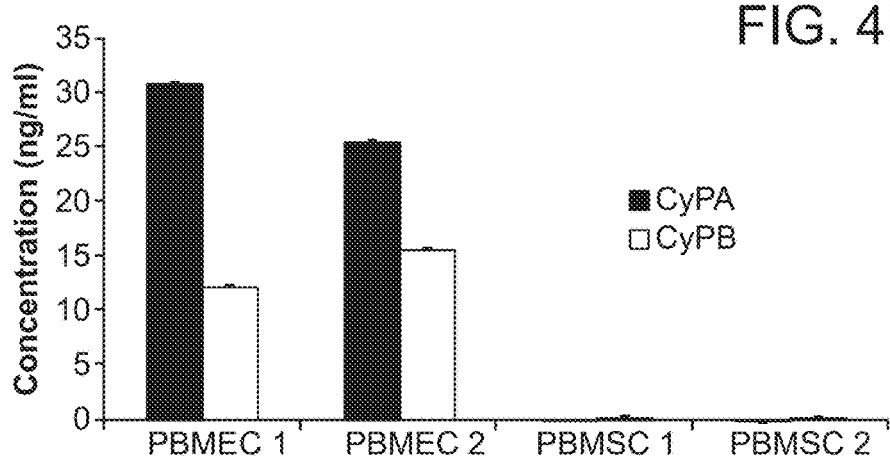
Figure 4H:
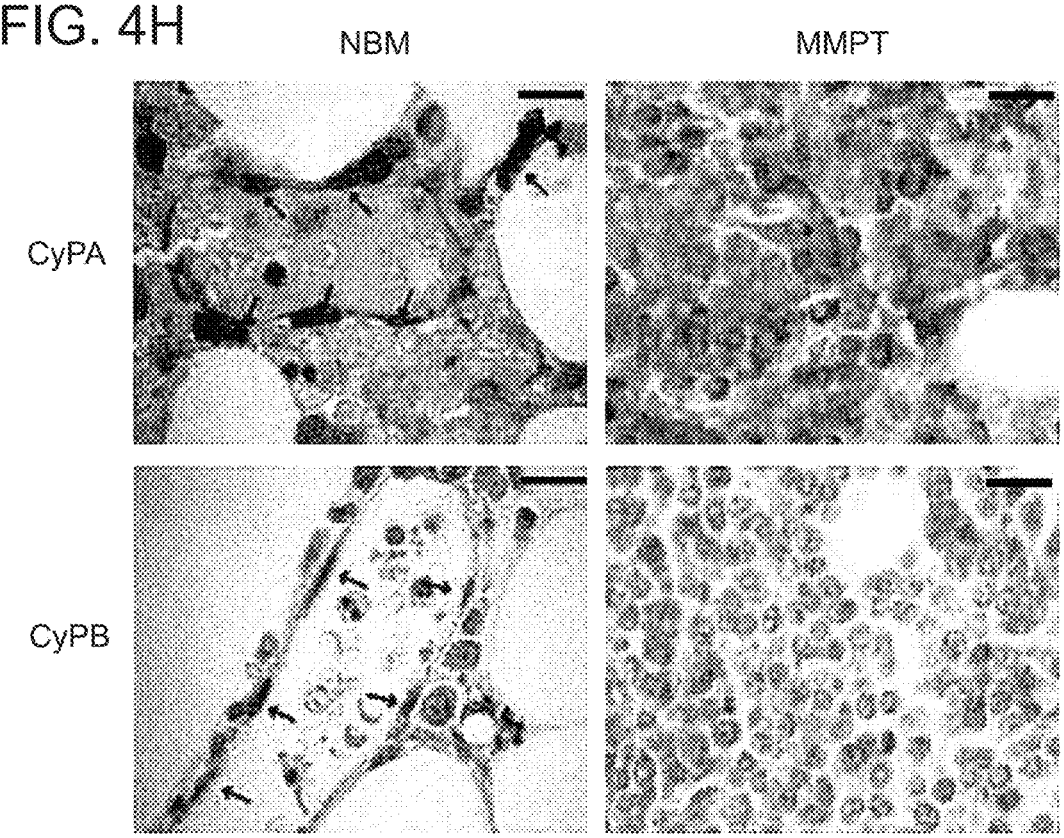

Both procedures provided a large number of potential candidates with molecular weights of <28 kD that are known to be secreted into media, have known signaling functions, and were detected by both procedures in BMEC-60 as well as in primary BMECs. Among these, the most likely candidates in all cell supernatants were eCyPA and eCyPB (FIG. 4E, intersection and Tables 2 and 3 below). ELISA assays confirmed the presence of eCyPA and eCyPB in CM from BMEC-60-control-shRNA cells, and showed that eCyPA and eCyPB secretion were markedly decreased in BEMC-60-BCL9-shRNA and almost absent in CM from HS5 cells (FIG. 4F). ELISA assays also showed that primary BMECs secrete much more eCyPA than primary BMSCs isolated from the same MM patient (FIG. 4G). In addition, BMEC-60 cells and primary BMECs secreted much more eCyPA than eCyPB when compared with HS5 and primary BMSCs (FIGS. 4F, 4G). Immunoblot analysis of several batches of lentivirally transduced BMEC-60 cells confirmed stable BCL9 knockdown and concomitantly decreased cellular CyPA and CyPB expression in BMEC-60-BCL9-shRNA cells relative to controls (FIG. 10H), indicating that CyPA and CyPB, which are members of the same family of proteins, have overlapping signaling functions 33 and are both transcriptional targets of BCL9. Only cells with >70% knockdown of BCL9 expression were selected for in vitro and in vitro assays. Cellular CyPA and CyPB expression was also examined by immunoblot analysis in other purified BMECs including BMEC-1 cells, primary BMECs, and primary BMSCs from the same MM patient (FIGS. 1C and 9D), and by immunohistochemical analysis of BM biopsies from healthy subjects (FIGS. 4H, left and 11A). These experiments confirmed that most BMECs express significant levels of CyPA, and that CyPB expression is decreased compared with CyPA.

TABLE 2

Proteomics Analysis of BMEC-60

Proteomics Analysis of Silver Stained Gel Bands

|  | Gene Symbol | Description | MW |
|---|---|---|---|
| Band 1 | YWHAB | Tyrosine 3-Monooxygenase/14-3-3 protein beta/alpha | 28092 Da |
|  | YWHAG | Tyrosine 3-Monooxygenase/14-3-3 protein gamma | 28393 Da |
|  | PSMA3 | Proteasome subunit alpha type-3 | 28433 Da |
| Band 2 | TAGLN2 | Transgelin 2 | 22391 Da |
|  | PRDX1 | Peroxiredoxin 1 | 22110 Da |
|  | LZIC | Leucine Zipper And CTNNBIP1 Domain Containing | 21485 Da |
| Band 3 | CyPB | Peptidylprolyl isomerase B precursor (PPIB) | 23743 Da |
|  | PRDX1 | Peroxiredoxin 1 | 22110 Da |
|  | TAGLN2 | Transgelin 2 | 22391 Da |
| Band 4 | TAGLN2 | Transgelin 2 | 22391 Da |
|  | CFL1 | Cofilin 1 (non-muscle) | 18502 Da |
|  | GGCT | Gamma-glutamylcyclotransferase | 21008 Da |
| Band 5 | STMN1 | Stathmin 1 | 17303 Da |
|  | CyPA | Peptidylprolyl isomerase A (PPIA) | 18012 Da |
|  | SOD1 | Superoxide dismulase 1, soluble | 15936 Da |
| Band 6 | STMN1 | Stathmin 1 | 17393 Da |
|  | ACP1 | Acid Phosphatase 1, Soluble | 18042 Da |
|  | SOD1 | Superoxide dismulsae 1, soluble | 16936 Da |

Whole Proteomics Analysis

| Gene Symbol | Description | MW |
|---|---|---|
| APCS | Serum amyloid P component precursor | 25387 Da |
| PRDX6 | Peroxiredoxin 6 | 25036 Da |
| UCHL1 | Ubiquitin carboxyl-terminal esterase L1 | 24824 Da |
| CyPB | Peptidylprolyl isomerase B precursor (PPIB) | 23743 Da |
| GSTP1 | Glutathione transferase | 23356 Da |
| ARHGDIA | Rho GDP dissociation inhibitor (GDI) alpha | 23207 Da |
| ARHGDIB | Rho GDP dissociation inhibitor (GDI) beta | 22988 Da |
| TAGLN2 | Transgelin 2 | 22391 Da |
| PEBP1 | Prostatic binding protein | 21057 Da |
| GLO1 | Glyoxalase 1 | 20778 Da |
| HN1L | Hermatological and neurological expressed 1-like | 20083 Da |
| CFL1 | Cofilin 1 (non-muscle) | 13502 Da |
| CyPA | Peptidylprolyl isomerase A (PPIA) | 16012 Da |
| COTL1 | Coactosin-like 1 | 15945 Da |
| SOD1 | Superoxide dismulase 1, soluble | 15938 Da |
| FABP6 | Fatty Acid binding protien 5 (psoriasis-associated) | 16164 Da |
| PFN1 | Profilin 1 | 15054 Da |
| LGALS1 | Galectin-1 | 14716 Da |
| MTPN | Myotrephin | 12895 Da |
| MIF | Macrophage migration inhibitory factor | 12470 Da |
| TXN | Thioredoxin | 11737 Da |
| RPLP2 | Ribosomal protein P2 | 11665 Da |
| CSTB | Cystatin B | 11140 Da |
| HSPE1 | Heat Shock 10 kDa protein 1 | 10932 Da |

TABLE 3

Proteomics Analysis of PBMEC #1 and PBMEC #2

| Gene Symbol | Description | MW |
|---|---|---|
| Whole Proteomics Analysis of PBMEC #1 | | |
| CyPA | peptidylprolyl isomerase A | 18012 Da |
| TXNDC17 | thioredoxin-like 5 | 13941 Da |
| CLIC1 | chloride intracellular channel 1 | 26923 Da |
| MYL6 | myosin, light chain 6; alkali smooth muscle and non-muscle isoform 1 | 16930 Da |
| UCHL1 | ubiquitin carboxyl-terminal esterase L1 | 24824 Da |
| COTL1 | coactosin-like 1 | 15945 Da |
| BASP1 | brain abundant, membrane attached signal protein 1 | 22693 Da |
| PARK7 | Parkinson disease protein 7 | 19891 Da |
| PRDX2 | peroxiredoxin 2 isoform a | 21785 Da |
| GSTM4 | glutathione S-transferase mu 4 isoform 1 | 25561 Da |

TABLE 3-continued

Proteomics Analysis of PBMEC #1 and PBMEC #2

| Gene Symbol | Description | MW |
|---|---|---|
| GSTP1 | glutathione transferase | 23356 Da |
| LGALS1 | galectin-1 | 14716 Da |
| PRDX1 | peroxiredoxin 1 | 22110 Da |
| PEBP1 | prostatic binding protein | 21057 Da |
| PEA15 | phosphoprotein enriched in astrocytes 15 | 16040 Da |
| TPT1 | Tumor protein, transtationally-controlled 1 | 19596 Da |
| YWHAZ | Tyrosine 3/tryptophan 5-monooxygenase activation protein, zeta | 27771 Da |
| ARHGDIA | Rho GDP dissociation inhibitor (GDI) alpha | 23207 Da |
| GSTO1 | Glutathione-S-transferase omega 1 | 27560 Da |
| PRDX6 | Peroxiredoxin 6 | 25035 Da |
| TAGLN | Transgelin | 22611 Da |
| PGLS | 6-phosphogluconolactonase | 27547 Da |
| CyPB | Peptidylprolyl isemerase B precursor | 25743 Da |
| YWHAB | Tyrosine 3-Monooxygenase/14-3-3 protein beta/alpha | 28062 Da |
| YWHAG | Tyrosine 3-Monooxygenase/14-3-3 protein gamma | 28303 Da |
| CAPNS1 | Calpain, small subunit 1 | 28316 Da |
| Whole Proteomics Analysis of PBMEC #2 | | |
| CyPA | Peptidylprolyl isomerase A | 18012 Da |
| ORM1 | Orosomucoid 1 precursor | 23512 Da |
| BASP1 | Brain abundant membrain attached signal protein 1 | 22693 Dd |
| SDC2 | Syndecan 2 precursor | 22160 Da |
| APCS | Serum amyloid P component precursor | 25567 Da |
| CALM2 | Calmodutin 2 | 16838 Da |
| CSTB | Cystatin B | 11140 Da |
| GSTP1 | Glutathione transferase | 23356 Da |
| LGALS1 | Galactin-1 | 14716 Da |
| PRDX1 | Peroxirodoxin 1 | 22110 Da |
| PEBP1 | Prostatic binding protein | 21057 Da |
| TAGLN2 | Transgelin 2 | 22591 Da |
| TTR | Tranethyrolin precursor | 16887 Da |
| YWHAH | Tyrosine 3-Monooxygenase/14-3-3 protein eta | 28219 Da |
| ARHGDIA | Rho GDP dissociation inhibitor (GDI) alpha | 23407 Da |
| PROX6 | Peroxiredoxin 6 | 25035 Da |
| CyPB | Peptidylprolyl isomerase B precursor | 25745 Da |
| C1QC | Complement component 1, q subcomponent, C chain precursor | 25774 Da |
| NME2 | Nucleoside diphosphate kinase B | 17298 Da |
| PGAM1 | Phosphoglycerate mutase 1 [*Homo sapiens*] | 26804 Da |

Figure 11A:
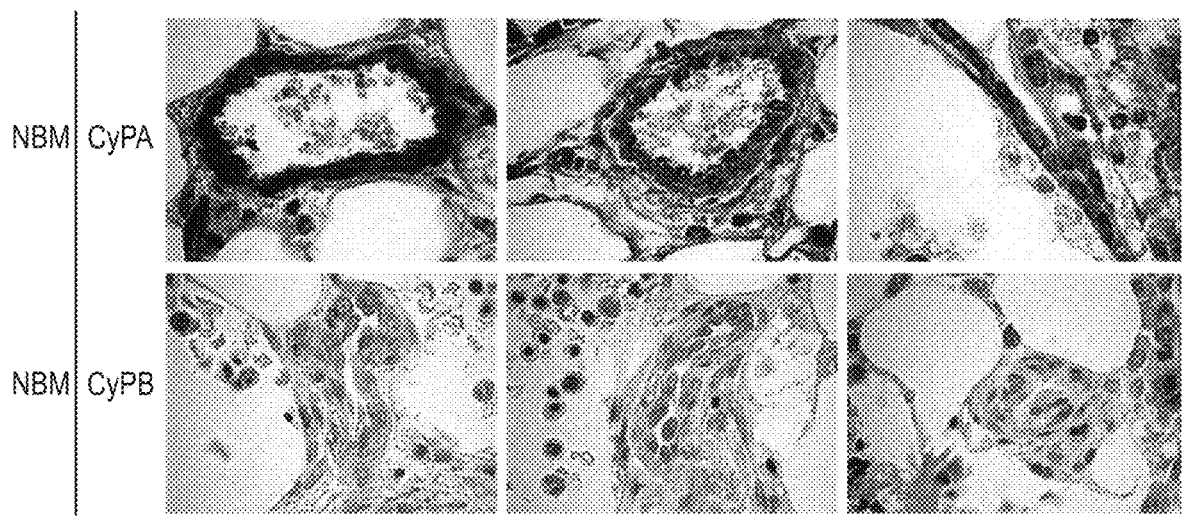
(FIG. 11A) Representative CyPA (top) and CyPB (bottom) immunostains in normal bone marrows (n=20).
Figure 11B:
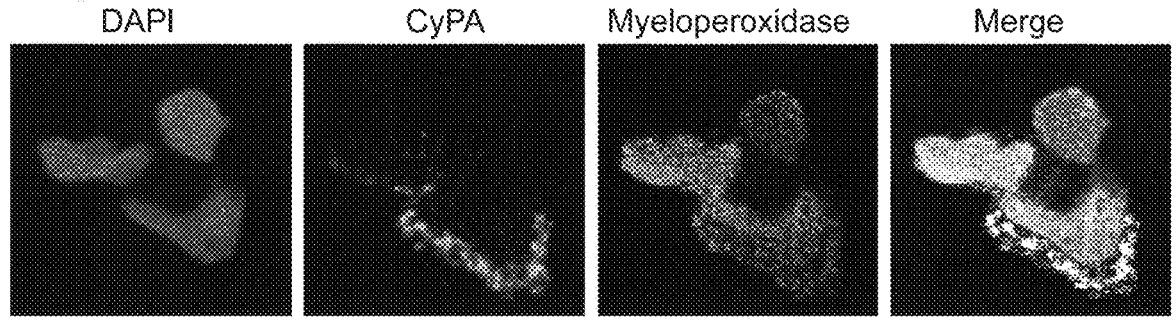
(FIG. 11B) Double immunofluorescence analysis of CyPA (green) and myeloperoxidase (red) expression in BM aspirate from normal individual.
Figure 11C:
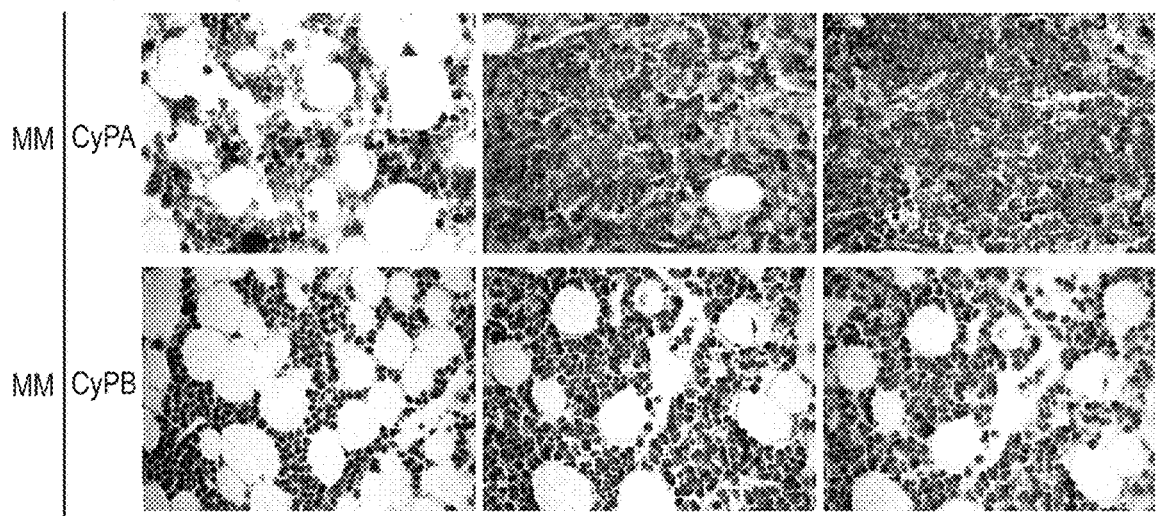
(FIG. 11C) Representative CyPA (top) and CyPB (bottom) immunostains in BM from MM patients (n=60).
Figure 11D:
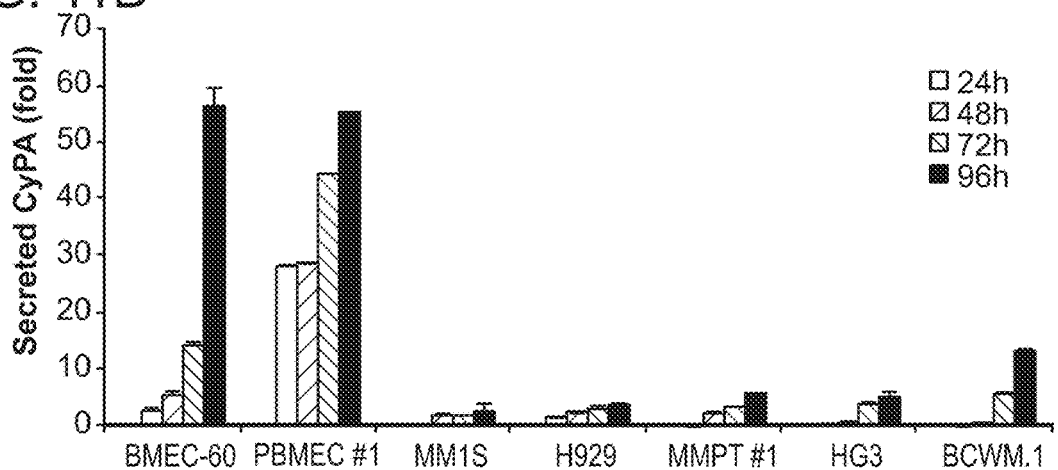
(FIG. 11D) Time course ELISA analysis of CyPA secretion by the indicated cells. $5\times10^5$ cell were plated in each case. Results are means±SD for assays performed in triplicate.
Figure 12A:
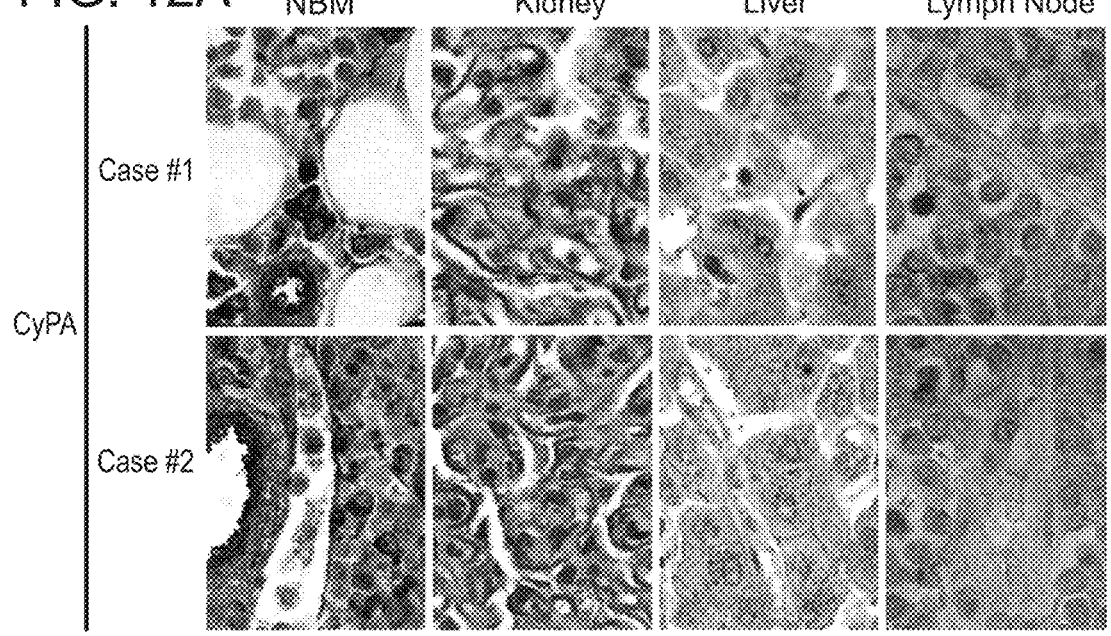
(FIG. 12A) CyPA immunostains in two different NBM, kidney, liver, and lymph node biopsies from healthy subjects.

Immunohistochemical studies also revealed that BM myeloid cells express significant amounts of CyPA, but not CyPB (FIGS. 4H, 11B); hence, myeloid cells could be an additional source of eCyPA, but not of eCyPB, in the BM niche. In addition, immunohistochemical studies revealed that although MM cells expressed CyPA (FIGS. 4H, right and 11C), they secreted it at very low levels in comparison with BMECs, or did not do so at all (FIG. 11D). Furthermore, immunohistochemical analysis revealed much lower CyPA expression in endothelial cells from other tissues including kidney, liver, and lymph nodes than in BMECs (FIG. 12A).

Figure 4I:
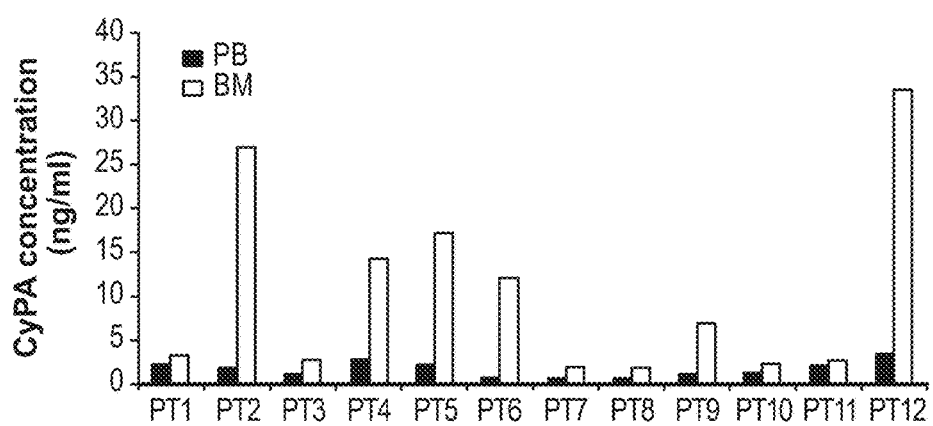
Figure 4J:
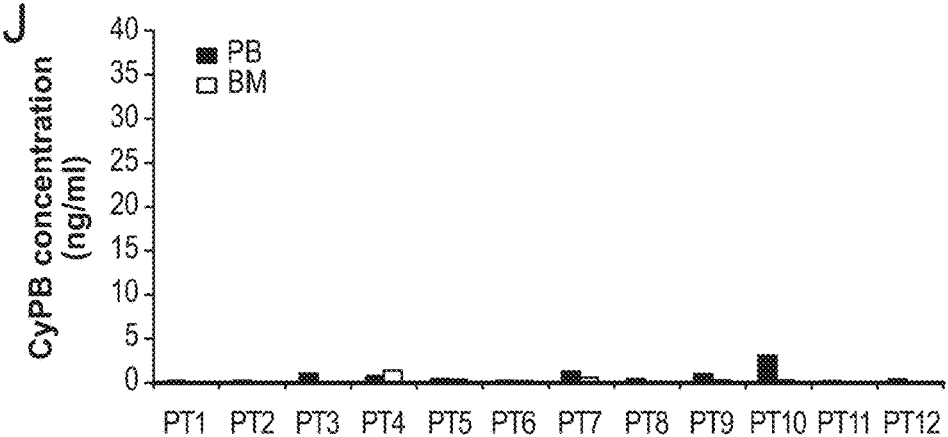
Figure 12B:
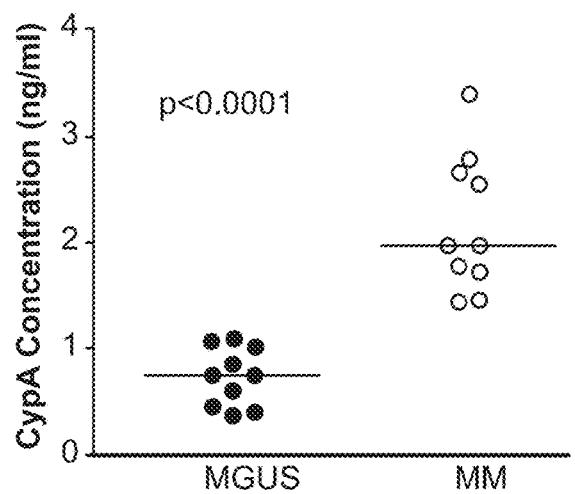
(FIG. 12B) Serum levels of eCyPA in 10 BM aspirates from MGUS and MM patients.
Figure 17:
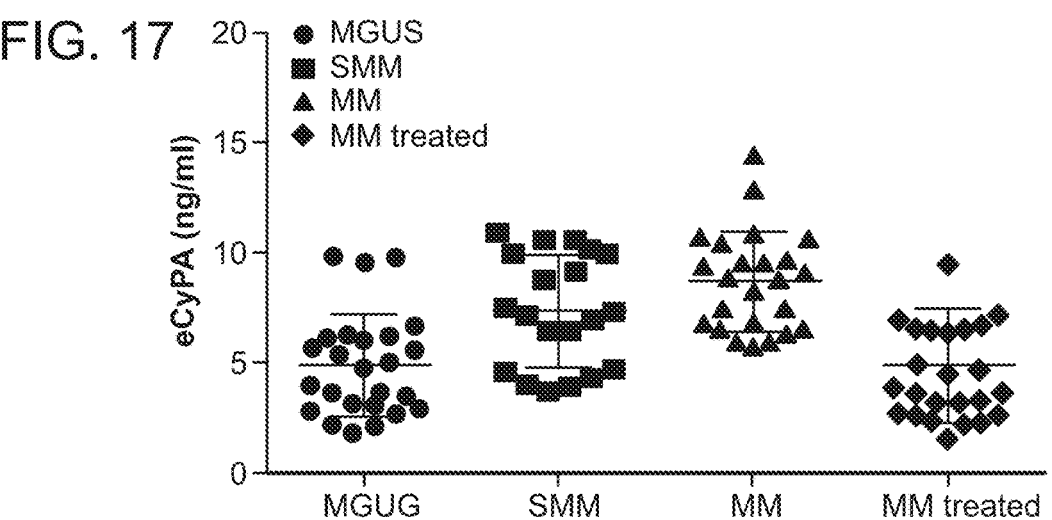
FIG. 17 is a graphical representation of an ELISA assay showing eCyPA (ng/ml) in peripheral blood serum from four different patent groups—MGUS, SMM, MM and MM treated (n=25 per group). eCyPA level is correlated with progress of multiple myeloma, from MGUS to MM stage and is decreased after treatment. eCyPA could use a biomarker to monitor MM progress. MGUS: Monoclonal gammopathy of unknown significance; SMM: Smoldering multiple myeloma; MM: multiple myeloma; MM treated: patient under treatment.

The foregoing results prompted us to next examine serum levels of eCyPA and eCyPB in MM patients. To this end, serum from BM and PB collected from the same patient at the time of diagnosis were analyzed by ELISA. As shown in FIG. 4I, in MM patients (n=12) eCyPA was significantly more abundant in BM serum than in serum from PB (BM: 10.54 ng/ml.+−0.10.72; PB: 1.59 ng/ml.+−0.0.94) ($P<0.0087$). In the same samples, serum levels of eCyPB were much lower than those of eCyPA (BM: $P<0.0032$; PB: $P<0.0125$), and no major differences were detected between BM and PB (FIG. 4J). In addition, eCyPA levels in PB serum were significantly higher in MM than MGUS patients (FIG. 12B).

eCyPA levels were also examined in MGUS, SMM, MM patients, and MM treated patients. FIG. 17 is a graphical representation of an ELISA assay showing eCyPA (ng/ml) in peripheral blood serum from four different patent groups—MGUS, SMM, MM and MM treated (MGUS: Monoclonal gammopathy of unknown significance; SMM: Smoldering multiple myeloma; MM: multiple myeloma; MM treated: patient under treatment, n=25 per group). Serum eCyPA level correlated with progress of multiple myeloma, from MGUS to MM stage, and is decreased after treatment. These results show eCyPA can be used a biomarker to monitor MM progress.

Figure 5A:
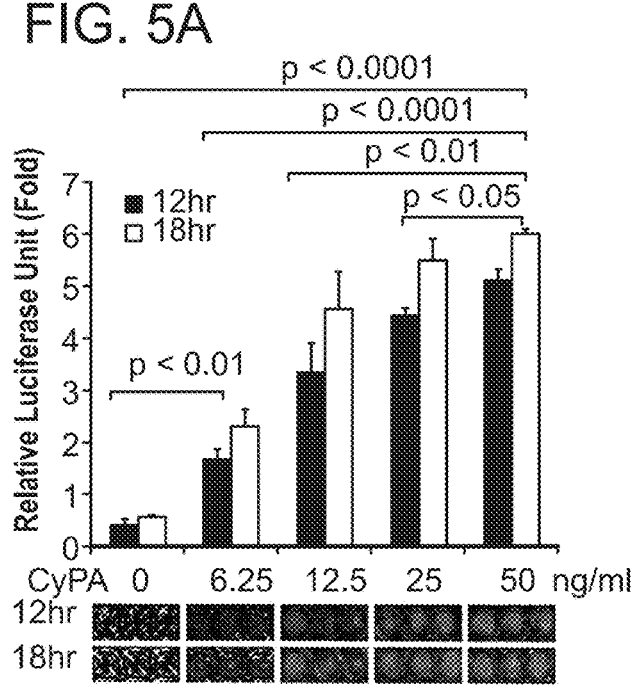
(FIG. 5A) increased concentrations of recombinant eCyPA.
Figure 5B:
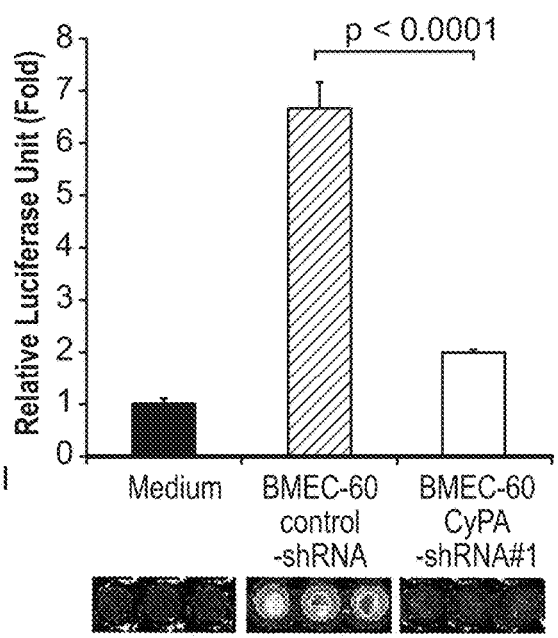
(FIG. 5B) medium alone or BMEC-60 cells lentivirally transduced with Control-shRNA or shRNAs against CyPA (CyPA-shRNA). Migration data was normalized based on data of medium alone. Results are means±SD for assays performed in triplicate. Statistical significance of differences between groups was determined by unpaired Student's t-test.
Figure 5C:
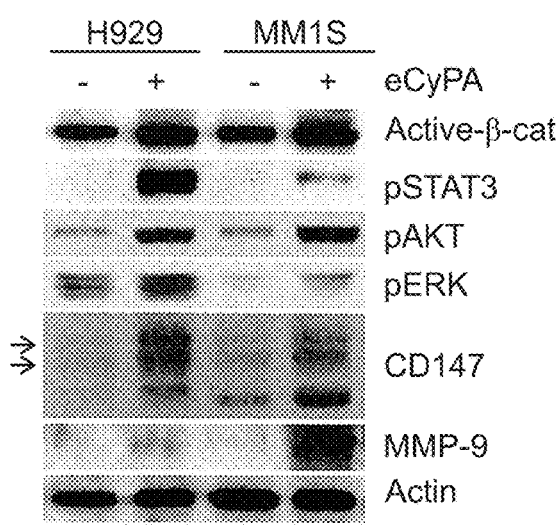
(FIG. 5C) Immunoblot of total protein extracts from H929 and MM1S cells incubated in the absence (−) or presence (+) of eCyPA at 50 ng/ml.
Figure 5D:
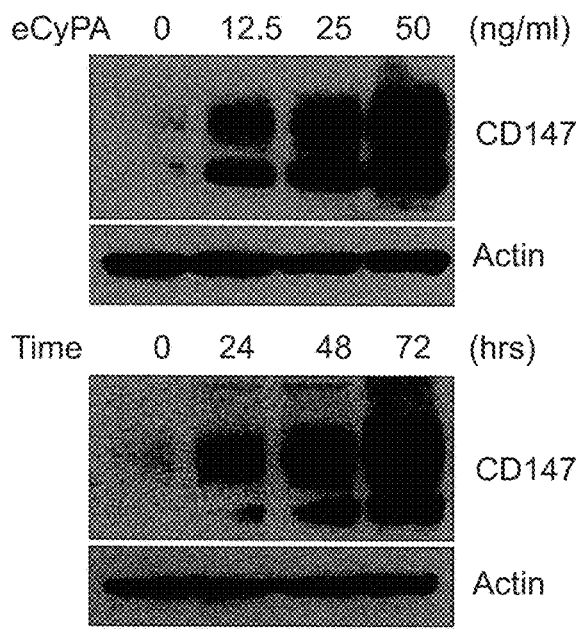
(FIG. 5D) Immunoblot of total protein extracts from MM1S cells treated with increasing concentrations of recombinant eCyPA (top) or 50 ng/ml of recombinant eCyPA for different times (bottom).
Figure 5E:
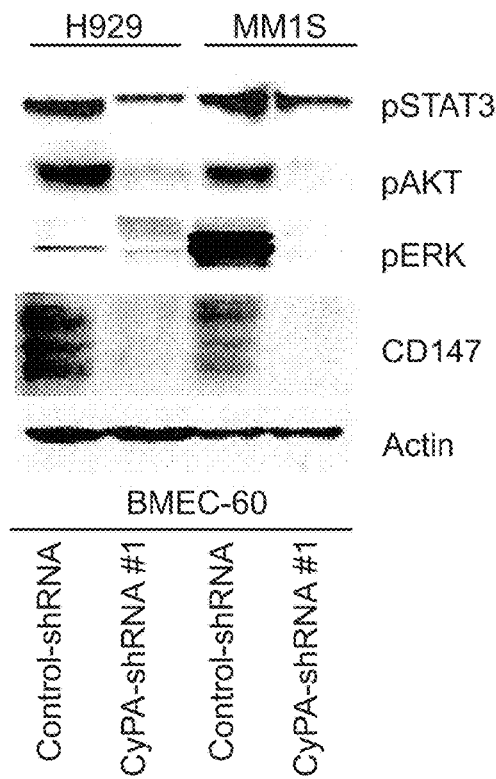
(FIG. 5E) Immunoblot of total protein extracts from H929 and MM1S cells incubated with BMEC-60 cells lentivirally transduced with Control-shRNA or CyPA-shRNA.
Figure 5F:
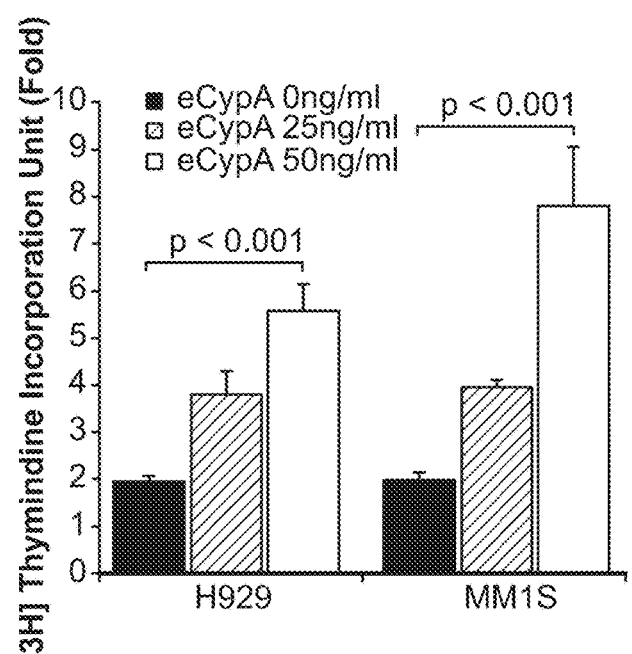
(FIG. 5F) Proliferation analysis of H929 and MM1S cells incubated in the absence or presence of increasing concentrations of eCyPA. Xenogen data (FIG. 5G), time course (FIG. 5H), and histologic analysis (FIG. 5I) of MM1S-luc cell growth within scaffolds coated with BMEC-60 lentivirally transduced with Control shRNAs or CyPA-shRNA. Statistical analyses of tumor burden were done using factorial analysis in SPSS 13.0. The results of one representative of three independent experiments is shown.
Figure 12C:
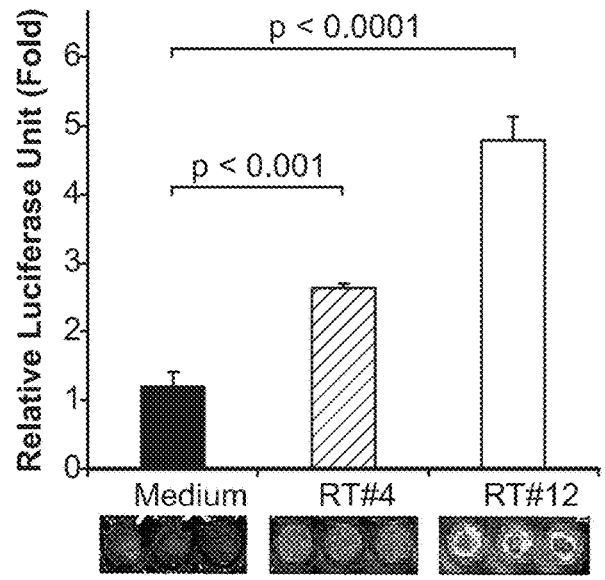
(FIG. 12C) Transwell migration assay of MM1S-luc cells incubated in the absence of serum (Medium) or BM serum from two different MM patients with low (PT #4) and high (PT #12) levels of eCyPA (same as FIG. 4I). Migration data was normalized based on data of medium alone.
Figure 12D:
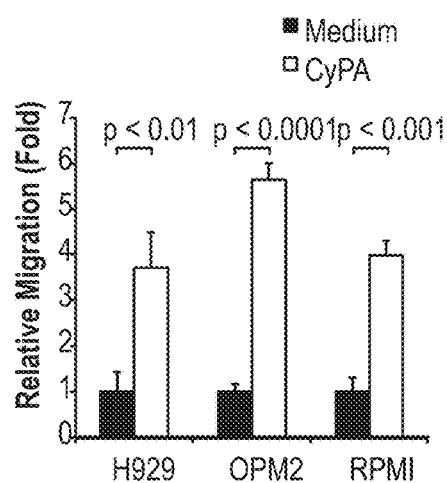
(FIG. 12D) Transwell migration assay of H929, OPM2 and RPMI cells incubated with medium alone or in the presence of 50 ng/ml of recombinant eCyPA.
Figure 12E:
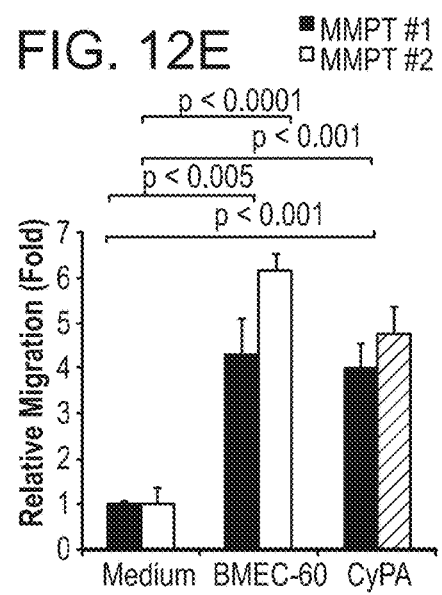
(FIG. 12E) Transwell migration assay of two MM primary tumors (MMPT #1 and MMPT #2) incubated with medium alone or 50 ng/ml of recombinant eCyPA or BMEC-60 cells.
Figure 13A:
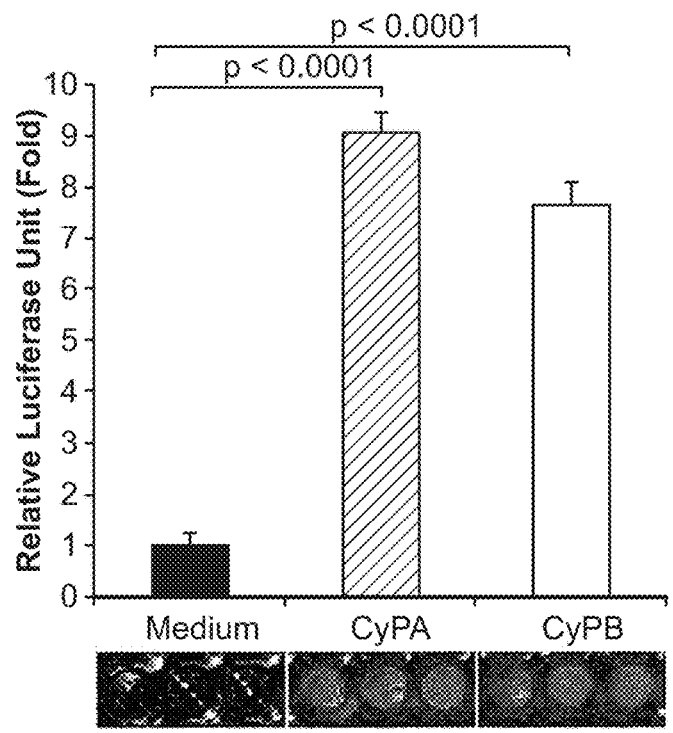
(FIG. 13A) Transwell migration assay of MM1S-luc cells incubated with medium alone or 50 ng/ml of recombinant eCyPA or eCyPB.
Figure 13B:
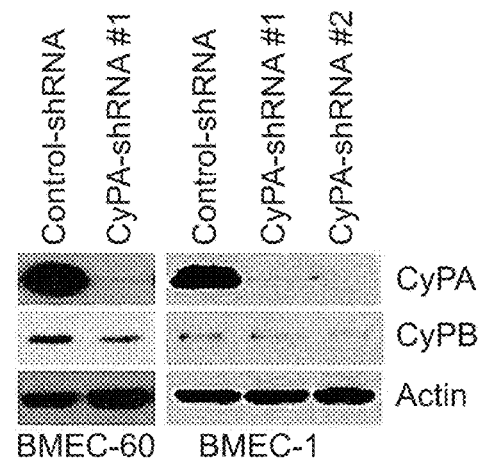
(FIG. 13B) Immunoblot of CyPA and CyPA expression in BMEC-60 and BMEC-1 cells lentivirally transduced with control-shRNAs or CyPA-shR-NAs.
Figure 13C:
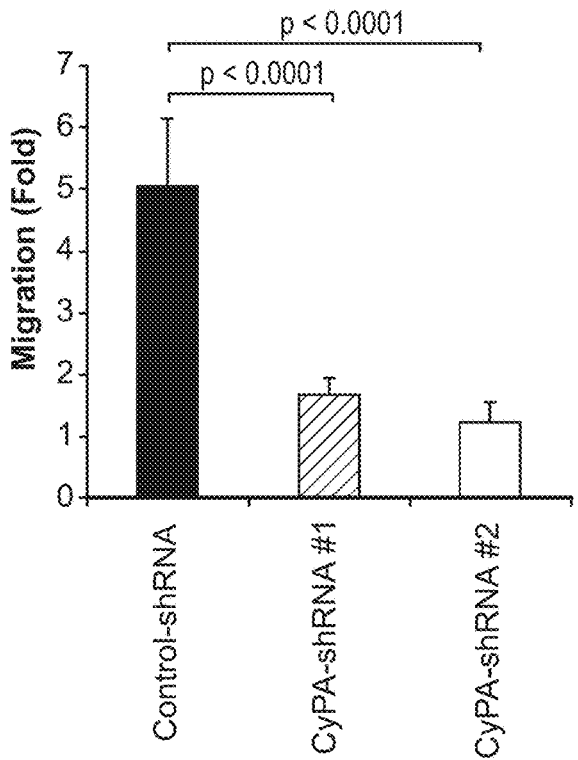
(FIG. 13C) Transwell migration assay of MM1S cells co-cultured with BMEC-1 cells lentivirally transduced with control-shRNA or CyPA-shRNAs.
Figure 13D:
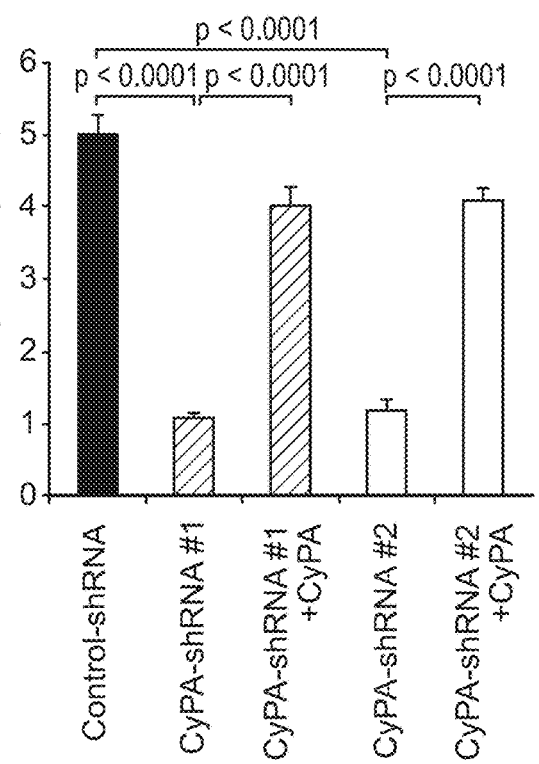
(FIG. 13D) Transwell migration assay of MM cells co-cultured with BMEC-1 cells lentivirally transduced with control-shRNA or CyPA-shR-NAs, in the absence or presence of 50 ng/ml of recombinant eCyPA.
Figure 13E:
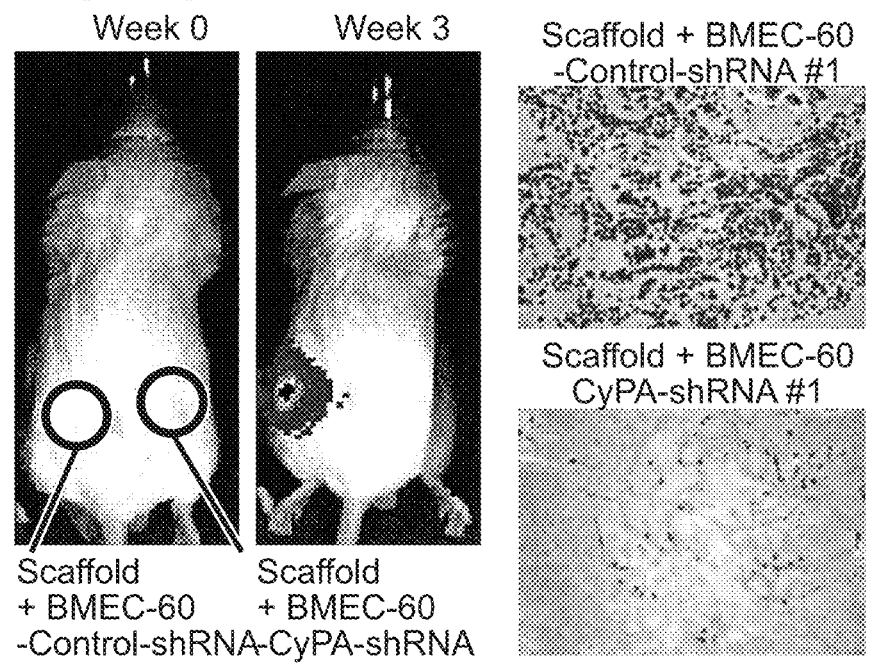
(FIG. 13E) Top and bottom, two independent experiments with results shown in FIGS. 5G-I. Xenogen (FIG. 13F), time course (FIG. 13G) and histological analysis (FIG. 13H) of H929-luc cell growth in scaffolds coated with BMEC-60 cells lentivirally transduced with control-shRNA or CyPA-shRNA #1.
Figure 13E:
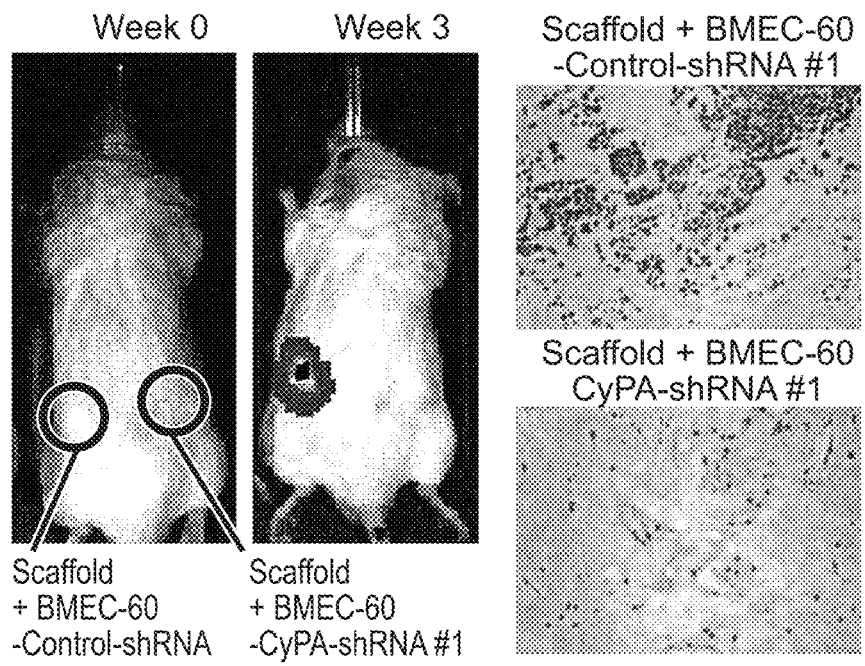

Example 7 eCvPA Promotes Migration, Proliferation and Bone Marrow Homing of Multiple Myeloma Cells Because of the documented role of CyPA in neutrophil migration, it was of interest to further probe the role of eCyPA in MM cell migration in vitro and in vivo. As shown in FIG. 5A, purified recombinant eCyPA promoted migration of MM1S-luc cells in a time- and concentration-dependent manner. Although maximal responses were observed at 50 ng/ml, which was used in subsequent assays, significant migration was induced at CyPA concentrations at as low as 6 ng/ml, which is typically found in the BM serum of MM patients (FIG. 4I). The observation of increased serum levels of eCyPA levels in the BM serum of MM patients prompted us to examine whether BM serum from MM patients increased migration. As shown in FIG. 12C, transwell assays revealed that BM serum from MM patients promoted migration of MM1 S-luc cells to an extent that varied with the concentration of eCyPA. Recombinant CyPA also induced migration of other MM cell lines (i.e. H929, OPM2, and RPMI) (FIG. 12D) as well as primary MM cells (FIG. 12E). No major differences in migration were observed between primary MM cells incubated in the presence of BMEC-60 cells incubated with 50 ng/ml CyPA (FIG. 12E). Major differences were likewise not observed in the migration of MM1S-luc cells treated with 50 ng/ml CyPA or CyPB, respectively (FIG. 13A). Furthermore, migration of MM1S-luc cells was significantly decreased when either BMEC-60 (FIGS. 5B and 13B) or BMEC-1 cells (FIGS. 13B, C, D) were transduced with CyPA-shRNAs. As would be expected from an on-target effect of eCyPA-shRNAs, addition of recombinant eCyPA restored migration of MM cells incubated with BMEC-1 transduced with CyPA-sh-RNAs (FIG. 13D). Immunoblot analysis of total protein extracts from MM cells incubated with eCyPA revealed activation of several signaling pathways as compared with MM cells incubated without eCyPA. Among these were the Wnt/β-catenin, STAT3, AKT, and ERK pathways (FIG. 5C), all of which are known to promote survival, proliferation, and migration of MM cells. We also observed that the higher-glycosylated form of CD147 (i.e., the active form that induces matrix metalloprotease production and metastasis) was increased in CyPA-treated MM cells (FIG. 5C, arrows). Expression of matrix metalloprotease 9 (MMP-9) itself was increased in cells treated with eCyPA (FIG. 5C). CD147 was expressed at very low levels in MM cells incubated in the absence of eCyPA, whereas incubation with eCyPA dramatically increased its expression in a concentration-dependent (FIG. 5D, top) and time-dependent (FIG. 5D, bottom) manner. The signaling changes induced by eCyPA were reversed when MM cells were incubated in the presence of BMEC-60 cells with knockdown expression of CyPA (FIG. 5E). Proliferation of H929 and MM1S cells was also enhanced by eCyPA in a concentration-dependent manner (FIG. 5F).

Figure 5G:
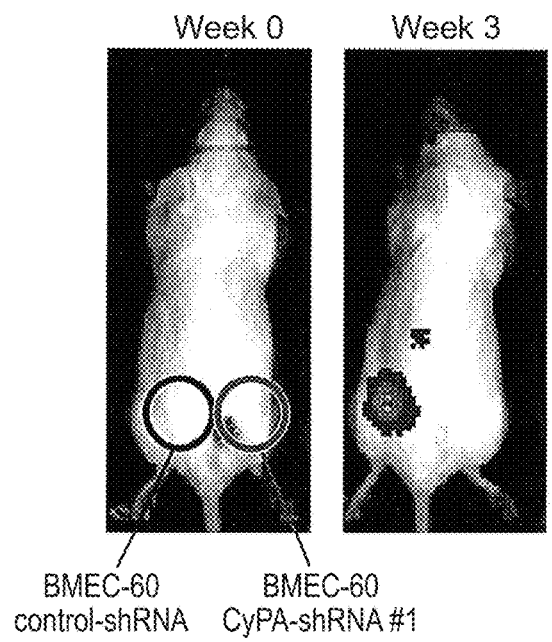
FIG. 5. eCyPA promotes signaling changes, migration, and proliferation of MM cells. Transwell migration assays of MM1S-luc cells incubated under different conditions.
Figure 5H:
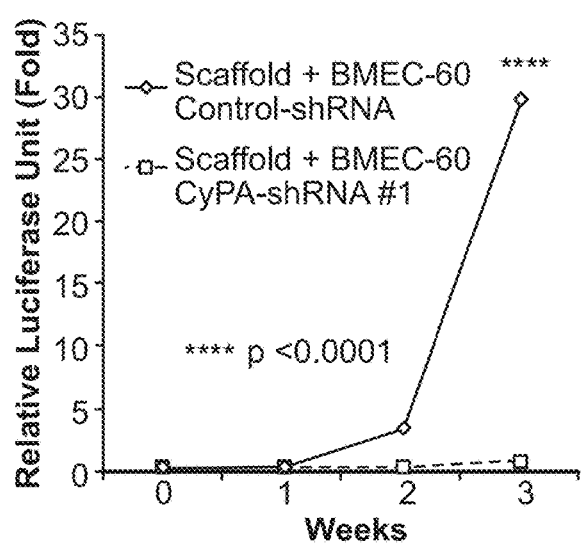
Figure 5I:
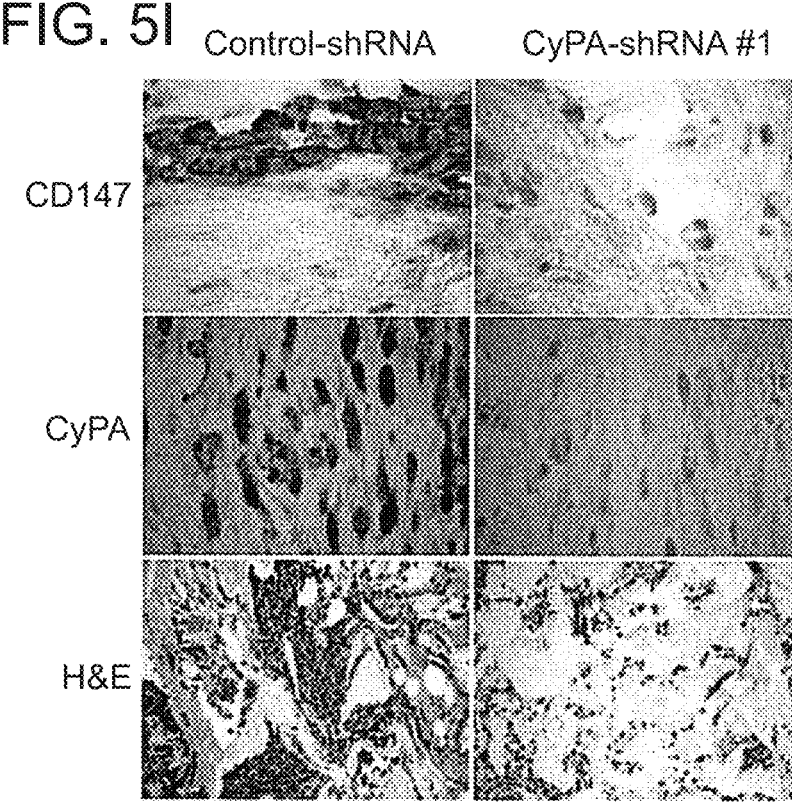
Figure 13F:
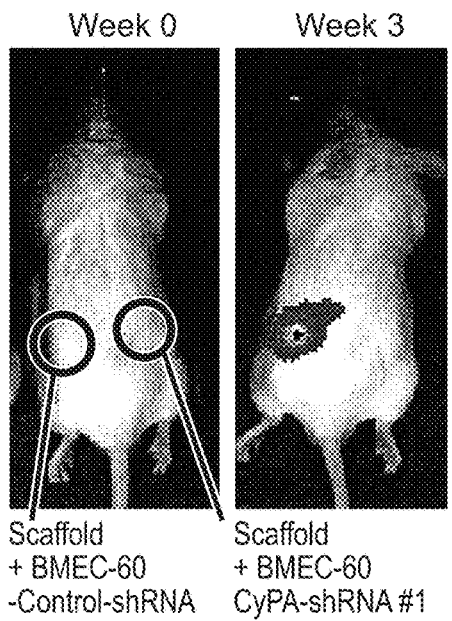
FIG. 13.
Figure 13H:
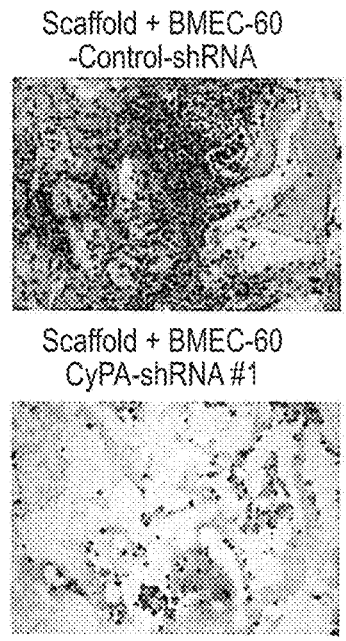
Figure 13G:
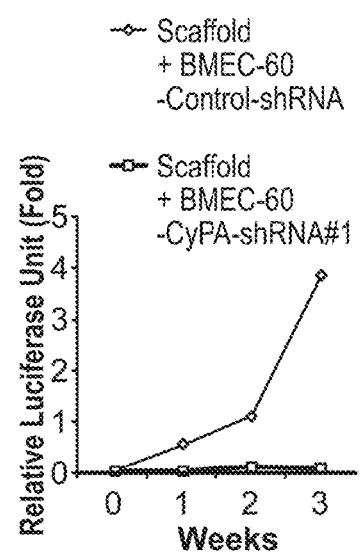

We next examined the role of eCyPA in vivo using the scaffold xenograft mouse model (FIG. 3D). These studies revealed that in vivo migration and growth of MM1S-luc cells within the scaffolds was inhibited when the scaffolds were coated with BMEC-60 cells lentivirally transduced with CyPA-shRNA as compared with control cells lentivirally transduced with control-shRNAs (FIGS. 5G-I). Immunohistochemical (FIG. 5I, top) and histological (FIG. 5I, bottom) analysis at the end of the experiment confirmed uniform scaffold coating with both BMEC-60-control-shRNA and BMEC-60-CyPA-shRNA cells. The results were replicated in two other independent experiments (FIG. 13E top and bottom), and reproduced with H929-luc cells and scaffolds coated with BMEC-60 cells (FIGS. 13F-H).

Example 8 CvPA Promotes Migration and Growth of MM Through the CD147 Receptor

Because recent studies have established CD147 as the principal signaling receptor mediating extracellular chemotaxis by eCyPA, we evaluated CD147 expression in MM cells using flow cytometric, immunohistochemical, and gene expression profiling analysis (Affimetrix). These studies showed that most myeloma cell lines, including MM1S-luc (FIG. 14A) and primary tumors (FIG. 14B), expressed significant amounts of CD147. At the mRNA level, CD147 expression was present in most MM samples, with significantly higher levels detected in MM samples than in normal plasma cells (FIG. 14C), indicating that CD147 expression increases with disease progression.

Figure 6A:
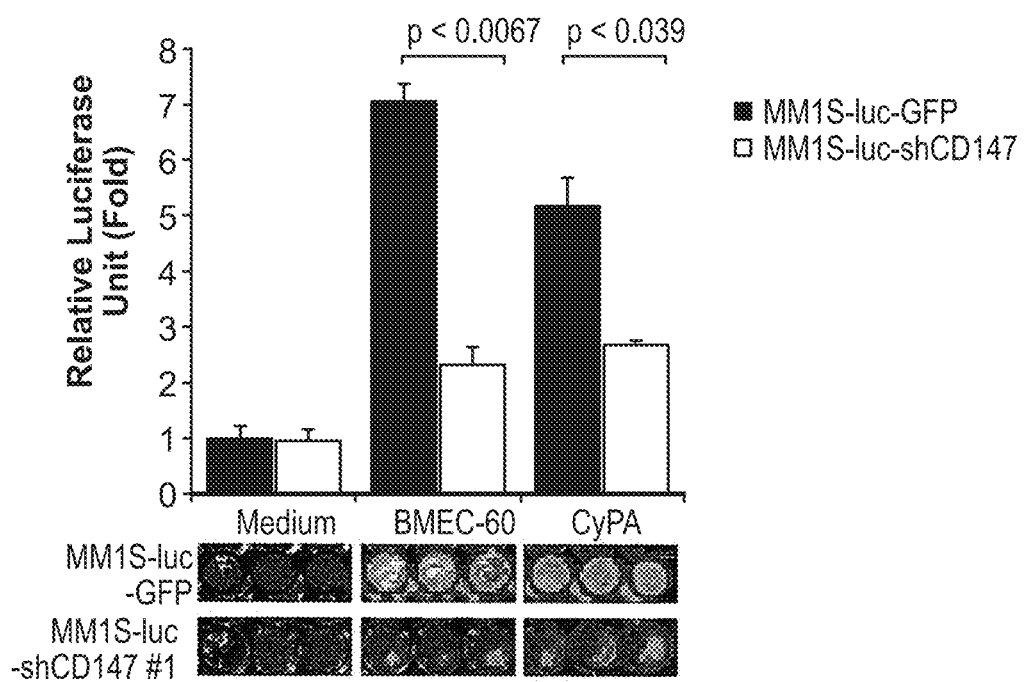
(FIG. 6A) Transwell migration assays of MM1 S-luc cells lentivirally transduced with control-shRNAs or shRNAs against CD147 (CD147-shRNA) and incubated with medium alone or BMEC-60 cells or recombinant eCyPA recombinant proteins.
Figure 6B:
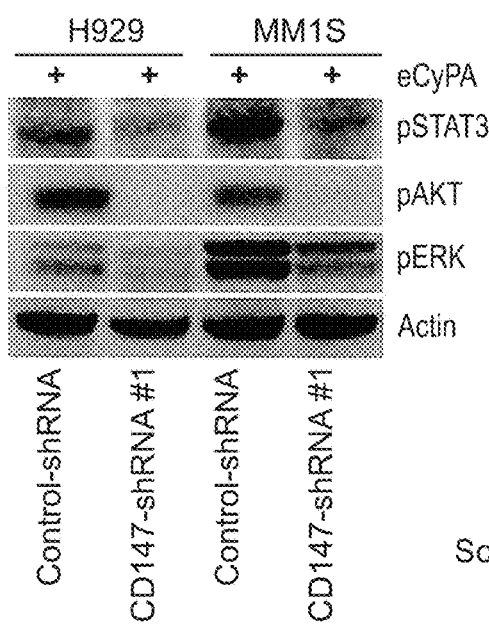
(FIG. 6B) Immunoblot of total protein extracts from H929 and MM1S cells lentivirally transduced with Control shRNA or CD147-shRNA in the presence of 50 ng/ml of recombinant eCyPA. Xenogen data (FIG. 6C), time course (FIG. 6D), and histologic analysis (FIG. 6E) of cell growth of MM1 S-luc transduced with Control-shRNA or CD147-shRNA within empty scaffolds or scaffolds coated with BMEC-60 cells.
Figure 6C:
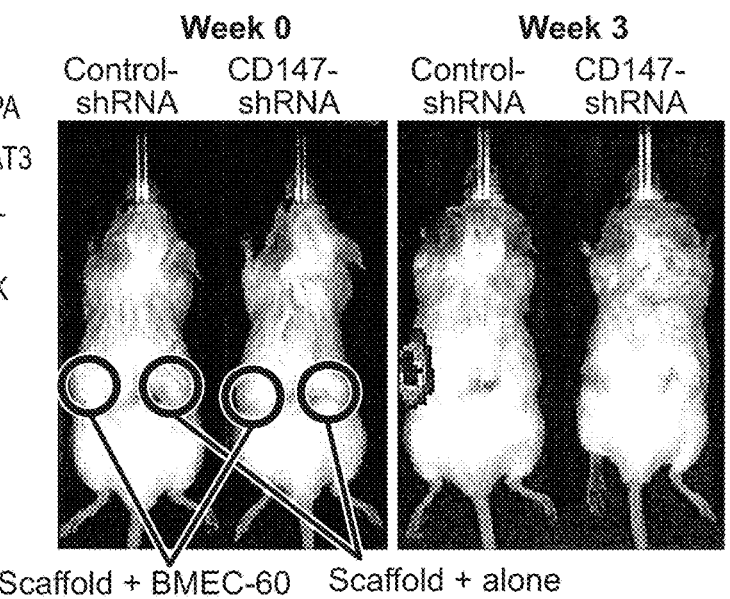
FIG. 6. CyPA promotes migration and growth of MM through the CD147 receptor.
(FIG. 6F) Transwell migration assays of MM1S-luc cells incubated with medium containing none or 50 ng/ml of eCyPA and increasing concentrations of CD147 Ab.
(FIG. 6G) Transwell migration of MM1S-luc cells incubated in the presence of medium alone, or PMMEC #1 or PBMSC #1 with CD147 Ab (100 ug/ml) or CXCR4 Ab (100 ug/ml). Migration data was normalized to medium alone. Results are means.+−.SD for assays performed in triplicate. Statistical significance of differences between groups was determined by unpaired Student's t-test.
Figure 6D:
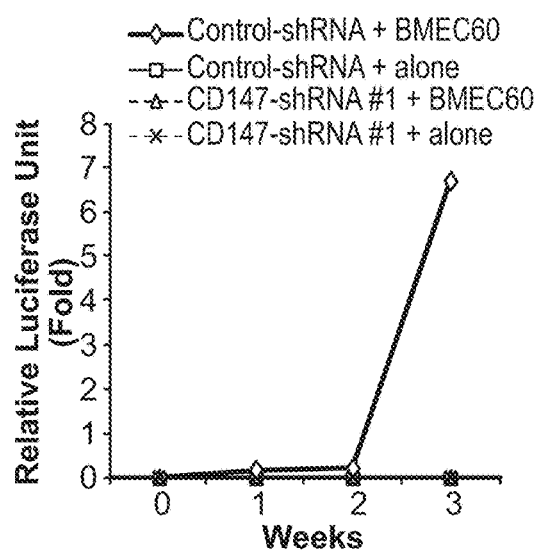
Figure 6E:
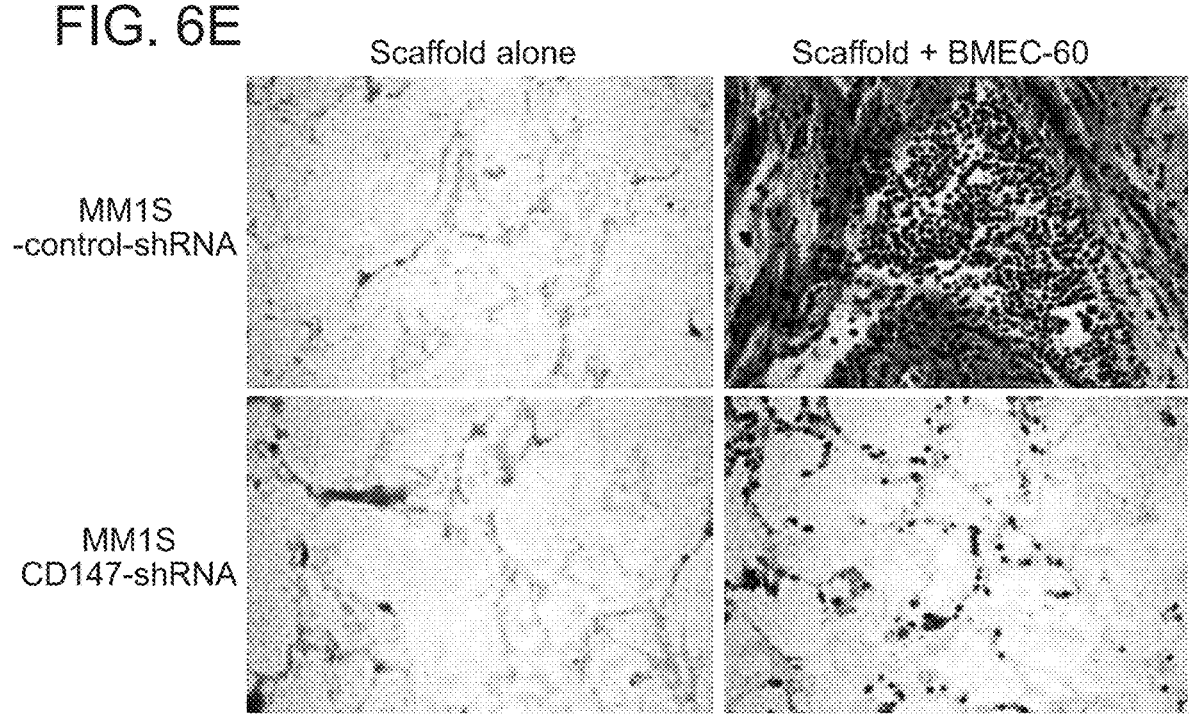

We then evaluated whether CD147 inactivation on MM cells could block the action of eCyPA. Knockdown of CD174 expression in MM1S and H929 cells with CD147-shRNAs (FIG. 14D) reduced migration in transwell assays in the presence of either BMEC-60 cells or CyPA (FIGS. 6A and 14E). The signaling changes induced by CyPA in H929 and MM1S cells (FIG. 5C) were reversed when the cells were first transduced with CD147-shRNAs (FIG. 6B). We also examined the role of CD147 in vivo using the scaffold xenograft mouse model (FIG. 3D). As shown in FIGS. 6C-E, knockdown CD147 expression in MM1S-luc cells inhibited migration and growth within scaffolds coated with BMEC-60 cells.

Example 9 Targeting the eCvPA/CD147 Complex for Multiple Myeloma Therapy

Figure 6F:
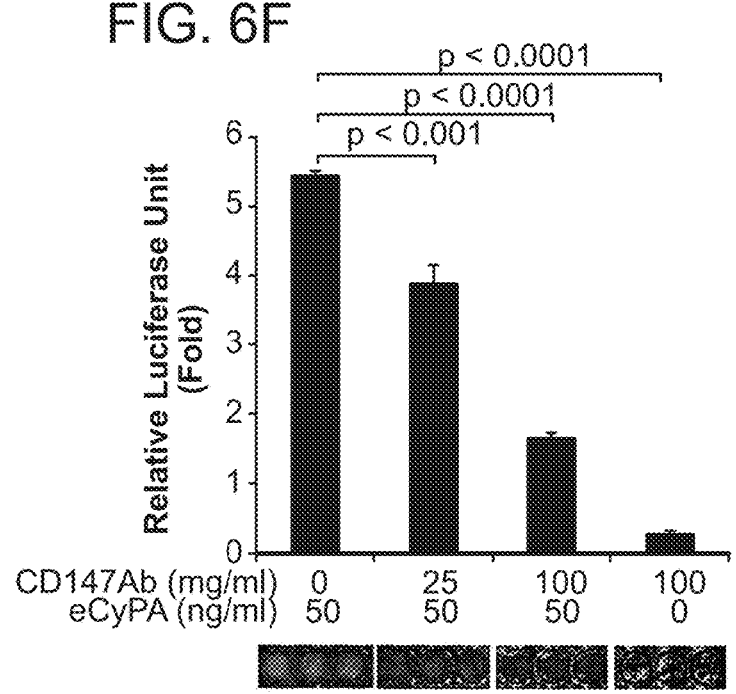
Figure 6G:
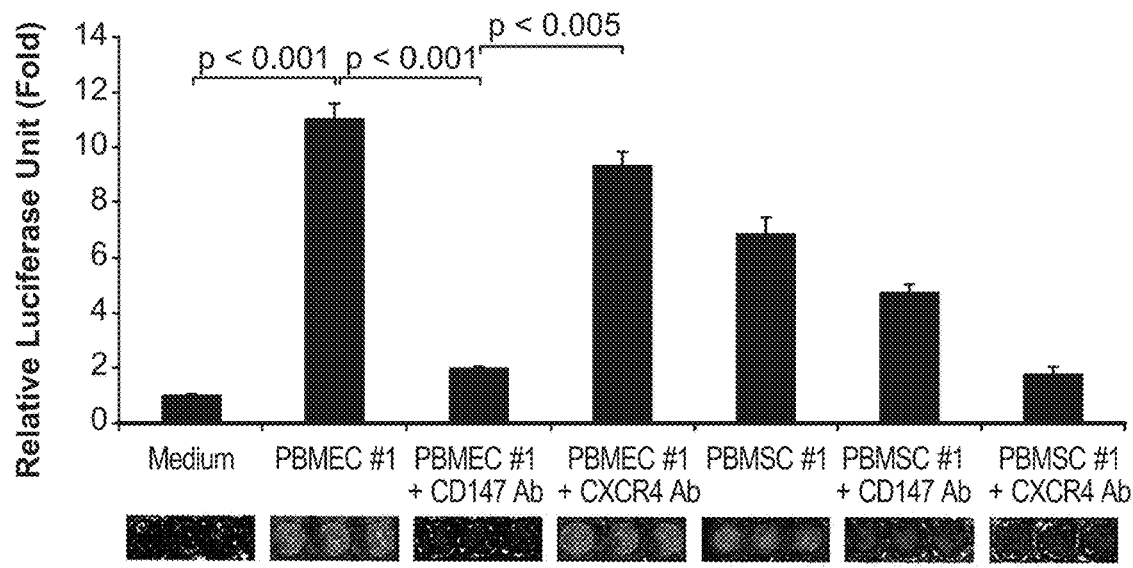

To test the targeting of the eCyPA/CD147 complex as a potential strategy for clinical MM therapy, we first evaluated whether an anti-CD147 Ab known to inhibit neutrophil migration in a mouse model of inflammation 35 also inhibits MM cell migration. Transwell assays revealed that eCyPA-induced MM1S-luc cell migration was markedly reduced if the cells were pre-treated with the CD147 Ab (FIG. 6F). Decreased migration was associated with inhibition of CyPA-induced activation of pERK, pSTAT3, pAKT, and PARP (FIG. 14F). PARP activation by CD147 Ab was concentration-dependent (FIG. 14G). Interestingly, CXCR4 Ab migration of MM cells induced by SDF-113 did not inhibit CyPA-induced migration of MM1S-luc cells (FIG. 14H). Migration of MM1S-luc cells was also markedly inhibited by the CD147 Ab when cells were incubated in the presence of primary BMECs, but not primary BMSCs, isolated from same MM patient (FIG. 6G). In addition, treatment with a CXCR4 Ab did not inhibit migration of MM1S-luc cells induced by primary BMECs, but markedly inhibited migration induced by primary BMSCs (FIG. 6G). These results prompted us to evaluate secretion of eCyPA and SDF-1 in primary BMECs and primary BMSCs by ELISA. As shown in FIG. 14I, eCyPA was detected in CM from primary BMECs, but not primary BMSCs, and an inverse correlation was observed with SDF-1. These results suggested that primary BMECs and primary BMSCs play different roles in MM migration, most likely because they secrete different chemo-attractant factors.

Figure 7A:
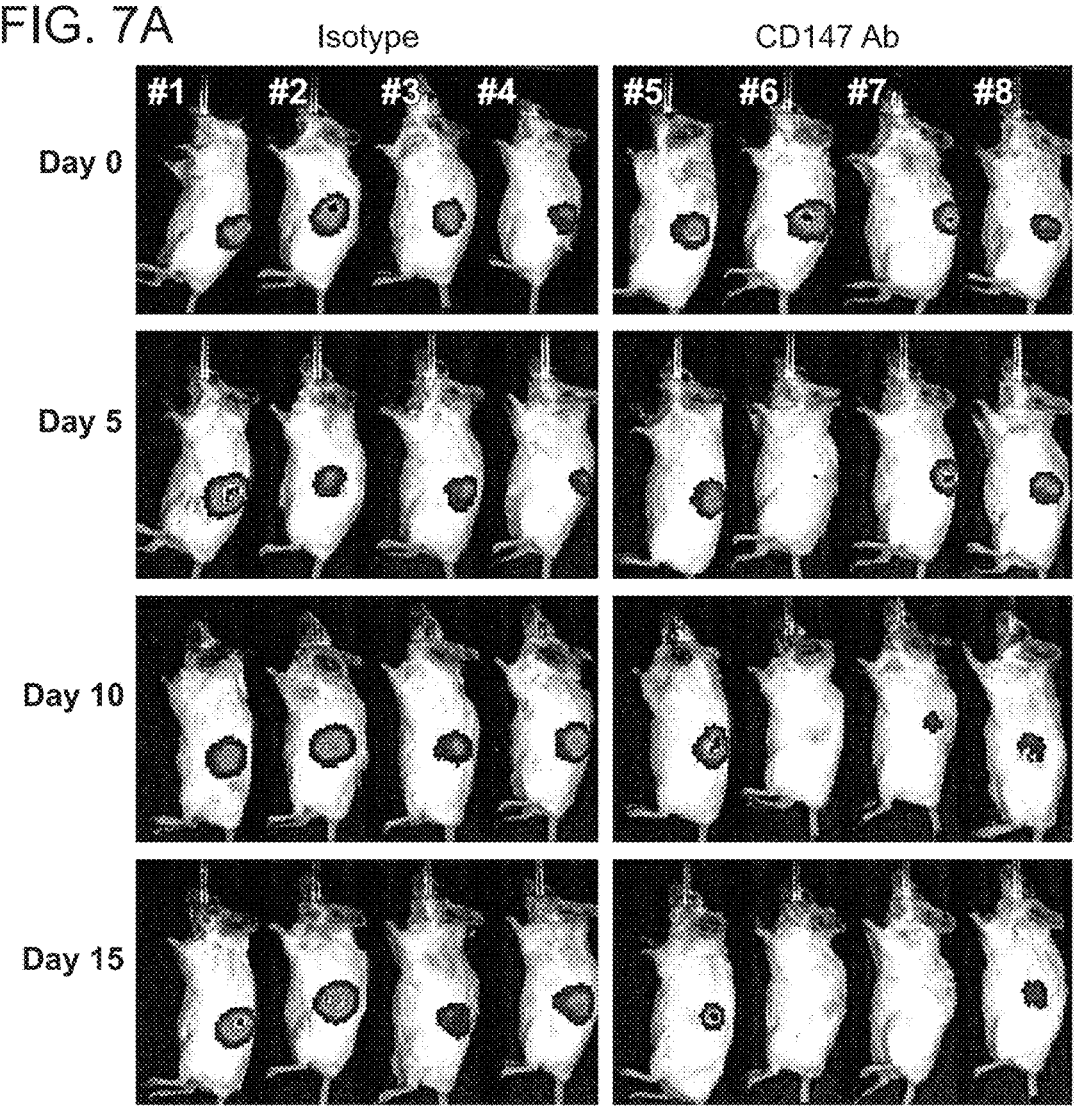
FIG. 7. Targeting eCyPA/CD147 complex is associated with anti-MM activity. Decreased CD147 expression in circulating MM cells. Xenogen data (FIG. 7A) and histologic analysis (FIG. 7B) of MM1S-luc cell growth within scaffolds coated with BMEC-60 cells and implanted subcutaneously in CB 17.Cg-PrkdcscidLystbg-J/Crl mice. Groups of 4 mice were subsequently treated with either isotype Ab or anti-CD147 Ab, and tumor growth within the scaffolds was evaluated by Xenogen imaging every five days.
(FIG. 7C) Immunofluorescence analysis of CD147 expression in MM plasma cells from BM (top) and peripheral blood (PB) (bottom) from one MM patient (Case #1).
(FIG. 7D) Immunofluorescence analysis of CD147 expression in normal plasma cells from BM (top) and lymph node (LN) (bottom) in two different normal donors (Case #3 and #4).
Figure 7B:
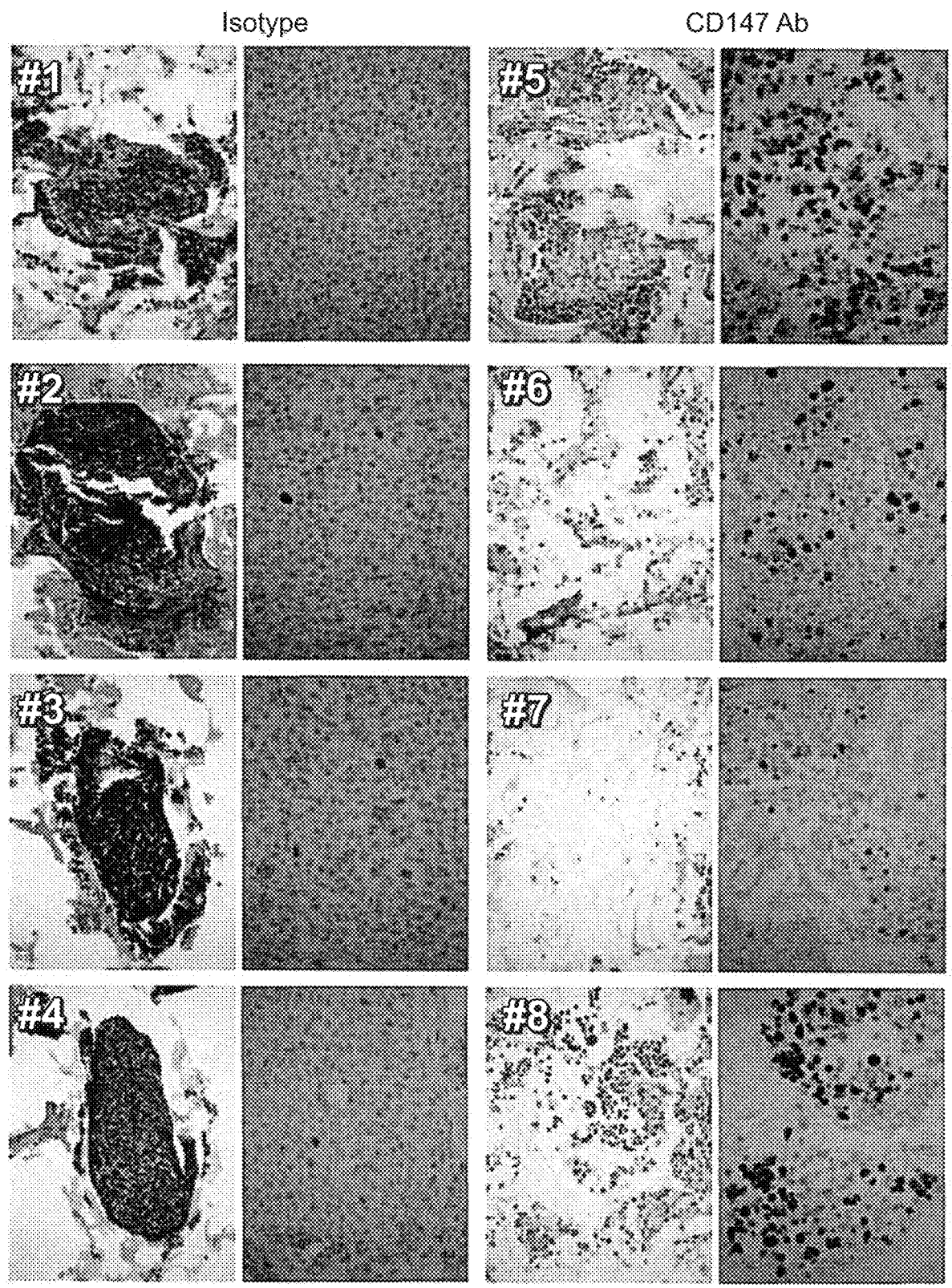
Figure 15A:
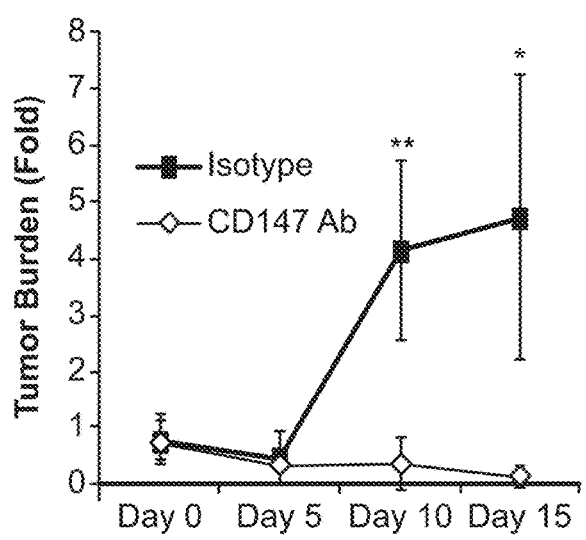
(FIG. 15A) Time course of Xenogen imaging of MM1S-luc cell growth in scaffolds implanted in CB17.Cg-PrkdcscidLystbg-J/Crl mice and treated with local injections of isotype control or anti-CD147 Abs.
Figure 15B:
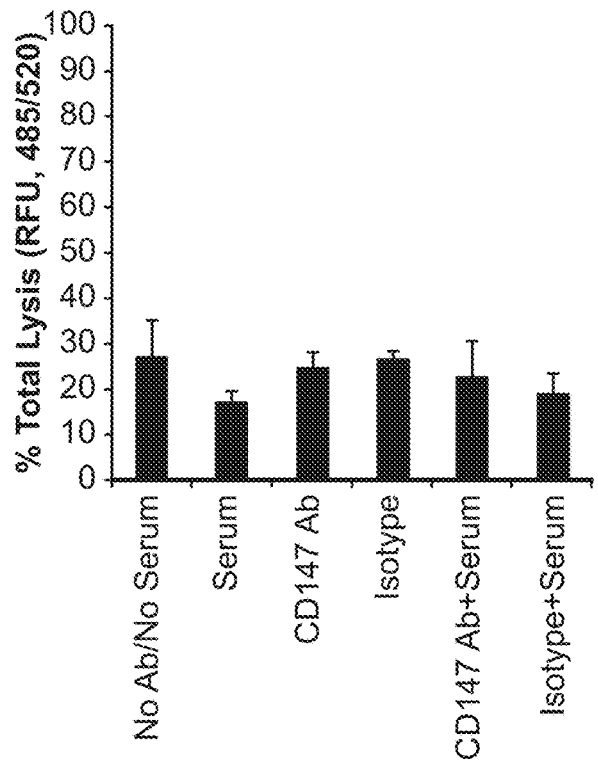
(FIG. 15B) Complement dependent cytotoxicity (CDC) was assessed using Calcein-AM-labeled MM1S-Luc cells, CD147 Ab, isotype control Ab, and mouse serum.
Figure 15C:
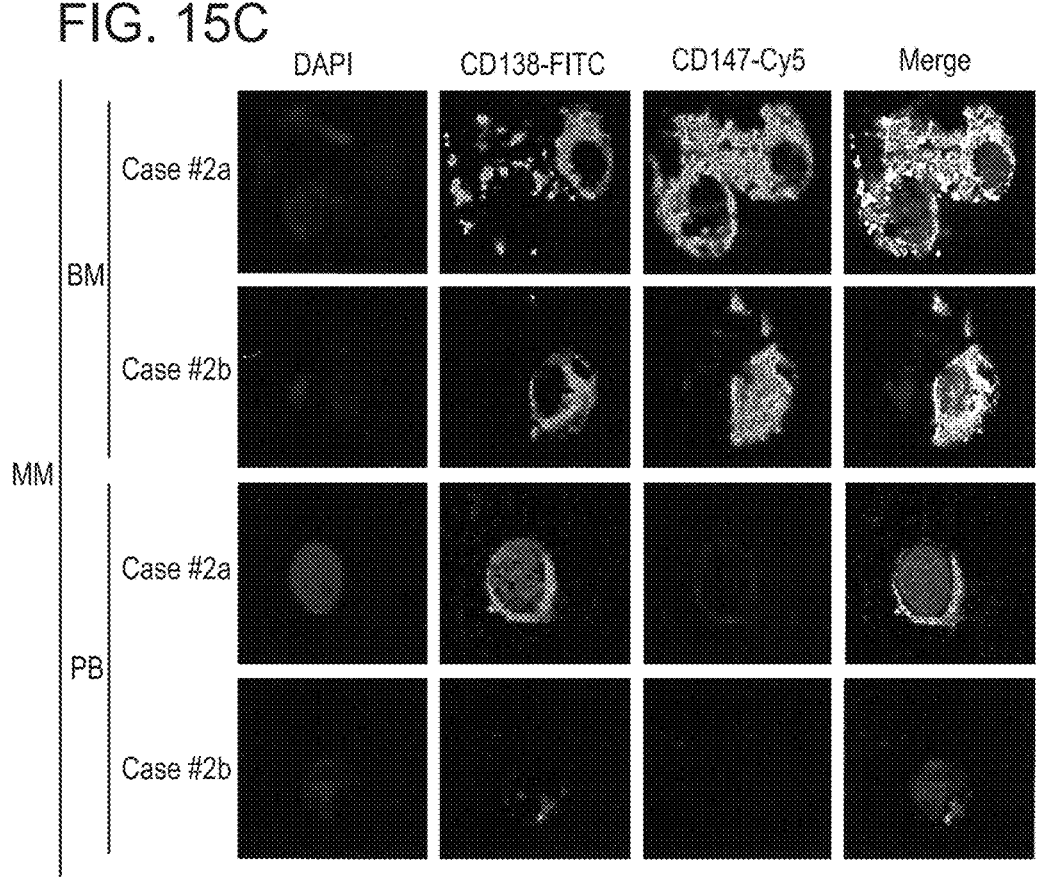
(FIG. 15C) Immunofluorescence analysis of CD147 expression in MM plasma cells from bone marrow (BM) (top) and peripheral blood (PB) (bottom) from a MM patient (Cases #2).
Figure 15D:
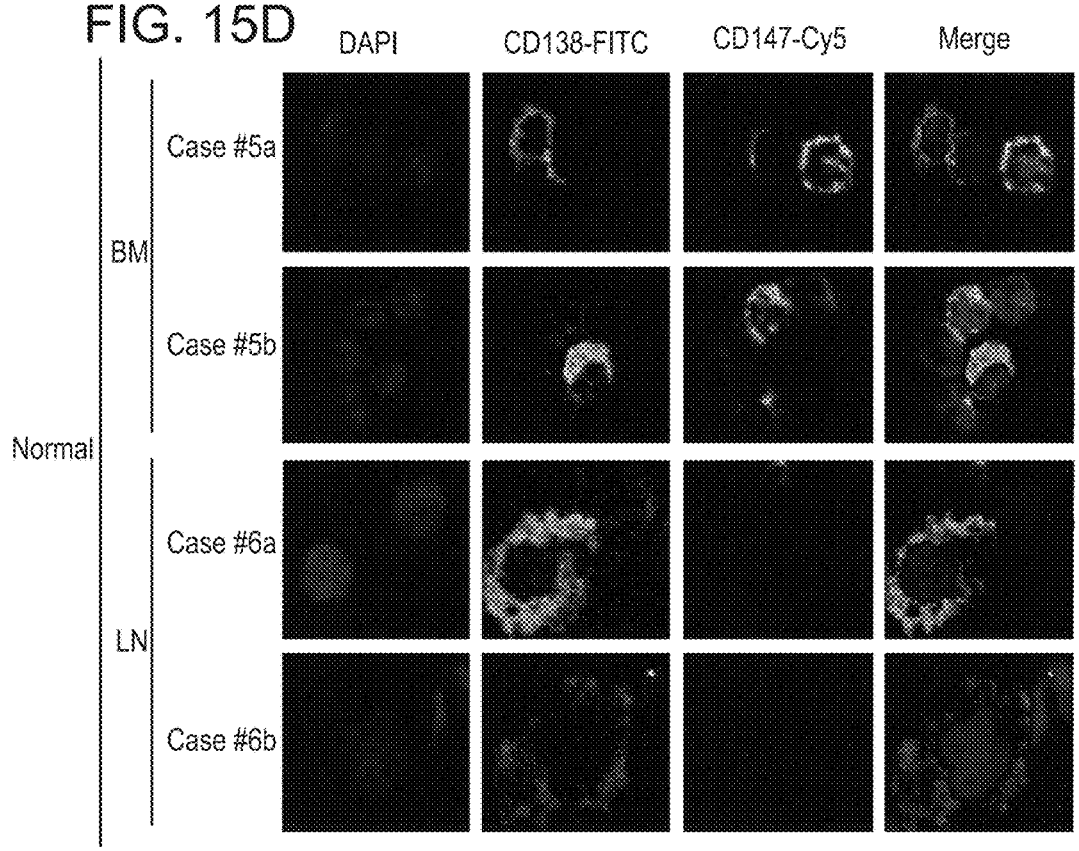
(FIG. 15D) Immunofluorescence analysis of CD147 expression in normal plasma cells from bone marrow (BM) (top) and lymph node (LN) (bottom) from two different normal donors (Cases #5 and #6). For each sample from BM, PB, and LN from MM patients or normal individuals, 10 different fields (a-j) with plasma cells were analyzed. Only two representative fields are shown (a, b).

Our observation of decreased pSTAT in MM cells either transduced with CD147-shRNA (FIG. 6B) or treated with CD147 Ab (FIG. 14F) prompted us to next use the scaffold system to evaluate whether CD147 Ab could be therapeutic for MM in vivo. To this end, scaffolds were pre-coated with BMEC-60 cells for two weeks, and then incubated with MM1S-luc cells for one week. When an evenly distributed coating of cells was obtained, the scaffolds were implanted into the flank of non-γ-irradiated immunodeficient mice. One week post-implantation the mice were subjected to whole-body imaging, and mice with comparable tumor burdens were selected for Ab therapy (FIG. 7A, Day 0). Mice were injected with 100 μl of a solution containing either 100 ng of isotype Ab (control group, n=4) or anti-CD147 Ab (treated group, n=4) s.c. every other day, in a region adjacent to the scaffolds, and tumor growth within the scaffold was evaluated by Xenogen imaging every five days. On day 15 of treatment the mice were euthanized, and the scaffolds were subjected to histologic and immunohistochemical analysis (FIG. 7B). Quantitative Xenogen imaging revealed that anti-CD147 Ab treatment had significantly decreased MM1S-luc growth within the scaffolds compared with isotype Ab-treated mice (FIG. 15A). In addition, more intense immunostaining for caspase was observed in MM1S-luc cells within scaffolds of mice treated with CD147 Ab (FIG. 7B) than in mice treated with isotype Ab. Analysis of immune-mediated activity revealed that complement-dependent cytotoxicity was not induced by the CD147 Ab (FIG. 15B). Taken together, these studies indicated that inhibition of the eCyPA/CD147 axis inhibits proliferation and induces apoptosis of MM cells, and thus could represent a novel targeted therapy in MM.

Example 10 Decreased CD147 Expression in Circulating MM Cells

Figure 7C:
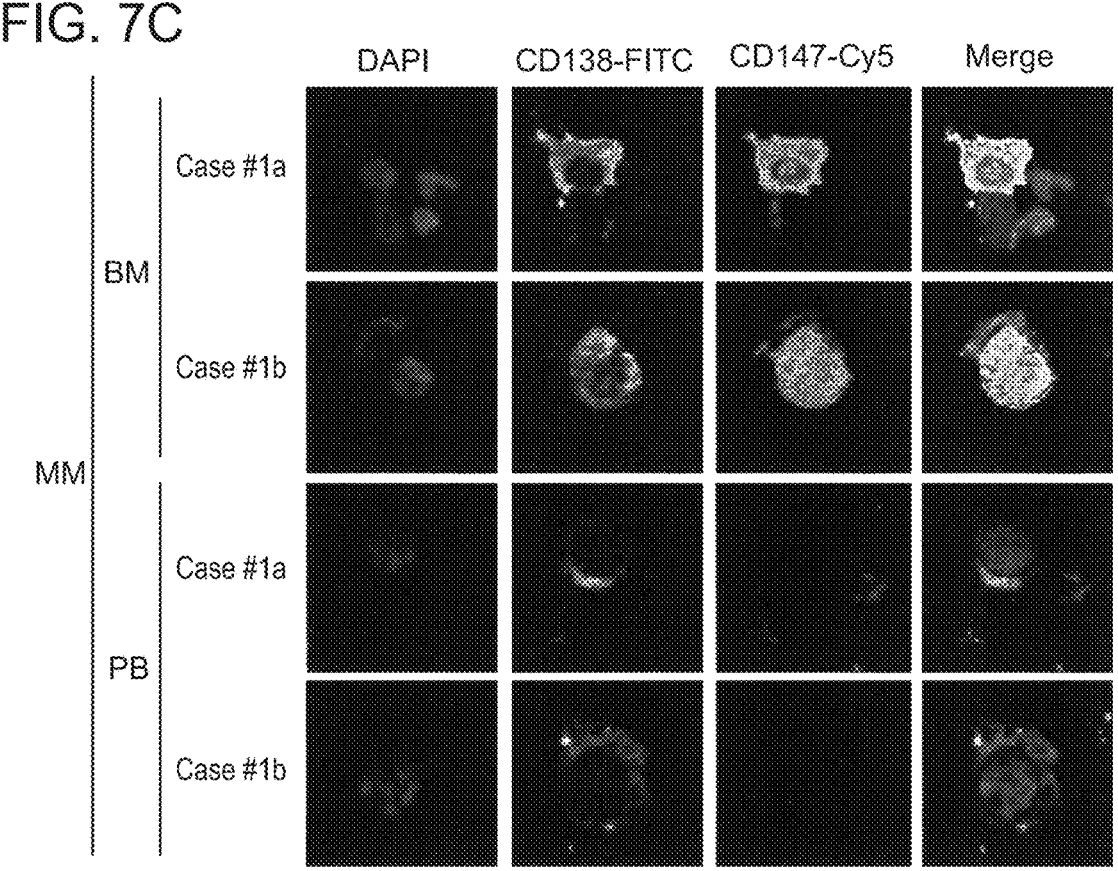
Figure 7D:
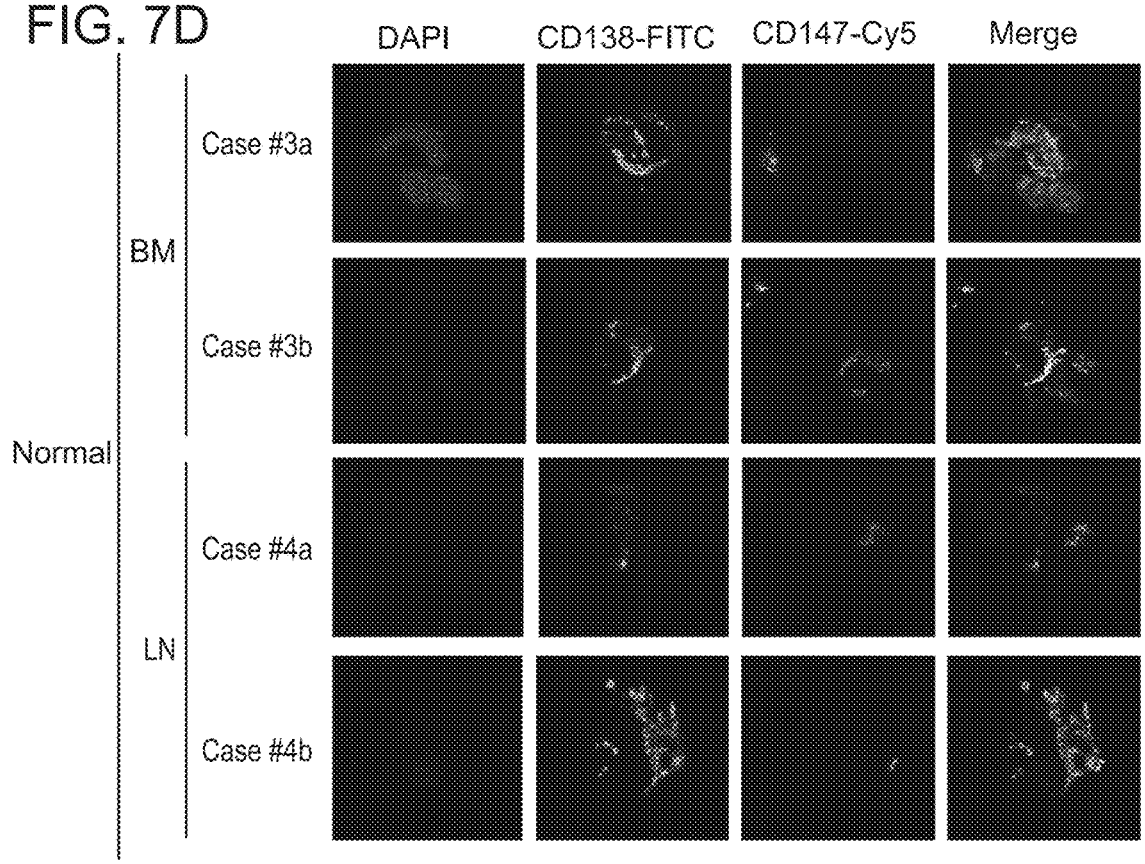

Since our previous results indicated that eCyPA secreted by BMECs is an important driver of BM homing by MM cells via binding of the CD147 receptor expressed on MM cells, we measured CD147 expression in plasma cells from the lymph nodes and BM of healthy subjects, as well as in cells in plasma cells from BM and PB of MM patients. Due to the paucity of plasma cells in BM and lymph nodes of normal individuals as well as their relatively small numbers in the PB of MM patients, immunoblotting studies were not feasible. In these instances, therefore, CD147 expression was determined by double-wavelength immunofluorescence analysis of cytospin preparations using CD138 as a plasma cell marker. These studies revealed that all BM plasma cells analyzed in 10/10 MM patients expressed high CD147 levels (FIGS. 7C, top and 15C, top) while 9/10 tested samples of PB plasma cells from the same MM patient did not (FIGS. 7C, bottom and 15C, bottom). In contrast, 9/10 normal plasma cells analyzed from BM (FIGS. 7D, top and 15D, top) and 8/10 cells analyzed from lymph nodes of every normal subject (FIGS. 7D, bottom and 15D, bottom) expressed CD147 at only low or undetectable levels.

Example 11 CLL and LPL Cells Express CD147 and Migrate in Response to eCyPA

Figure 16A:
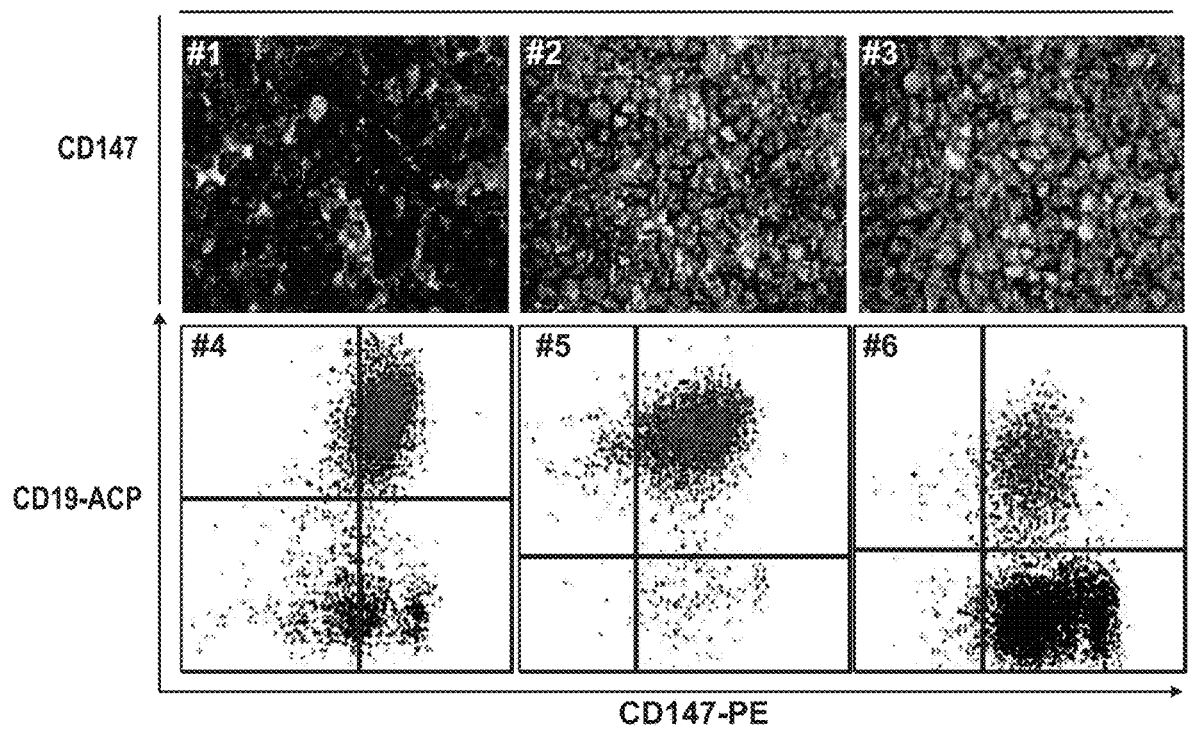
(FIG. 16A) Representative immunostains (top, n=10) and flow cytometric (bottom, n=6) analysis of CD147 expression in BM samples from CLL patients.
Figure 16B:
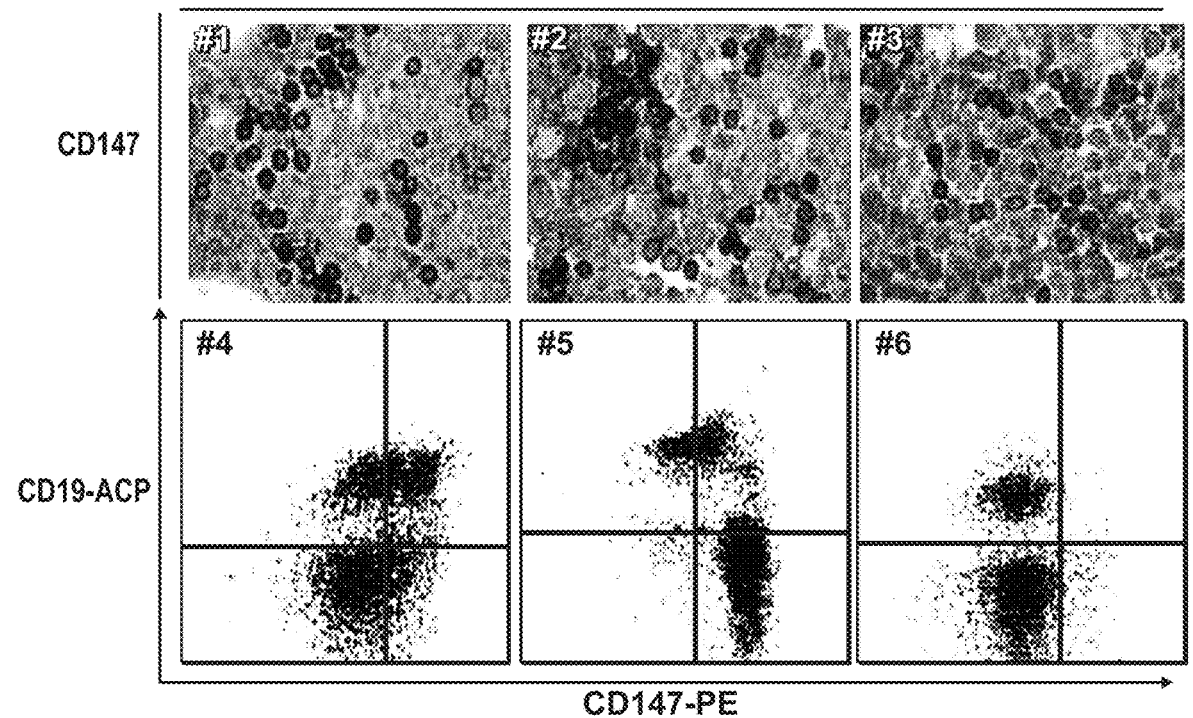
(FIG. 16B) Representative immunostains (top, n=10) and flow cytometric (bottom, n=6) analysis of CD147 expression in BM samples from LPL patients.
Figure 16E:
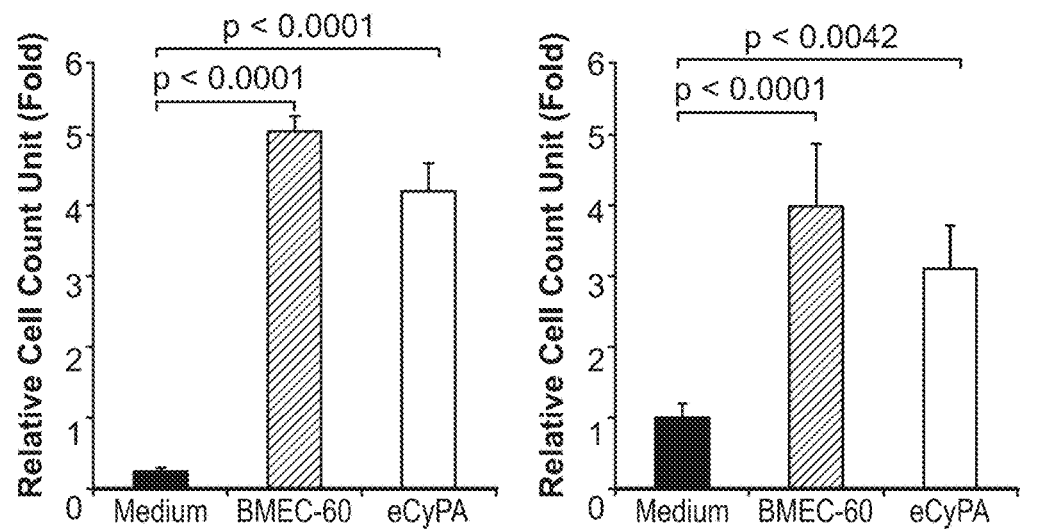
(FIG. 16E) Transwell migration assay of HG3 (left) and CLLPT #1 (right) cells incubated with medium alone, BMEC-60 cells, or 50 ng/ml of recombinant eCyPA.
Figure 16E:
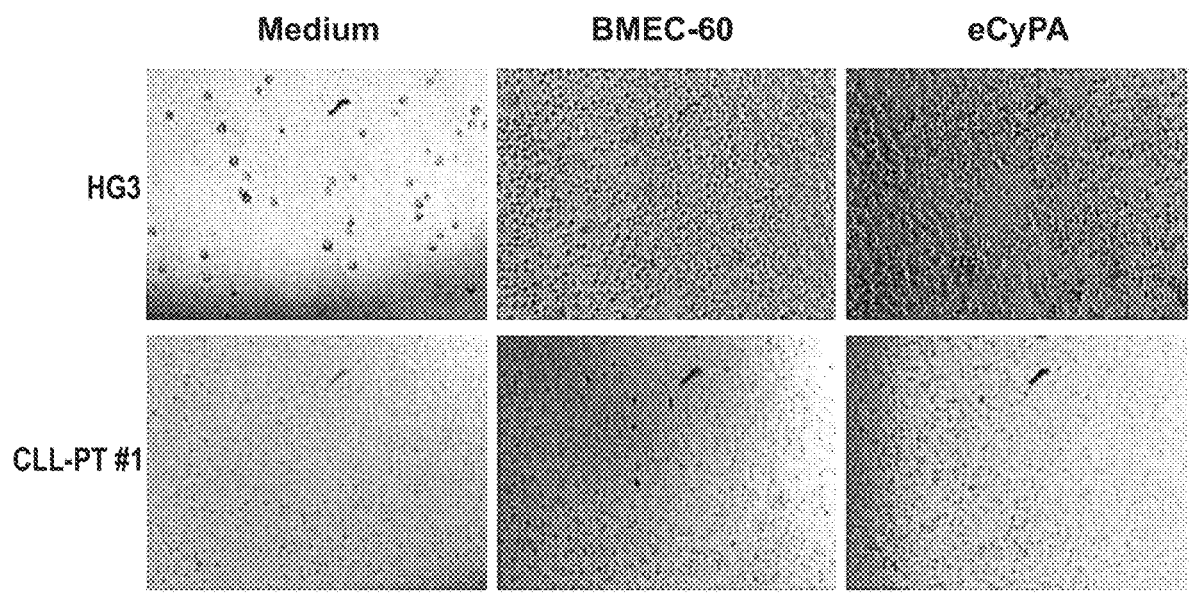
Figure 16F:
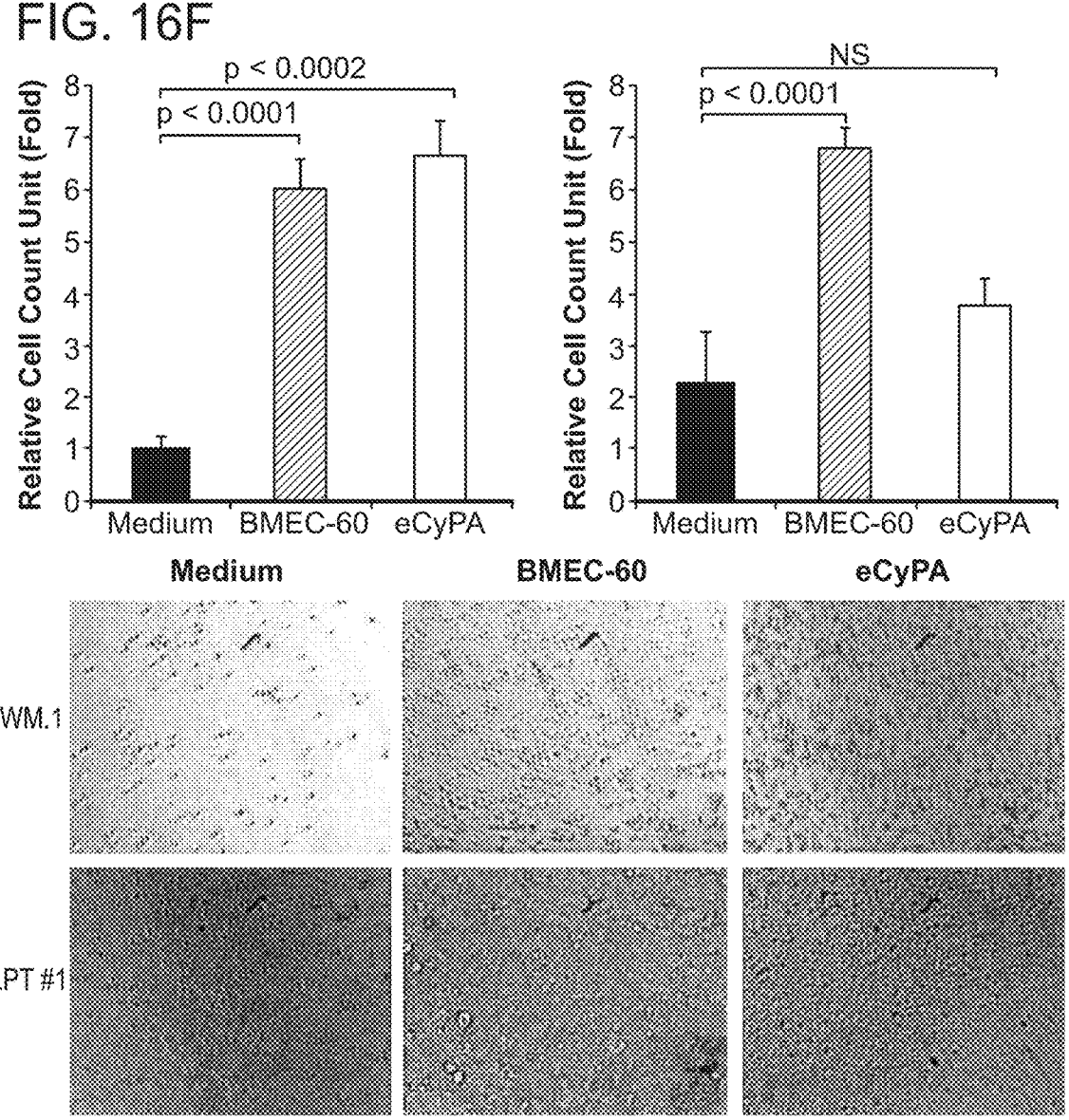
(FIG. 16F) Transwell migration of BCWM. 1 (left) and LPLPT #1 (right) cells incubated with medium alone, BMEC-60 cells, or 50 ng/ml of recombinant eCyPA. Migration of primary CLL and LPL tumor patient cells was evaluated in four different samples for each tumor type. One representative sample for each primary tumor type is shown. Unlabeled cell lines and primary tumors were used, and migration was evaluated by counting cells in the bottom chamber. Representative fields are shown at the bottom.

Since CLL and LPL are B-cell malignancies that, like MM, preferentially colonize the BM, it was of interest to also examine whether cell lines and primary tumor cells derived from patients express CD147, and whether eCyPA is chemotactic to these cells. Immunostains (FIGS. 16A, B, top), and flow cytometry (FIGS. 16A, B, bottom) revealed that most CLL and LPL primary cells expressed CD147. In addition, the CLL cell line HG3 and primary tumor CLLPT #1 (FIG. 16C) as well as the LPL cell line BCWM.1 and LPLPT #1 (FIG. 16D) used in subsequent in vitro migration studies expressed high levels of CD147. Furthermore, both BMEC-60-derived CM and eCyPA enhanced migration of CLL (FIG. 16E, bottom) and LPL (FIG. 16F, bottom) cells in transwell assays.

Figure 8:
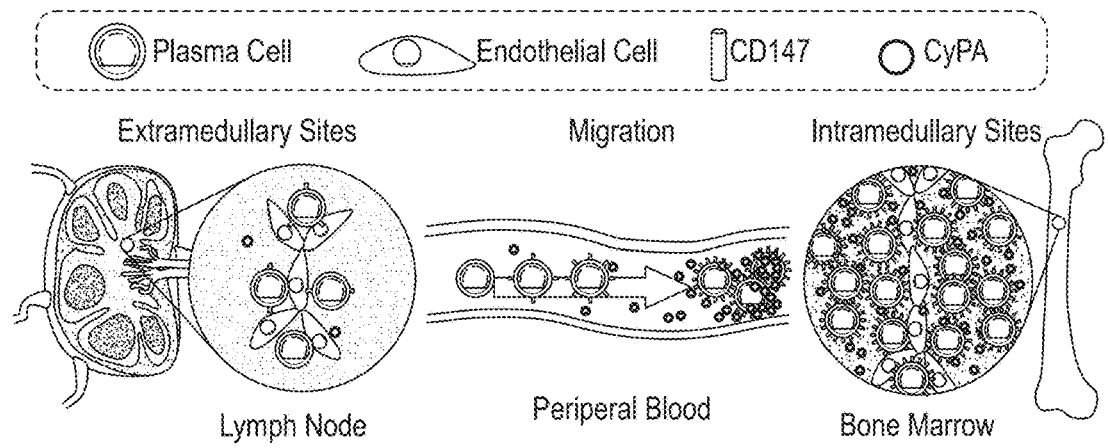
FIG. 8. Proposed model of BM homing of MM cells based on eCyPA secreted by BMECs and on CD147 expression by MM cells.

On the basis of the present findings and the generally recognized trafficking model of normal lymphocytes and BM recruitment of hematopoietic stem cells (HSCs), we propose a mechanism that could explain both the preferential BM colonization of MM cells during early stages of disease and loss of preferential homing during the late stages of disease progression (e.g., plasma cell leukemia) (FIG. 8). In this model, normal plasma cells do not accumulate in the BM because they don't express CD147 39 (FIG. 7D), whereas MM cells can accumulate in BM because they do express CD147 39 (FIG. 7C), the known receptor for eCyPA 33 which serves as a chemoattractant promoting migration of MM cells along a concentration gradient between the PB and BM (FIG. 4I). This gradient is generated because endothelial cells from the BM, but not those from other organ sites, produce and secrete eCyPA in significant amounts. In the BM, the effect of eCyPA from endothelial cells can be enhanced by local production and secretion by myeloid cells (FIG. 11B). Although MM cells also express CyPA (FIG. 4H), they secrete it at very low rates relative to BMECs (FIG. 11D), indicating that MM are less efficient than BMECs in terms of Rho-kinase-mediated CyPA secretion, and that MM-derived eCyPA does not play a significant role in MM recruitment to the BM, at least during initial stages of disease, when tumor burden is low. As MM cells circulate in the PB and encounter progressively higher concentrations of eCyPA, binding of eCyPA to CD147 further increases CD147 expression by MM cells (FIG. 5D), thereby enhancing their migration. Additionally, extravasation of MM cells, required for penetration through the sub-endothelial basement membrane, is mediated by the production of proteolytic enzymes such as MMP-9, whose level is known to rise when eCyPA binds to CD147 (FIG. 5C). Once MM cells are within the BM niche, colonization and growth is further enhanced by direct exocrine action of eCyPA and by local production and secretion of other growth factors and chemoattractants (e.g. laminin-1, MIP-1α, SDF-1, MCP-1, VEGF, IGF-1). Therefore, selective colonization of MM cells induced by eCyPA is the consequence of selective BM homing (i.e., selective migration of MM cells through the blood to the BM niche), followed by selective survival and growth within the BM niche. It is also possible that eCyPA in the BM serves as a "retention signal" for MM cells, which needs to be further investigated. During MM progression, the number of circulating MM cells may increase because of genetic and epigenetic changes in the tumor that decrease CD147 expression (FIG. 7C). As a consequence MM cells, now unable to respond to eCyPA, can leave the BM to colonize extramedullary sites.

The role we have uncovered for the eCyPA/CD147 complex in MM identifies this interaction as an attractive target for therapeutic intervention. Agents potentially disruptive of this interaction can be grouped into those that can directly target CD147, eCyAP, or their mutual interaction, or those which act indirectly via inhibition of the Wnt/β-catenin/BCL9 transcriptional complex. Indeed, using CD147 Ab as a tool to block eCyPA- and BMECs-induced migration of MM cells (FIG. 6G), we provide here the first evidence that inhibition of the eCyPA/CD147 complex is associated with increased caspase 3 activity (FIG. 7B) and anti-MM activity (FIG. 15A). Such agents may also be useful for the treatment of other B-cell malignancies, such as CLL and LPL, which similarly express CD147 and respond to eCyPA (FIG. 16). Interestingly, CD147 inhibition using an anti-CD147 monoclonal antibody has been reported to afford significant symptom relief in murine models of acute lung inflammation, asthma and rheumatoid arthritis, and hepatocellular carcinoma.

In summary, our studies have uncovered a pivotal role of the eCyPA/CD147 axis in the functional interaction between MM cells and BMECs that contributes to BM homing as well as initiation and/or progression of MM, and have established an important functional link between the oncogenic Wnt/β-catenin/BCL9 pathway and the eCyPA/CD147 system which implicates chronic inflammation in the pathogenesis of MM. Translational applications of our studies to the clinical setting include: (1) identifying biomarkers of disease progression within the eCyPA/CD147 cascade, and (2) developing novel therapies which target eCyPA/CD147 interactions in MM and other B-cell malignancies that preferentially colonize and grow within the BM niche.

It is to be understood that the foregoing description is intended to illustrate and not to limit the scope of the invention, which is defined by the scope of the appended claims. Other embodiments are within the scope of the following claims.

The invention claimed is:

1. A method of treating multiple myeloma in a patient, the method comprising:
administering to the patient an effective dose of a therapeutic agent comprising an inhibitory nucleic acid that targets cyclophilin A (CyPA) or CD147 selected from the group consisting of a triplex forming oligonucleotide, an aptamer, a ribozyme, an antisense RNA, a short interfering RNA (siRNA), a micro-RNA (miRNA), and a small hairpin RNA (shRNA),
wherein the patient has an extracellular CyPA test value greater than a reference extracellular CyPA value obtained from a subject known not to have multiple myeloma.

2. The method of claim 1, wherein the therapeutic agent inhibits CyPA-induced activation of pERK, pSTAT3, pAKT, and/or PARP.

3. The method of claim 1, wherein the therapeutic agent inhibits the Wnt/β-catenin/BCL9 transcriptional complex.

4. The method of claim 1, wherein the therapeutic agent increases caspase 3 activity.

5. A method of inhibiting the migration of multiple myeloma cells in a patient into the bone marrow of the patient, the method comprising:
administering an effective amount of the therapeutic agent to the patient an effective dose of a therapeutic agent comprising an inhibitory nucleic acid that targets cyclophilin A (CyPA) or CD147 selected from the group consisting of a triplex forming oligonucleotide, an aptamer, a ribozyme, an antisense RNA, a short interfering RNA (siRNA), a micro-RNA (miRNA), and a small hairpin RNA (shRNA), and
wherein extracellular CYPA value in the patient is greater than a reference extracellular CYPA value obtained from a subject known not to have multiple myeloma.

6. The method of claim 5, wherein the therapeutic agent inhibits CyPA-induced activation of pERK, pSTAT3, pAKT, and/or PARP.

7. The method of claim 5, wherein the therapeutic agent inhibits the Wnt/β-catenin/BCL9 transcriptional complex.

8. The method of claim 5, wherein the therapeutic agent increases caspase 3 activity.

9. The method of claim 1, wherein the therapeutic agent comprising an inhibitory nucleic acid targets CyPA.

10. The method of claim 9, wherein the therapeutic agent comprises shRNA.

11. The method of claim 1, wherein the therapeutic agent comprising an inhibitory nucleic acid targets CD147.

12. The method of claim 11, wherein the therapeutic agent comprises shRNA.

13. The method of claim 5, wherein the therapeutic agent comprising an inhibitory nucleic acid targets CyPA.

14. The method of claim 13, wherein the therapeutic agent comprises shRNA.

15. The method of claim 5, wherein the therapeutic agent comprising an inhibitory nucleic acid targets CD147.

16. The method of claim 15, wherein the therapeutic agent comprises shRNA.

* * * * *

SEQUENCE LISTING

<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Gly Gly Ser Met Val Asn Pro Thr Val Phe Phe Asp Ile Ala Val Asp
1               5                   10                  15

Gly Glu Pro Leu Gly Arg Val Ser Phe Glu Leu Phe Ala Asp Lys Val
            20                  25                  30

Pro Lys Thr Ala Glu Asn Phe Arg Ala Leu Ser Thr Gly Glu Lys Gly
        35                  40                  45

Phe Gly Tyr Lys Gly Ser Cys Phe His Arg Ile Ile Pro Gly Phe Met
    50                  55                  60

Cys Gln Gly Gly Asp Phe Thr Arg His Asn Gly Thr Gly Gly Lys Ser
65                  70                  75                  80

Ile Tyr Gly Glu Lys Phe Glu Asp Glu Asn Ile Leu Lys His Thr Gly
                85                  90                  95

Pro Gly Ile Leu Ser Met Ala Asn Ala Gly Pro Asn Thr Asn Gly Ser
            100                 105                 110

Gln Phe Phe Ile Cys Thr Ala Lys Thr Glu Trp Leu Asp Gly Lys Val
        115                 120                 125

Val Phe Gly Lys Val Lys Glu Gly Met Asn Ile Val Glu Ala Met Glu
    130                 135                 140

Arg Phe Gly Ser Arg Asn Gly Lys Thr Ser Lys Lys Ile Thr Ile Ala
145                 150                 155                 160

Asp Cys Gly Gln Leu Glu
                165

<210> SEQ ID NO 2
<211> LENGTH: 385
<212> TYPE: PRT
<213> ORGANISM: Homo sapiens

<400> SEQUENCE: 2

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140

```
Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
            165                 170                 175

Val Leu Lys Glu Asp Ala Leu Pro Gly Gln Lys Thr Glu Phe Lys Val
        180                 185                 190

Asp Ser Asp Gln Trp Gly Glu Tyr Ser Cys Val Phe Leu Pro Glu
        195                 200                 205

Pro Met Gly Thr Ala Asn Ile Gln Leu His Gly Pro Arg Val Lys
210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
            245                 250                 255

Lys Ile Thr Asp Ser Glu Asp Lys Ala Leu Met Asn Gly Ser Glu Ser
            260                 265                 270

Arg Phe Phe Val Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
            325                 330                 335

Val Leu Val Thr Ile Ile Phe Ile Tyr Glu Lys Arg Arg Lys Pro Glu
        340                 345                 350

Asp Val Leu Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
        370                 375                 380

Ser
385

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccgggttcct gctttcacag aattactcga gtaattctgt gaaagcagga acttttttg      58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccggctgact gtggacaact cgaatctcga gattcgagtt gtccacagtc agttttttg      58

<210> SEQ ID NO 5
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
ccggccagaa tgacaaaggc aagaactcga gt                                      32

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 tcttgcctttt gtcattctgg ttttt                                             25

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccggacagtc ttcactaccg tagaactcga gttctacggt agtgaagact gtttttg           58
```